United States Patent [19]

Wang

[11] Patent Number: 5,436,126
[45] Date of Patent: Jul. 25, 1995

[54] SYNTHETIC PEPTIDES SPECIFIC FOR THE DETECTION OF ANTIBODIES TO HCV, DIAGNOSIS OF HCV INFECTION AND PREVENTION THEREOF AS VACCINES

[75] Inventor: Chang Y. Wang, Great Neck, N.Y.

[73] Assignee: United Biomedical, Inc., Hauppauge, N.Y.

[21] Appl. No.: 805,374

[22] Filed: Dec. 11, 1991

Related U.S. Application Data

[60] Division of Ser. No. 558,799, Jul. 26, 1990, Pat. No. 5,106,726, which is a continuation-in-part of Ser. No. 481,348, Feb. 16, 1990, abandoned, and a continuation-in-part of Ser. No. 510,153, Apr. 16, 1990, abandoned.

[51] Int. Cl.$^6$ ............................................. C12Q 1/70
[52] U.S. Cl. ........................................ 435/5; 435/7.92; 435/968; 436/518; 436/533; 436/820
[58] Field of Search ........................... 435/5, 7.92, 968; 436/533, 518, 820, 804

[56] References Cited

U.S. PATENT DOCUMENTS

| | | | |
|---|---|---|---|
| 4,356,164 | 10/1982 | Tabor et al. | 435/5 |
| 4,395,395 | 7/1983 | Tabor et al. | 424/89 |
| 4,464,474 | 8/1984 | Coursaget et al. | 436/513 |
| 4,542,016 | 9/1985 | Trepo | 424/86 |
| 4,554,101 | 11/1985 | Hopp | 530/324 |
| 4,673,634 | 6/1987 | Seto et al. | 435/5 |
| 4,702,909 | 10/1987 | Villarejos et al. | 424/89 |
| 4,735,896 | 4/1988 | Wang et al. | 435/5 |
| 4,777,245 | 10/1988 | Foung et al. | 530/388.3 |
| 4,833,071 | 5/1989 | Wang et al. | 435/5 |
| 4,871,659 | 10/1989 | Pillot | 435/5 |
| 4,879,212 | 7/1989 | Wang et al. | 435/5 |

FOREIGN PATENT DOCUMENTS

| | | |
|---|---|---|
| 263761 | 4/1988 | European Pat. Off. |
| 293274 | 11/1988 | European Pat. Off. |
| 328403 | 1/1989 | European Pat. Off. |
| 318216 | 5/1989 | European Pat. Off. |
| 335135 | 10/1989 | European Pat. Off. |
| 363025 | 4/1990 | European Pat. Off. |
| 388232 | 9/1990 | European Pat. Off. |
| 609807 | 7/1988 | France |
| 90/00597 | 1/1990 | WIPO |
| WO90/0222-06 | 3/1990 | WIPO |

OTHER PUBLICATIONS

MacCullum F.O., et al.; *Lancet*, 1:622 (1944).
Havens, W. P.: *Proc Soc Exp Biol Med*, 59:148 (1945).
Krugman, S. et al.: *JAMA*, 200:365 (1967).
Prince A. M.: *Lancet*, 2:241 (1974).
Alter H. J., et al: *Lancet*, 2:838 (1975).
Galbraith, R. M., et al: *Lancet*, 2:886 (1975).
Mosley, J. W., et al: *N. Engl J Med*, 296:75 (1977).
(List continued on next page.)

*Primary Examiner*—Esther M. Kepplinger
*Assistant Examiner*—Donna C. Wortman
*Attorney, Agent, or Firm*—Morgan & Finnegan

[57] ABSTRACT

The present invention relates to a method for the detection in body fluids of antibodies to hepatitis C virus (HCV), also known as a non-A non-B hepatitis (NANBH) virus and to the diagnosis of NANBH by the use of a composition of synthetic peptides. Each of these peptides has an amino acid sequence corresponding to immunodominant regions of a fusion protein and a non-structural polypeptide of HCV, SOD/HCV C100 and a postulated HCV structural (core) protein. More specifically, the present invention is directed to the use of a group of synthetic peptides in a prescribed sequence or their analogues for the detection of antibodies to HCV in body fluids. The detection method includes an enzyme-linked immunosorbent assay (ELISA), and other forms of immunoassay procedures. The present invention also relates to a method for generating high titer antibodies to HCV in healthy mammals, including humans, by the use of compositions containing these synthetic peptides, analogues or mixtures thereof, in a free, conjugated or polymeric form as key components in synthetic vaccines for the prevention of non-A non-B hepatitis (NANBH).

14 Claims, 27 Drawing Sheets

OTHER PUBLICATIONS

Dienstag, J. L.: *Rush–Presbyterian–St. Luke's Med Bull,* 15:104 (1976).

Asch, R. D., et al: *N. Engl J Med* 304:989 (1981).

Hollinger F. B., et al: *Viral Hepatitis: 1981 International Symposium,* Szmuness, W., Alter, H. J., Maynard, J. E., (eds), Philadelphia: Franklin Institute Press, p. 361 (1982).

Alter, H. J., et al.: *JAMA,* 246:630 (1981).

Stevens, C. E., et al: *Ann Int. Med,* 101:733 (1984).

Koziol, D. E., et al: *Ann Int Med,* 104:488 (1986).

Sugg, U., et al: *Transfusion,* 28:386 (1988).

Choo Q-L., et al: *Science,* 244:359 (1989).

Kuo, G., et al: *Science,* 244:362 (1989).

Wang, C. Y.: *Synthetic Peptides in Biotechnology,* A. Mizrahi (3d), *Adv in Biotechnological Processes,* 10:131 (1988).

Wang, J. G., et al.: *Proc Natl Acad Sci USA,* 83:6159 (1986).

UBI-Olympus HIV-1 EIA Product Insert, Jun. 1, 1989. License No. 1079, approved by U.S. FDA.

Okamoto, H., et al.: *Jpn. J. Exp. Med.* 60(3):167–177 1990.

Schlesinger, S., et al.: The Togaviridae and Flaviviridae. In: The Viruses, Plenum Press, N.Y., 1986.

Kubo, Y., et al: *Nucleic Acid Res.* 17:10367–10372 (1989).

Slide Presentation by Abbot Laboratories to American Association of Blood Banks (Oct. 1989).

Weiner et al., *Lancet,* 335: 1–3 (Jan. 1990).

McClelland et al., *Lancet,* pp. 36–37 (Jul. 1987).

Feinman et al., *CMA Journal,* 123: 181–184 (Aug. 1980).

T. H. Maugh II, *Science,* 210: 999–1000 (Nov. 1980).

Hantz et al., *J. Med. Virol.,* 5:73–86 (1980).

Tabor et al., *N. Engl. J. of Med.,* 303: 139–143 (1980).

Letters to Editor, *Lancet,* pp. 796–799 (Sep. 30, 1989).

Lynn et al., *MMWR,* 38:529–531 (Aug. 1989).

Polesky et al., *Arch. Pathol. lab. Med.,* 113:232–235 (Mar. 1989).

G. Kolata, *Science,* 23:149–150 (Jul. 1986).

Troisi et al., *Transfusion,* 27:438–440 (1987).

Schumacher et al., *The Ligand Quart.,* 5: 12–27 (Nov. 1982).

Arima T. et al., *Gastroenterologia Jap.,* 24:540–544 (1989).

Arima T. et al., *Gastroenterologia Jap.,* 24:545–548 (1989).

Arima T. et al., *Gastroeneterologia Jap.,* 24:685–691 (1989).

Arima T. et al., *Gastroenterologia Jap.,* 25:2218–232 (1990).

Chou, P. Y. and Fasman, G. D., *Biochemistry,* 13:222–245 (1974).

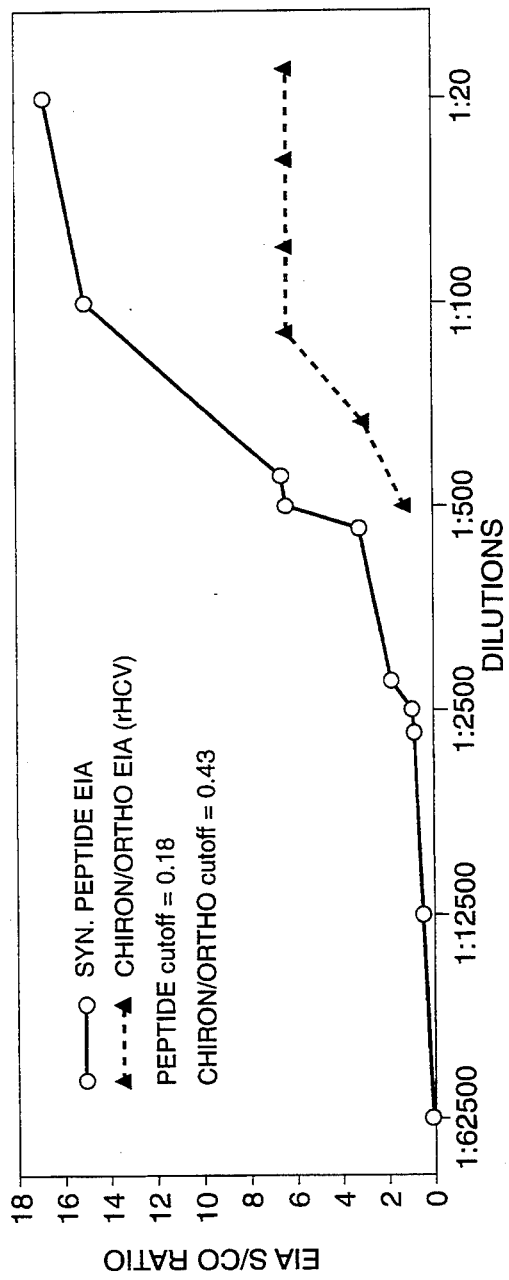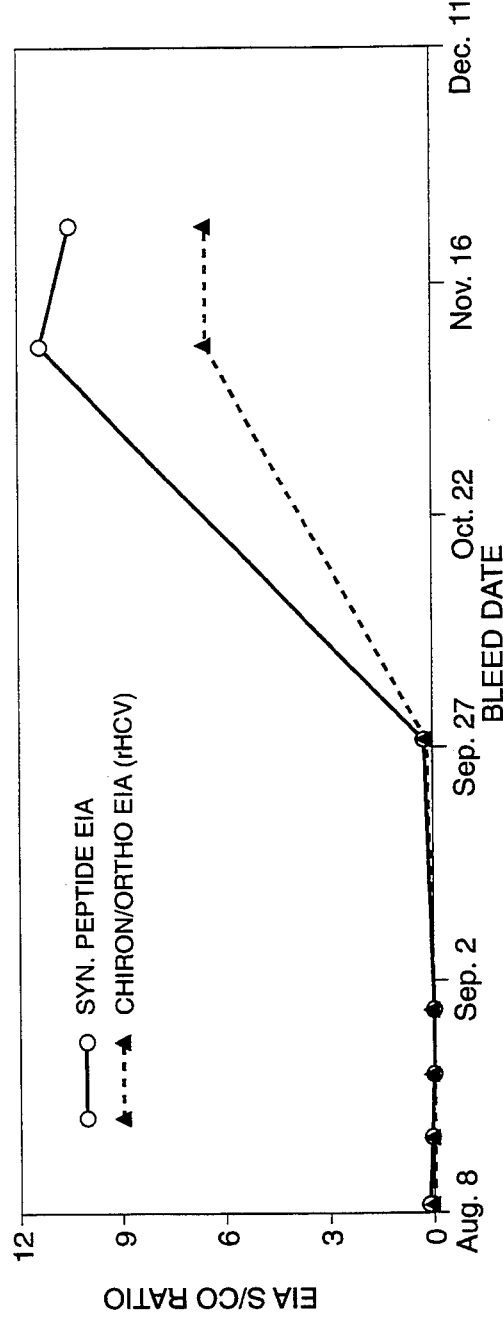

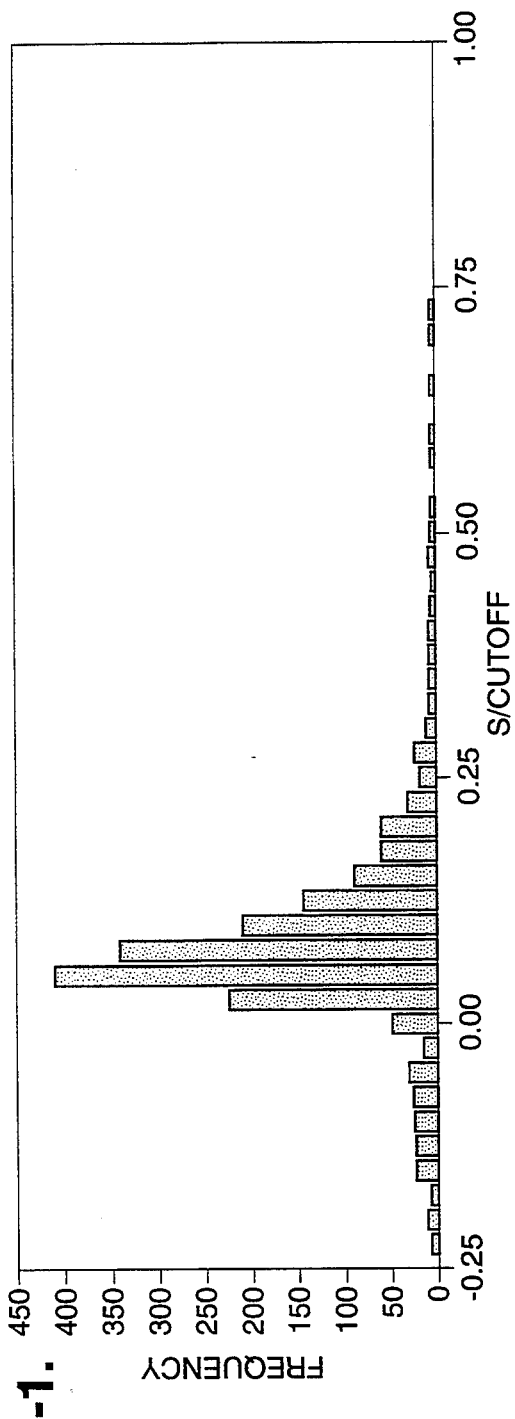
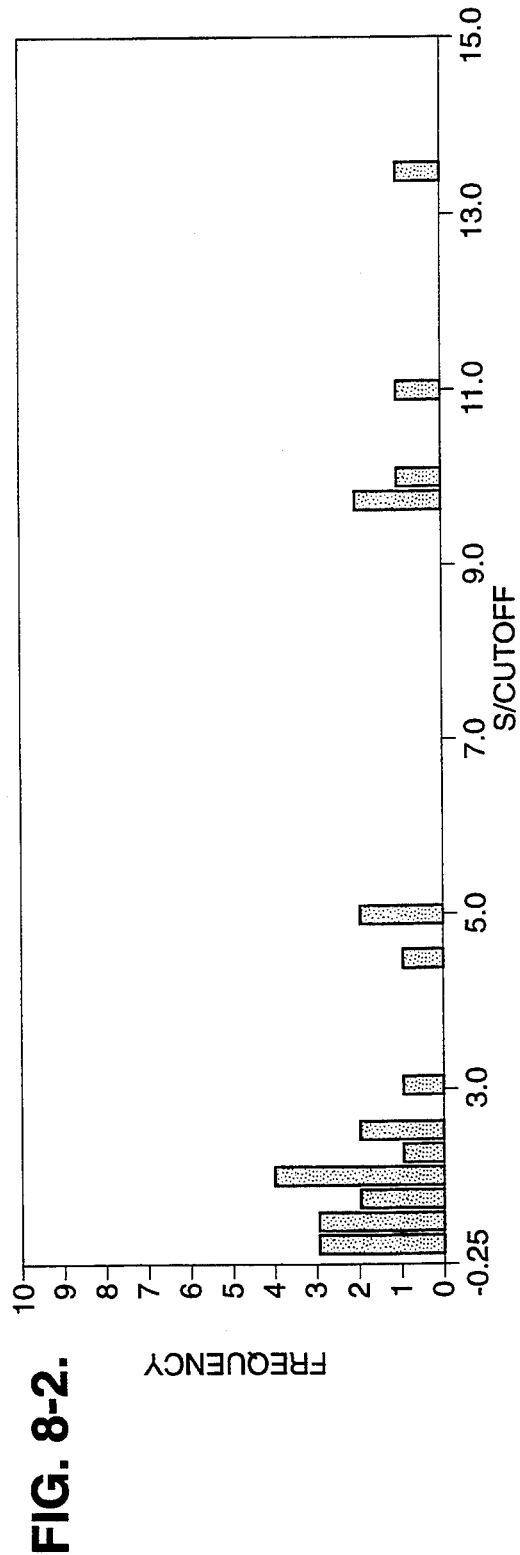
FIG. 8-1.
FIG. 8-2.

SYNTHETIC PEPTIDES SPECIFIC FOR THE DETECTION OF ANTIBODIES TO HCV, DIAGNOSIS OF HCV INFECTION AND PREVENTION THEREOF AS VACCINES

CROSS-REFERENCE TO RELATED APPLICATION

This is a divisional of application Ser. No. 07/558,799, filed Jul. 26, 1990 which is now U.S. Pat. No. 5,106,726, which is a continuation in part application of application Ser. No. 07/481,348, filed Feb. 16, 1990, now abandoned, and application Ser. No. 07/510,153, filed Apr. 16, 1990, now abandoned.

INTRODUCTION

The present invention relates to peptide compositions specific for the diagnosis and prevention of hepatitis C virus (HCV) infection, or non-A non-B hepatitis (NANBH). More particularly, the present invention is directed to synthetic peptide compositions which are specific for the detection of antibodies to HCV in body fluids and immunoassays using the same. The invention also includes the use of the synthetic peptide compositions as antigens for eliciting the production of monoclonal and polyclonal antibodies against HCV and as immunogens in vaccines for the prevention of NANBH or HCV infection.

In the 1940s, two independent investigators concluded that there were at least two types of viral hepatitis, designated as A and B (HAV and HBV) and that infection by one type, either HAV or HBV, did not confer the patient with cross-immunity (1–3). It was only in the 1970's with the introduction of serologic markers for hepatitis A and hepatitis B that it became possible to identify diseases caused by the two viruses and to distinguish between these two types of hepatitis clinically and serologically.

Subsequently, in 1974, Prince et al. suggested that many cases of transfusion hepatitis could not be attributed to HAV or HBV and were caused by an agent other than these viruses. They proposed naming the agent hepatitis C virus (HCV) (4). The presence of another hepatitis causing agent was subsequently confirmed by Alter et al., who reported that although the exclusion of commercial blood donors found to carry hepatitis B surface antigen (HBsAg) significantly reduced the frequency of post-transfusion hepatitis (5), 7 to 10 percent of the 5 million Americans who received transfusions each year still developed hepatitis. In 90% of these post-transfusion hepatitis cases, a specific virus, unrelated to HAV, HBV, Epstein-Barr virus, cytomegalovirus or other viruses which occasionally produce liver diseases, was implicated as the etiologic agent (5). This infection was designated as non-A non-B hepatitis (NANBH).

Over the years, NANBH has been reported in patients undergoing hemodialysis, recipients of renal transplants (6), intravenous drug abusers (7) and patients in institutions for the mentally retarded (8). Further, nurses caring for patients with NANBH have also been found to contract this disease.

Epidemiologic evidence suggests that there may be three types of NANBH: the water-borne epidemic type; the blood or needle associated type; and the sporadically occurring community acquired type. However, the number and precise nature of the causative agents of NANBH still remain not entirely clear.

The acute phase of NANBH is less severe than that of hepatitis B, and the disease is rarely fatal. However, more than a third of the individuals who contract NANBH develop a chronic form of the disease in which they may remain infectious indefinitely. This chronic state may lead to cirrhosis of the liver and eventually to liver cancer.

Many methods have been developed in an attempt to detect the putative NANBH viral antigens and antibodies. These include agar-gel diffusion, counter immunoelectrophoresis, immunofluorescence microscopy, immunoelectron microscopy, radioimmunoassay, and enzyme-linked immunosorbent assay using crude biologic lysates and antibodies from patients. However, none of these assays are sufficiently sensitive, specific, and reproducible for use as a diagnostic test for NANBH. Some of the reactivities detected were later attributable to the presence of antibodies to host cytoplasmic antigens or low levels of a rheumatoid-factor-like substance frequently present in patients with or without hepatic diseases.

In the absence of a definitive test for NANBH, the diagnosis in the past has been one of exclusion. It was based on the clinical presence of acute hepatitis and the persistent absence of serologic markers for hepatitis A and B, Epstein-Barr virus or cytomegalovirus.

Because no specific test for the detection of antibodies to NANBH or HCV has been available, the use of nonspecific tests to screen donors has been adopted in the past decade as a means of preventing at least some post-transfusion NANBH.

One such surrogate test measures liver enzyme levels. The concentrations of some of the liver enzymes, in particular alanine aminotransferase (ALT), are frequently elevated in the blood of patients with active hepatitis. Two independent studies have shown a correlation between donor ALT levels and the incidence of NANBH in transfusion recipients (9–11). However, some studies showed that only about 20 percent of blood donors who transmitted NANBH have elevated liver enzyme concentrations. Other investigators, furthermore, have found that the liver enzyme levels can be increased by extraneous factors, such as heavy drinking.

Epidemiologic circumstances predisposing donor populations to infection with hepatitis B virus may also favor exposure to NANBH agents. A study conducted by Stevens et al. (12) evaluated the risk factors in donors for the presence of antibodies to hepatitis B virus. The results indicated that units of blood which were positive for antibodies to the hepatitis B core antigen (anti-HBc) appeared to present a two to three-fold greater risk of NANBH in the recipients than units without anti-HBc. They concluded that anti-HBc screening of donors might prevent about one third of the cases of NANBH attributable to transfusion, whereas ALT screening might prevent nearly one half of the cases of post transfusion NANBH.

Even with the use of these surrogate tests to establish the diagnosis of NANBH by exclusion, the correct identification of the NANBHV carriers was still far from satisfactory. Firstly, there are a significant number of patients who received blood lacking the surrogate markers and yet developed NANBH. Secondly, there is a minimal overlap between donors with elevated ALT levels and those with anti-HBc. Lastly, there are recipients of blood units which were positive for a surrogate marker, but who did not become infected with NANBHV, also known as HCV (13–15).

Thus, there is an urgent demand for a sensitive and specific method to identify carriers of NANBHV and to screen out contaminated blood or blood products. In addition, there is also a need for an effective vaccine and/or therapeutic agent for the prevention and/or treatment of the disease.

Recently, a group of scientists at Chiron Corp. constructed a random-primed complementary DNA (cDNA) library from plasma containing the uncharacterized NANBH agent (16). They screened the library with serum from a patient diagnosed with NANBH and isolated a cDNA clone that encodes an antigen associated specifically with NANBH. This clone was found to be derived from the genome of an agent similar to the togaviridae or flaviviridae (16). The newly identified NANBH agent was called hepatitis C virus (HCV). A specific assay for this blood-borne NANBH virus was developed based on a fusion polypeptide of human superoxide dismutase (SOD) and 363 HCV amino acids, designated as SOD/HCV C100-3 (17). SOD/HVC C-100 was cultured from a clone of recombinant yeast, purified, and used to capture circulating viral antibodies (17). A family of cDNA sequences derived from this hepatitis C virus was subsequently reported in detail (18).

However, the nucleotide sequence of HCV disclosed by the Chiron group covers only about 75% of the HCV genome and represents only the nonstructural genes.

More recently Mayumi, et al. determined the 5'-terminal sequence of the genome of HCV for two distinct HCV strains in human and chimpanzee carriers (27). The 5'-terminal sequence contained a 5' non-coding region of at least 324 nucleotides, well preserved in the two strains. The non-coding region was followed by a coding region of 1348 nucleotides continuing beyond the reported sequence of the prototype HCV which spanned 7310 nucleotides (18). Based on these results (18,27), HCV is considered to possess an uninterrupted open reading frame encoding at least 2886 amino acid residues.

A comparison of the complete nucleotide sequence of the Hepatitis C Virus to that of other Flaviviruses (28) has led us to postulate that two structural genes encoding for the core (or nucleocapsid protein) and the envelope proteins were contained in the HCV genome located in the upstream and downstream region respectively of the 5'-terminal sequence as reported by the Mayumi group (27). By careful analysis of the whole HCV genome structure and the predicted amino acid sequence encoded in the structural and non-structural proteins, we have now identified and characterized by an extensive series of experiments and through serological validation, the immunodominant regions of the HCV proteins.

The predicted amino acid sequence of the HCV genome is presented in Table 6, wherein the sequence for (a) is the sequence for J-1 (27, 29), (b) is the sequence for J-4 (27) and (c) is the sequence for the prototype PT (18). These show where conservative substitutions, deletions or substitutions can be made.

TABLE 6

```
(a) M S T I P K P Q R K T K R N T N R R P Q D V K F P G G G Q I V G G V Y L L P R R G P R L G V R A T R    50
(b) - - - N - - - - - - - - - - - - - - - - - - - - - - - - - - - - - - - - - - - - - - - - - - - - -

K T S E R S Q P R G R R Q P I P K V R R P E G R T W A Q P G Y P W P L Y G N E G C G W A G W L L S P   100
    - - - - - - - - - - W - - - - - A - - - - - - A - - - - - - - - - - - - - - L - - - - - - - - - -

R G S R P S W G P T D P R R T S R N L G K V I D T L T C G F A D L M G Y I P L V G A P L G G A A R A   150
    - - - - - - - - - - - - - - - - - - - - - - - - - - - - - - - - - - - - - - - - - - - - - - - - -

L A H G V R V L E D G V N Y A T G N L P G C S F S I F L L A L L S C L T V P A S A Y Q V R N S T G L   200
    - - - - - - - - - - - - - - - - - - - - - - - - - - - - I - - - - - E - - - V S - I

Y H V T N D C P N S S I V Y E A H D A I L H T P G C V P C V R E G N V S R C W V A M T P T V A T R D   250
    - - - - - - - - S - - - - - - - - - A - M - M - - - - - - - - - - - - D - S - - - - - - L - - - L - A - N

G K L P A T Q L R R H I D L L V G S A T L C S A L Y V G D L C G S V F L I G Q L F T F S P R R H W T   300
    A S V - T - T I - - - V - - - - - A - A F - - - M - - - - - - - - - - - V S - - - - - - - - - - E -

T Q G C N C S I Y P G H I T G H R M A W D M M M N W S P T A A L V M A Q L L R I P Q A I L D M I A G   350
    V - D - - - - - - - - L S - - - - - - - - - - - - - - - - - T - - - V S - - - - - - - - V V - - V - -

A H W G V L A G I A Y F S M V G N W A K V L V V L L L F A G V D A E T I V S G G Q A A R A M S G L V   400
    - - - - - - - - - L - - Y - - - - - - - - - - - I - A - - - - - - - - - - - Y T - - - A - S H T T - T - A

S L F T P G A K Q N I Q L I N T N G S W H I N S T A L N C N E S L N T G W L A G L I Y Q H K F N S S   450
    - - - S - - - S - R - - - V - - - - - - - - - R - - - - - - D - - H - - F - - A - F - T - R - - - -

(a) G C P E R L A S C R R L T D F D Q G W G P I S H A N G S G P D Q R P Y C W H Y P P K P C G I V P A K   500
(b) - - - - - M - - - - I D W - A - - - - - - T Y T E P D S - - - - - - - - - - - A - R - - - - - - - S
(c) - - - - - - - - - - - - - - - - - - - - - - - - - - - - Y - - - - - - - - - - - - - - - - - - - - -

S V C G P V Y C F T P S P                                                                            550
    Q - - - - - - - - - - - -
    - - - -   - - - - - - - - - V V V G T T D R S G A P T Y S W G E N D T D V F V L N N T R P P L G N W F

G C T W M N S T G F T K V C G A P P C V I G G A G N N T L H C P T D C F R K H P D A T Y S R C G S G   600

P W I T P R C L V D Y P Y R L W H W P C T I N Y T I F K I R M Y V G G V E H R L E A A C N W T R G E   650

R C D L E D R D R S E L S P L L L T T T Q W Q V L P C S F T T L P A L S T G L I H L H Q N I V D V Q   700

Y L Y G V G S S I A S W A I K W E Y V V L L F L L L A D A R V C S C L W M M L L I S Q A E A A L Q N   750
```

TABLE 6-continued

```
            LVI LNAAS LAGTHGLVS FLVFFCF AWYLKGKWVP GAVYTFYGMWP LLLLL    800
            LALPQRAYALDTEVAAS CGGVVLVGLMALTLS PYYKRYI SWCLWWLQYFL        850
            TRVQAQLHVWI PPLNVRGGRDAVI LLMLAVHPTLVFDI TKLLLAVFGPLW         900
            I LQAS LLKVP WF VRVQGLLRF CALARKMI GGHYVQMVI I KLGALTGTYVY    950
            NHLTPLRDWAHNGLRDLAVAVEPVVFSQMETKLI TWGADTAACGDI I NGL          1000
            PVS ARRGREI LLGPADGMVS KGWRLLAPI TAYAQQTRGLLGCI I TSLTGR       1050
            DKNQVEGEVQI VSTAAQTFLATCI NGVCWTVYHGAGTRTI ASPKGPVI QM        1100
            YTNVDQDLVGWPAPQGS RSLTPCTCGSS DLYLVTRHADVI PVRRRGASRG         1150
            SLLSPROI SYLKGSS GGPLLCPAGHAVGI FRAAVCTRGVAKAVDFI PVEN        1200
            LETTMRSPVFTDNSS PPVVPQSFQVAHLHAPTGS GKSTKVPAAYAAQGYK          1250
            VLVLNPS VAATLGFGAYMS KAHGI DPNI RTGVRTI TTGSPI TYSTYGKFL      1300
            ADGGCS GGAYDI I I CDELHSTDATS I LGI GTVLDQAETAGATLVVLATAT     1350
            PPGS VTVPHPNI EEVALS TTGEI PFYGKAI PLEVI KGGRHLI FCHS KKKC    1400

(a)                                                                        - 1450
(c) DELAAKLVALGI NAVAYYRGLDVS VI PTSGDVVVVATDALMTGYTGDFDS
    . . . . . . . . . . . . . . . . . . . . . T- Y- . . . . . . . . . . . . . . . . . RR- - - -  1500
            VI DCNTCVTQTVDFSLDPTFTI ETI TLPQDAVSRTQRRGRTGRGKPGI YR
    - - T- . . . . . . A- . . . . . . . . . . . . . . . . . . . S- . . . . . . L- . . . . . . . .  1550
            FVAPGERPS GMFDSS VLCECYDAGCAWYELTPAETTVRLRAYMNTPGLPV
    . . . . . . . . S- . . . . . . . . . . . . . . . . . . . . A- D- F- . . . . . . . . . . . . . K- -  1600
            CNDHLEFWEGVFTGLTHI DAHFLS QTKQS GENLPYLVAYQATVCARAQAP
    . . . . . . . . . . . . . . . . . . . . . . . . . . . . . . V- . . . . . I - -  1650
            PPS WDQMWKCLI RLKPTLHGPTPLLYRLGAVQNEI TLTHPVTKYI MTCMS
            ADLEVVTSTWVLVGGVLAALAAYCLSTGCVVI VGRVVLSGKPAI I PDREV          1700
            LYREFDEMEECSQHLPYI ENGMMLAENFKQKALGLLQTASRQAEVI APAV          1750
            QTNWQKLETFWAKHMWNFI SGI QYLAGLSTLPGNPAI ASLMAFTAAVTSP         1800
            LTTSQTLLFNI LGGWVAAQLAAPGAATAFVGAGLAGAAI GSVGLGKVLI D          1850
            I LAGWGAGVAGALVAFKI MSGEVPSTEDLVNLLPAI LSPGALVVGVVCAA         1900
            I LRRHVGPGEGAVNWMNRLI AFAS RGNHVSPTHYVPESDAAARVTAI LSS         1950
            LTVTQLLRRLHQWI SSECTTPCSGS WLRDI WDWI CEVLSDFKTWLKAKLM        2000
            PQLPGI PFVSCQRGYKGVWRVDGI MHTRCHCGAEI TGHVKNGTMRI VGPR        2050
            TCRNMWSGTFPI NAYTTGPCTPLPAPNYTFALWRVSAEEYVEI RQVGDFH         2100
            YVTGMTTDNLKCPCQVPSPEFFTELDGVRLHRFAPPCKPLLREEVS FRVG           2150
            LHEYPVGS QLPCEPEPDVAVLTSMLTDPSHI TAEAAGRRLARGS PPSVAS         2200
            SSASQLS APSLKATCTANHDSPDAELI EANLLWRQEMGGNI TRVESENKV        2250
            VI LDSFDPLVAEEDEREI SVPAEI LRKSRRFAQALPVWARPDYNPPLVET        2300
            WKKPDYEPPVVHGCPLPPPKS PPVPPPRKKRTVVLTESTLSTALAELATR          2350
            SFGSSSTSGI TGDNTTTSSEPAPSGCPPDSDAESYSSMPPLEGEPGDPDL           2350
            SDGSWSTVSSEANAEDVVCCSMSYSWTGALVTPCAAEEQKLPI NALSNSL          2450
            LRHHNLVYSTTS RSACQRQKKVTFDRLQVLDSHYQDVLKEVKAAASKVKV         2500
            NLLSVEEACSLTPPHSAKSKFGYGAKDVRCHARKAVTHI NSVWKDLLEDN           2550
            VTPI DTTI MAKNEVFCVQPEKGGRKPARLI VFPDLGVRVCEKMALYDVVT         2600
```

-continued

```
KL P L A VMGS S YGF Q YS P GQ R VEF L VQ A WKS KKT P MGF S YDT R CF DS T VT E    2650

S DI R R E E AI  YQ C CDL DP Q AR VAI  KS L T ER L YVGGP L T NS R GENCGY R R CR    2700

AS R AS GVL T T S CGNT L T CYI  KAR AACR AAGL Q DC T ML VCGDDL VVI  CES A    2750

GVQ E DAAS L R AF T EAMT R YS AP P GDP P QP E YDL EL I  T S CS S NVS VAHDGA    2800

GKR V Y YL T R DP T T P L AR AAWE T AR HT P VNS WL GNI  I  MF AP T L WAR MI  L MY    2850

HF F S VL I  AR DQ L E Q AL DCE I  YGACYS I  EP L DL P P I  I Q R L    2889
```

Synthetic peptides have been increasingly used to map antigenic or immunogenic sites on the surface of proteins, an approach recently termed "site-directed-serology". The present inventor (Wang, C. Y.) and a colleague have taken this approach to identify and characterize highly antigenic epitopes on the envelope proteins of HIV and to develop sensitive and specific immunoassays for the detection of antibodies to HIV (previously designated HTLV-III) (19-21). See also U.S. Pat. No. 4,735,896, issued Apr. 5, 1988 and U.S. Pat. No. 4,879,212 issued Nov. 7, 1989, the contents of which are, hereby, fully incorporated by reference (22, 23). Subsequently, a series of finely mapped and well-characterized HTLV-I/II related synthetic peptides were employed in the development of synthetic peptide-based diagnostic assays for the detection of HTLV-I/II antibodies in infected individuals (24, 25). See also U.S. Pat. No. 4,833,071 issued May 23, 1989, U.S. Ser. No. 07/297,635 filed Jan. 13, 1989 and U.S. Ser. No. 07/469,294 filed Jan. 24, 1990. These assays have provided superior sensitivity, excellent specificity, and, in certain cases, an unmatched capability to differentiate infections with two closely related viruses, thus overcoming many of the existing problems associated with biologically-derived tests based on either vital lysate or recombinant DNA-derived protein.

It is, therefore, an objective of the present invention to develop a detection or diagnostic procedure to identify and monitor HCV infection early in the disease cycle.

Another objective is to develop a test procedure that is highly sensitive and accurate.

A further objective is to chemically synthesize a test reagent which can then be used to detect the presence of antibodies to HCV in body fluids and diagnose NANBH.

Another objective is to develop a vaccine which, when introduced into healthy mammals, including humans, will stimulate production of efficacious antibodies to HCV, thereby providing protection against HCV infection.

A further objective is to provide a synthetic immunogen which can be used in mammals for the development of monoclonal and polyclonal antibodies to HCV.

LIST OF REFERENCES

1. MacCallum F.O., Bauer D.J.: Homologous serum jaundice: transmission experiments with human volunteers. *Lancet*, 1:6222 (1944.
2. Havens W. P.: Experiment in cross immunity between infectious hepatitis and homologous serum jaundice. *Proc Soc Exp Biol Med*, 59:148 (1945).
3. Krugman S., Giles J. P., Hammond J.: Infectious hepatitis. Evidence for two distinctive clinical, epidemiological and immunological types of infection. *JAMA*, 200:365 (1967).
4. Prince A. M., Brotman B., Grady G. F., et al: Long-incubation post-transfusion hepatitis without serological evidence of exposure to hepatitis-B virus. *Lancet*, 2:241 (1974 ).
5. Alter H. J., Purcell R. H., Holland P. V., et al: Clinical and serological analysis of transfusion-associated hepatitis. *Lancet*, 2:838 (1975).
6. Galbraith R. M., Protmann B., Edleston A. L. W. F., et al: chronic liver disease developing after outbreak of HBsAg-negative hepatitis in haemodialysis unit. *Lancet*, 2:886 (1975 ).
7. Mosley J. W., Redeker A. G., Feinstone S. M., et al: Multiple hepatitis viruses in multiple attacks of acute vital hepatitis. *N Engl J Med*, 296:75 (1977).
8. Dienstag J. L., Purcell R. H.: Epidemiology of hepatitis non-A, non-B. *Rush-Presbyterian-St. Luke's Med Bull*, 15:104 (1976).
9. Aach R. D., Szmuness W., Mosley J. W., et al: Serum alanine aminotransferase of donors in relation to the risk of non-A, non-B hepatitis in recipients: the Transfusion-Transmitted Viruses Study. *N Engl J Med* 304: 989 (1981 ).
10. Hollinger F. B., Mosley J. W., Szmuness W., et al: "Non-A, non-B hepatitis following blood transfusion: risk factors associated with donor characteristics" in *Vital Hepatitis*: 1981 *International Symposium*, Szmuness W., Alter H. J., Maynard J. E., (eds), Philadelphia: Franklin Institute Press, p361 (1982).
11. Alter H. J., Purcell R. H., Holland P. V., Alling D. W., Koziol DE: Donor transaminase and recipient hepatitis: impact on blood transfusion services. *JAMA*, 246:630 (1981 ).
12. Stevens C. E., Aach R. D., Hollinger F. B., et al: Hepatitis B virus antibody in blood donors and the occurrence of non-A, non-B hepatitis in transfusion recipients. *Ann Int Med*, 101:733 (1984).
13. Aach R. D., Szmuness W., Mosley J. W., et al: Serum alanine aminotransferase of donors in relation to the risk of non-A, non-B hepatitis in recipients: The Transfusion-Transmitted Virus Study. *N Engl J Med*, 304:989 (1981).
14. Koziol D. E., Holland P. V., Alling D. W., et al: Antibody to hepatitis B core antigen as a paradoxical marker for non-A, non-B hepatitis agents in donated blood. *Ann Int Med*, 104:488 (1986).
15. Sugg U., Schenzle D., Hess G.: Antibodies to hepatitis B core antigen in blood donors screened for alanine aminotransferase level and hepatitis non-A, non-B in recipients. *Transfusion*, 28:386 (1988).
16. Choo Q-L, Kuo G., Weiner A., et al: Isolation of a cDNA clone derived from a blood-borne non-A, non-B viral hepatitis genome. *Science*, 244:359 (1989).

17. Kuo G., Choo Q-L, Alter H. J., et al: An assay for circulating antibodies to a major etiologic virus of human non-A, non-B hepatitis. *Science*, 244:362 (1989).
18. Houghton M., Choo Q-L, Kuo G.: NANBV diagnostics and vaccines. EPO 0318218AT, 1989
19. Wang C. Y.: Synthetic-peptide-based immunodiagnosis of retrovirus infections: current status and future prospects. In: *Synthetic Peptides in Biotechnology*, A. Mizrahi (ed), *Adv in Biotechnological Processes*, 10:131 (1988).
20. Wang J. G., Steel S., Wisniewolski R., Wang C. Y.: Detection of antibodies to HTLV-III using a synthetic peptide of 21 amino acid residues corresponding to a highly antigenic segment of gp41 envelope protein. *Proc Natl Acid Sci USA*, 83:6159 (1986).
21. Wang C. Y.: European Patent Application Publication: EPO 0328403 (1989). Synthetic peptides related to the HIV-gp120 env. protein, and their use.
22. Wang C. Y., Wang J. G.: U.S. Pat. No. 4879212 (1989). Peptide composition and method for the detection of antibodies to HTLV-III.
23. Wang C. Y., Wang J. G.: U.S. Pat. No. 4,735,896 (1988). Synthetic peptide and process of using same for the detection and diagnosis of AIDS and pre-AIDS conditions.
24. Wang C. Y., Wang J. G., Walters D. W.: U.S. Pat. No. 4833071 (1989). Peptide composition as antigen for detection of antibodies to HTLV-1, as a vaccine for ATL, and methods therefor.
25. Wang C. Y.: U.S. Ser. No. 07/297635. Synthetic peptide compositions with immunoreactivities to antibodies to HTLV.
26. UBI-OLYMPUS HIV-1 EIA Product Insert. Jun. 1, 1989. License No. 1079, approved by US FDA.
27. Okamoto, H., Okada, S., Sugiyama, S., Yotsumoto, S., Tanaka, T., Yoshizawa, H., Tsuda, F., Miyakawa, Y., and Mayumi, M.: The 5' Terminal Sequence of the Hepatitis C virus genome, Jpn. J. Exp Med. 1990 (in press).
28. Schlesinger, S., and Schlesinger, M., (Ed.) The Togaviridae and Flaviviridae. In: The Viruses. Plenum Press, New York, 1986.
29. Kubo, Y., Takeuchi, K., et al: cDNA fragment of Hepatitis C virus isolated from an implicated donor of post-transfusion Non-A, Non-B Hepatitis in Japan. Nucleu Acid Res. 17:10367-10372 (1989).

BRIEF DESCRIPTION OF THE INVENTION

According to the present invention, a series of synthetic peptides representing immunodominant regions of the hepatitis C virus (HCV) proteins, each arranged in a specific sequence, has been identified and made by solid phase peptide synthesis. These peptides have been found to be useful in a highly sensitive and accurate method for the early detection of antibodies to HCV in sera and body fluids and the diagnosis of non-A non-B hepatitis (NANBH). Because of their high immunoreactivity, it is expected that these peptides are also useful in stimulating production of antibodies to HCV in healthy mammals such as Balb/C mice, and in a vaccine composition to prevent HCV or NANBHV infection.

According to the present invention, a peptide composition useful for the detection of antibodies to HCV and diagnosis of NANBH comprises a peptide selected from the group. of peptides with the following sequences:

Glu—Glu—Cys—Ser—Gln—His—Leu—Pro—Tyr—Ile—Glu—Gln—
Gly—Met—Met—Leu—Ala—Glu—Gln—Phe—Lys—Gln—Lys—Ala—
Leu—Gly—Leu—Leu—Gln—Thr—Ala—Ser—Arg—Gln—Ala—Glu—
Val—Ile—Ala—Pro—X  (I)   (i)

Ile—Ile—Pro—Asp—Arg—Glu—Val—Leu—Tyr—Arg—Glu—Phe—
Asp—Glu—Met—Glu—Glu—Cys—Ser—Gln—His—Leu—Pro—Tyr—
Ile—Glu—Gln—Gly—Met—Met—Leu—Ala—Glu—Gln—Phe—Lys—
Gln—Lys—Ala—Leu—Gly—Leu—X  (II)   (ii)

Ser—Gly—Lys—Pro—Ala—Ile—Ile—Pro—Asp—Arg—Glu—Val—
Leu—Tyr—Arg—Glu—Phe—Asp—Glu—Met—Glu—Glu—Cys—Ser—
Gln—His—Leu—Pro—Tyr—Ile—Glu—Gln—Gly—Met—Met—Leu—
Ala—Glu—Gln—Phe—Lys—Gln—Lys—Ala—Leu—Gly—Leu—X  (IIH)  (iii)

Cys—Val—Val—Ile—Val—Gly—Arg—Val—Val—Leu—Ser—Gly—
Lys—Pro—Ala—Ile—Ile—Pro—Asp—Arg—Glu—Val—Leu—Tyr—
Arg—Glu—Phe—Asp—Glu—Met—Glu—Glu—Cys—Ser—Gln—His—
Leu—Pro—Tyr—Ile—X  (III)  (iv)

Ser—Gly—Lys—Pro—Ala—Ile—Ile—Pro—Asp—Arg—Glu—Val—
Leu—Tyr—Arg—Glu—Phe—Asp—Glu—Met—Glu—Glu—Cys—Ser—
Gln—His—Leu—Pro—Tyr—Ile—Glu—Gln—Gly—Met—Met—Leu—
Ala—Glu—Gln—Phe—X  (IV)  (v)

Lys—Gln—Lys—Ala—Leu—Gly—Leu—Leu—Gln—Thr—Ala—Ser—
Arg—Gln—Ala—Glu—Val—Ile—Ala—Pro—Ala—Val—Gln—Thr—
Asn—Trp—Gln—Lys—Leu—Glu—Thr—Phe—Trp—Ala—Lys—His—
Met—Trp—Asn—Phe—X  (V)  (vi)

Glu—Gln—Gly—Met—Met—Leu—Ala—Glu—Gln—Phe—Lys—Gln—
Lys—Ala—Leu—Gly—Leu—Leu—Gln—Thr—Ala—Ser—Arg—Gln—
Ala—Glu—Val—Ile—Ala—Pro—Ala—Val—Gln—Thr—Asn—Trp—
Gln—Lys—Leu—Glu—Thr—X  (VI)  (vii)

Pro—Gly—Ala—Leu—Val—Val—Gly—Val—Val—Cys—Ala—Ala—
Ile—Leu—Arg—Arg—His—Val—Gly—Pro—Gly—Glu—Gly—Ala—
Val—Gln—Trp—Met—Asn—Arg—Leu—Ile—Ala—Phe—Ala—Ser—
Arg—Gly—Asn—His—Val—Ser—Pro—X  (VII)  (viii)

Ser—Thr—Ile—Pro—Lys—Pro—Gln—Arg—Lys—Thr—Lys—Arg— (ix)
Asn—Thr—Asn—Arg—Arg—Pro—Gln—Asp—Val—Lys—Phe—Pro—
Gly—Gly—Gly—Gln—Ile—Val—Gly—Gly—Val—Tyr—Leu—Leu—
Pro—Arg—Arg—Gly—Pro—Arg—Leu—Gly—Val—Arg—Ala—Thr—
Arg—Lys—Thr—Ser—Glu—Arg—Ser—Gln—Pro—Arg—Gly—Arg—
Arg—X, and (VIII)

wherein X is —OH or —NH₂, and analogues, segments, mixtures, combinations, conjugates and polymers thereof.

The amino acids in this application are abbreviated as shown herein below:

| | | |
|---|---|---|
| A = | Ala = | alanine, |
| R = | Arg = | arginine, |
| D = | Asp = | Aspartic acid, |
| N = | Asn = | asparagine, |
| Q = | Gln = | glutamine, |
| E = | Glu = | glutamic acid, |
| L = | Leu = | leucine, |
| K = | Lys = | lysine, |
| H = | His = | histidine, |
| T = | Thr = | threonine, |
| G = | Gly = | glycine, |
| I = | Ile = | isoleucine, |
| F = | Phe = | phenylalanine, |
| S = | Ser = | serine, |
| W = | Trp = | tryptophan, |
| Y = | Tyr = | tyrosine, |
| V = | Val = | valine, |
| C = | Cys = | cysteine, |
| P = | Pro = | proline |

An example of a combination is: Cys-Val-Val-Ile-Val-Gly-Arg-Val-Val-Leu-Ser-Gly-Lys-Pro-Ala-Ile-Ile-Pro-Asp-Arg-Glu-Val-Leu-Tyr-Arg-Glu-Phe-Asp-Glu-Met-Glu-Glu-Cys-Ser-Gln-His-Leu-Pro-Tyr-Ile-Glu-Gln-Gly-Met-Met-Leu-Ala-Glu-Gln-Phe-Lys-Gln-Lys-Ala-Leu-Gly-Leu-Leu-Gln-Thr-Ala-Ser-Arg-Gln-Ala-Glu-Val-Ile-Ala-Pro-X wherein X is —OH or —NH₂. An example of a segment of Peptide II is: Pro-Asp-Arg-Glu-Val-Leu-Tyr-Arg-Glu-Phe-Asp-Glu-Met-Glu-Glu-Cys-Ser-Gln-His-Leu-Pro-Tyr-Ile-Glu-Gln-Gly-Met-Met-Leu-Ala-Glu-Gln-Phe-Lys-Gln-Lys-Ala-Leu-Gly-Leu-X wherein X is —OH or —NH₂ (IIF). An example of a segment of Peptide III is: Ser-Gly-Lys-Pro-Ala-Ile-Ile-Pro-Asp-Arg-Glu-Val-Leu-Tyr-Arg-Glu-Phe-Asp-Glu-Met-Glu-Glu-Cys-Ser-Gln-His-Leu-Pro-Tyr-Ile-X wherein X is —OH or —NH₂ (IIID). An example of a segment of Peptide IX is Trp-Ala-Gln-Pro-Gly-Tyr-Pro-Trp-Pro-Leu-Tyr-Gly-Asn-Glu-Gly-Cys-Gly-Trp-Ala-Gly-Trp-Leu-Leu-Ser-Pro-Arg-Gly-Ser-Arg-Pro-Ser-Trp-Gly-Pro-Thr-Asp-Pro-Arg-Arg-Arg-Ser-Arg-Asn-Leu-Gly-X (IXC).

The present invention also includes a highly sensitive and accurate method of detecting antibodies to HCV in body fluids and of diagnosing NANBH comprises the following steps:

A. Preparing a peptide composition comprising a peptide selected from the group having the following amino acid sequences:

Glu—Glu—Cys—Ser—Gln—His—Leu—Pro—Tyr—Ile—Glu—Gln— (i)
Gly—Met—Met—Leu—Ala—Glu—Gln—Phe—Lys—Gln—Lys—Ala—
Leu—Gly—Leu—Leu—Gln—Thr—Ala—Ser—Arg—Gln—Ala—Glu—
Val—Ile—Ala—Pro—X (I)

Ile—Ile—Pro—Asp—Arg—Glu—Val—Leu—Tyr—Arg—Glu—Phe— (ii)
Asp—Glu—Met—Glu—Glu—Cys—Ser—Gln—His—Leu—Pro—Tyr—
Ile—Glu—Gln—Gly—Met—Met—Leu—Ala—Glu—Gln—Phe—Lys—
Gln—Lys—Ala—Leu—Gly—Leu—X (II)

Ser—Gly—Lys—Pro—Ala—Ile—Ile—Pro—Asp—Arg—Glu—Val— (iii)
Leu—Tyr—Arg—Glu—Phe—Asp—Glu—Met—Glu—Glu—Cys—Ser—
Gln—His—Leu—Pro—Tyr—Ile—Glu—Gln—Gly—Met—Met—Leu—
Ala—Glu—Gln—Phe—Lys—Gln—Lys—Ala—Leu—Gly—Leu—X (IIH)

Cys—Val—Val—Ile—Val—Gly—Arg—Val—Val—Leu—Ser—Gly— (iv)
Lys—Pro—Ala—Ile—Ile—Pro—Asp—Arg—Glu—Val—Leu—Tyr—
Arg—Glu—Phe—Asp—Glu—Met—Glu—Glu—Cys—Ser—Gln—His—
Leu—Pro—Tyr—Ile—X (III)

Ser—Gly—Lys—Pro—Ala—Ile—Ile—Pro—Asp—Arg—Glu—Val— (v)
Leu—Tyr—Arg—Glu—Phe—Asp—Glu—Met—Glu—Glu—Cys—Ser—
Gln—His—Leu—Pro—Tyr—Ile—Glu—Gln—Gly—Met—Met—Leu—
Ala—Glu—Gln—Phe—X (IV)

Lys—Gln—Lys—Ala—Leu—Gly—Leu—Leu—Gln—Thr—Ala—Ser— (vi)
Arg—Gln—Ala—Glu—Val—Ile—Ala—Pro—Ala—Val—Gln—Thr—
Asn—Trp—Gln—Lys—Leu—Glu—Thr—Phe—Trp—Ala—Lys—His—
Met—Trp—Asn—Phe—X (V)

Glu—Gln—Gly—Met—Met—Leu—Ala—Glu—Gln—Phe—Lys—Gln— (vii)
Lys—Ala—Leu—Gly—Leu—Leu—Gln—Thr—Ala—Ser—Arg—Gln—
Ala—Glu—Val—Ile—Ala—Pro—Ala—Val—Gln—Thr—Asn—Trp—
Gln—Lys—Leu—Glu—Thr—X (VI)

Pro—Gly—Ala—Leu—Val—Val—Gly—Val—Val—Cys—Ala—Ala— (viii)
Ile—Leu—Arg—Arg—His—Val—Gly—Pro—Gly—Glu—Gly—Ala—
Val—Gln—Trp—Met—Asn—Arg—Leu—Ile—Ala—Phe—Ala—Ser—
Arg—Gly—Asn—His—Val—Ser—Pro—X (VII)

```
Ser—Thr—Ile—Pro—Lys—Pro—Gln—Arg—Lys—Thr—Lys—Arg—        (ix)
Asn—Thr—Asn—Arg—Arg—Pro—Gln—Asp—Val—Lys—Phe—Pro—
Gly—Gly—Gly—Gln—Ile—Val—Gly—Gly—Val—Tyr—Leu—Leu—
Pro—Arg—Arg—Gly—Pro—Arg—Leu—Gly—Val—Arg—Ala—Thr—
Arg—Lys—Thr—Ser—Glu—Arg—Ser—Gln—Pro—Arg—Gly—Arg—
Arg—X, and                                               (VIII)

Gly—Arg—Arg—Gln—Pro—Ile—Pro—Lys—Val—Arg—Arg—Pro—        (x)
Glu—Gly—Arg—Thr—Trp—Ala—Gln—Pro—Gly—Tyr—Pro—Trp—
Pro—Leu—Tyr—Gly—Asn—Glu—Gly—Cys—Gly—Trp—Ala—Gly—
Trp—Leu—Leu—Ser—Pro—Arg—Gly—Ser—Arg—Pro—Ser—Trp—
Gly—Pro—Thr—Asp—Pro—Arg—Arg—Arg—Ser—Arg—Asn—Leu—
Gly—X                                                    (IX)
``` wherein X is —OH or —NH₂, and analogues, segments, mixtures, combinations, conjugates and polymers thereof; and B. Using an effective amount of the peptide composition as the antigen in an immunoassay procedure.

Further, according to the present invention, the peptides by themselves, or when coupled to a protein or a polymeric carrier of homo or hetero dimers or higher oligomers by use of homo or hetero functional multivalent cross linking reagents, or when directly synthesized and conjugated to a branching polyvalent lysine resin, can be used to elicit the production of antibodies to HCV in healthy mammals, including humans.

The method comprises introducing an effective amount of the peptide composition containing each of the individual peptides, analogues or segments or a mixture or a combination thereof, or in a polymeric form, into the body of a healthy mammal by intraperitoneal or subcutaneous injection.

Vaccines containing the peptides according to the present invention as the key immunogen may also be prepared. It is expected that such vaccine compositions may be useful to prevent HCV infection or NANBH.

BRIEF DESCRIPTION OF THE DRAWINGS

FIGS. 2-1 and 2-2 are comparisons of the signal to cutoff ratio between the peptide based HCV-EIA employing only the non-structural protein sequence derived Peptide IIG of the present invention and that of the recombinant SOD/HCV C100-3 protein based HCV-EIA. In FIG. 2-1 a well-characterized HCV antibody positive control at various serum dilutions was used as the test sample. In FIG. 2-2 a panel of serum specimens derived from serial bleedings of a single individual spanning a period of sero-conversion to anti-HCV reactivity were used as samples.

FIGS. 3-1 and 3-2 depict the frequency distribution of the HCV-EIA positivity, using Peptide IIG, represented by the signal to cutoff ratios obtained with 264 normal serum and 264 normal plasma specimens from commercial sources. The mean s/c ratios for the negative (n=250) and screened out positive (i.e. n=14) serum specimens are 0.034 and 7.202 respectively; and for the negative (n=255) and positive (n=9) normal plasma specimens the mean s/c ratios are 0.084 and 7.089 respectively.

FIG. 4 is a histogram depicting the immunoreactivities of Peptide IIG with sera from individuals: (a) positive for HBsAg, (n=50); (b) positive for antibodies to HBc protein, (n=39); (c) with elevated (>100 I.U./L) alanine aminotransferase (ALT) enzyme activity, (n=174); (d) positive for antibodies to retroviruses HIV-1 (n=100), HIV-2 (n=10), HTLV-I/II (n=14); all asymptomatic, (total n=124); (e) with AIDS, ARC (N=200) or ATL (n=170) disease, (total n=270); and (f) with autoimmune disease (n=20).

FIG. 7-1 provides a study of serum samples collected over a ten year period of time from a NANBH patient who sero-converted after receiving HCV infected blood. The samples were tested by two EIA formats designated as A (coated with Peptides IIF and IIID at 5 ug/mL each) and B (coated with Peptides IIF, IIID and V at 5 ug/mL each) for comparison. The serum samples were provided by Dr. H. Alter of NIH.

FIG. 7-2 provides a kinetic study with serum samples, kindly provided by Dr. C. Stevens of New York Blood Center, from a hemodialysis patient who sero-converted and contracted NANBH. These were tested by EIA format B (coated with peptides IIF, IIID and V at 5 ug/mL each).

FIG. 7-3 provides a second kinetic study with serum samples, kindly provided by Dr. D. Bradley of Center for Disease Control, from a chimpanzee which sero-converted after being inoculated with a well-characterized strain of HCV and contracted NANBH, also tested by EIA format B.

FIGS. 8-1 and 8-2 depict the signal/cutoff ratio frequency distribution of both negative and positive serum specimens by a HCV-EIA format B. The results were obtained using 2035 low risk random blood donor specimens screen tested in a blood bank setting.

FIGS. 11-1, and 11-2 show the amino acid sequences of an immunodominant region of the postulated HCV structural (core or nucleocapsid) protein and precisely delineates the amino acid residues that contribute to the immunoreactivities of these HCV peptides with four representative HCV antibody positive sera (Samples 1-4). The immunoreactivities were measured as absorbance at 492 nm by an EIA procedure.

FIG. 12-1, 12-2, and 12-3 are histograms depicting the frequency distribution of HCV positivity in 221 sera from individuals: (a) with AIDS, ARC (n=63); (b) positive for HBsAg, (n=50); (c) positive for antibodies to HBc protein, (n=22); (d) with elevated (>100 I.U./L) alanine aminotransferase (ALT) enzyme activity, (n=86) tested using three HCV EIA formats using Peptides IIH, V and VIIIE at 5, 3, and 2 ug/mL respectively (Format C); Peptides VIIIE, and IXD at 2 and 2 ug/mL each (Format D), and Peptides IIH and V at 5 and 3 ug/mL each (Format A).

FIGS. 13-1, 13-2, 13-3, 13-4, 13-5, and 13-6 depict the signal to cutoff ratio frequency distribution of HCV positivity in low risk random donor specimens using three HCV-EIA Formats, A (13-1 and 13-2), C (13-3 and 13-4), and D (13-5 and 13-6). The results were screen tested in a blood bank setting.

FIG. 14-1 provides a study of serum samples collected over a ten year period of time from a NANBH patient who sero-converted after receiving HCV infected blood. The samples were tested by a third EIA format designated as C (coated with Peptides IIH, V, and VIIIE at 5, 3 and 2 ug/mL respectively) in comparison to two other EIA formats (designated as A and B.)

FIG. 14-2 provides another kinetic study with serum samples, kindly provided by Dr. D. Bradley of Center for Diseases Control, from a chimpanzee which sero-converted after being inoculated with a well-characterized strain of HCV and contracted NANBH. These samples were tested by the HCV EIA Format C, in comparison to a RIA using rDNA based HCV C-100 protein as the antigen. The ALT levels are also indicated with each bleed as a reference parameter.

FIGS. 15-1 and 15-2 both provide a side-by side data comparison via x-y plots with samples from hemodialysis patients, kindly provided by investigators at the Japanese National Institute of Health. The results were obtained by using the peptide based HCV EIA Format C (coated with peptides derived from both the structural and non-structural proteins containing IIH, V and VIIIE at 5, 3, and 2 ug/mL respectively), HCV EIA Format A (coated with peptides derived from the non-structural protein region containing IIH and V at 5 and 3 ug/mL respectively), and the recombinant HCV C-100 protein based EIA.

Figure 1:
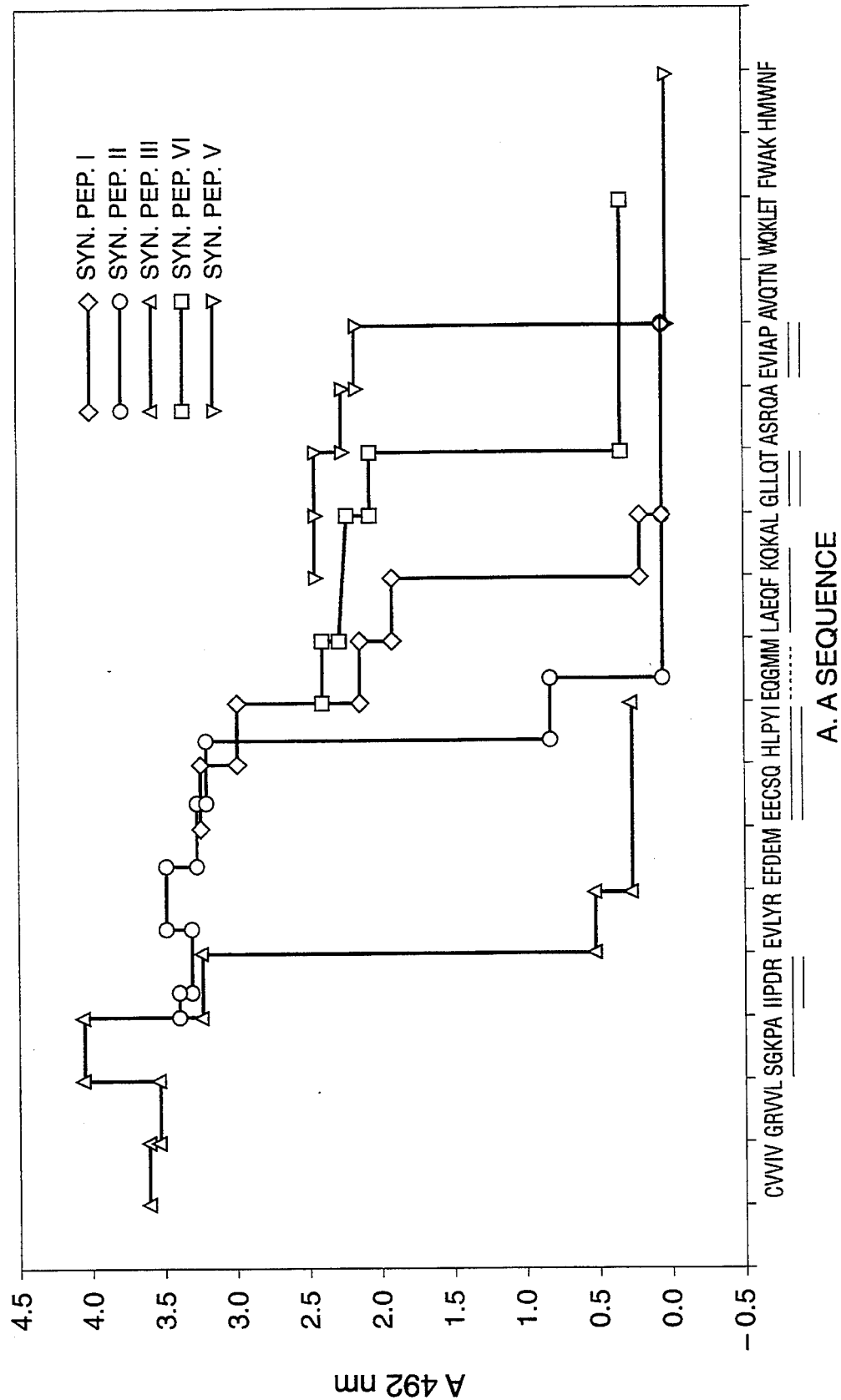
FIGS. 1-1, 1-2, 1-3 and 1-4 show the amino acid sequences of the immunodominant region of a HCV non structural protein and precisely delineates the amino acid residues (underlined to show—marginal, ▬moderate, and ▬strong) that contribute to the immunoreactivities of these HCV peptides with four representative HCV antibody positive sera. The immunoreactivities were measured as absorbance at 492 nm by an EIA procedure.

The amino acids in the drawings and tables are abbreviated using the art accepted single letter codes as follows:

| | | |
|---|---|---|
| A = | Ala = | alanine, |
| R = | Arg = | arginine, |
| D = | Asp = | aspartic acid, |
| N = | Asn = | asparagine, |
| Q = | Gln = | glutamine, |
| E = | Glu = | glutamic acid, |
| L = | Leu = | leucine, |
| K = | Lys = | lysine, |
| H = | His = | histidine, |
| T = | Thr = | threonine, |
| G = | Gly = | glycine, |
| I = | Ile = | isoleucine, |
| F = | Phe = | phenylalanine, |
| S = | Ser = | serine, |
| W = | Trp = | tryptophan, |
| Y = | Tyr = | tyrosine, |
| V = | Val = | valine, |
| C = | Cys = | cysteine, |
| P = | Pro = | proline, |
| M = | Met = | methionine |

DETAILED DESCRIPTION OF THE INVENTION

In accordance with the present invention, three peptides and their segments have been chemically synthesized for the detection of antibodies to HCV in body fluids, the diagnosis of NANBH, and for the vaccination of healthy mammals by stimulating the production of antibodies to HCV. These peptides are arranged in the following sequences:

Glu—Glu—Cys—Ser—Gln—His—Leu—Pro—Tyr—Ile—Glu—Gln— (i)
Gly—Met—Met—Leu—Ala—Glu—Gln—Phe—Lys—Gln—Lys—Ala—
Leu—Gly—Leu—Leu—Gln—Thr—Ala—Ser—Arg—Gln—Ala—Glu—
Val—Ile—Ala—Pro—X  (I)

Ile—Ile—Pro—Asp—Arg—Glu—Val—Leu—Tyr—Arg—Glu—Phe— (ii)
Asp—Glu—Met—Glu—Glu—Cys—Ser—Gln—His—Leu—Pro—Tyr—
Ile—Glu—Gln—Gly—Met—Met—Leu—Ala—Glu—Gln—Phe—Lys—
Gln—Lys—Ala—Leu—Gly—Leu—X  (II)

Ser—Gly—Lys—Pro—Ala—Ile—Ile—Pro—Asp—Arg—Glu—Val— (iii)
Leu—Tyr—Arg—Glu—Phe—Asp—Glu—Met—Glu—Glu—Cys—Ser—
Gln—His—Leu—Pro—Tyr—Ile—Glu—Gln—Gly—Met—Met—Leu—
Ala—Glu—Gln—Phe—Lys—Gln—Lys—Ala—Leu—Gly—Leu—X  (IIH)

Cys—Val—Val—Ile—Val—Gly—Arg—Val—Val—Leu—Ser—Gly— (iv)
Lys—Pro—Ala—Ile—Ile—Pro—Asp—Arg—Glu—Val—Leu—Tyr—
Arg—Glu—Phe—Asp—Glu—Met—Glu—Glu—Cys—Ser—Gln—His—
Leu—Pro—Tyr—Ile—X  (III)

Ser—Gly—Lys—Pro—Ala—Ile—Ile—Pro—Asp—Arg—Glu—Val— (v)
Leu—Tyr—Arg—Glu—Phe—Asp—Glu—Met—Glu—Glu—Cys—Ser—
Gln—His—Leu—Pro—Tyr—Ile—Glu—Gln—Gly—Met—Met—Leu—
Ala—Glu—Gln—Phe—X  (IV)

-continued

Lys—Gln—Lys—Ala—Leu—Gly—Leu—Leu—Gln—Thr—Ala—Ser— (vi)
Arg—Gln—Ala—Glu—Val—Ile—Ala—Pro—Ala—Val—Gln—Thr—
Asn—Trp—Gln—Lys—Leu—Glu—Thr—Phe—Trp—Ala—Lys—His—
Met—Trp—Asn—Phe—X (V)

Glu—Gln—Gly—Met—Met—Leu—Ala—Glu—Gln—Phe—Lys—Gln— (vii)
Lys—Ala—Leu—Gly—Leu—Leu—Gln—Thr—Ala—Ser—Arg—Gln—
Ala—Glu—Val—Ile—Ala—Pro—Ala—Val—Gln—Thr—Asn—Trp—
Gln—Lys—Leu—Glu—Thr—X (VI)

Pro—Gly—Ala—Leu—Val—Val—Gly—Val—Val—Cys—Ala—Ala— (viii)
Ile—Leu—Arg—Arg—His—Val—Gly—Pro—Gly—Glu—Gly—Ala—
Val—Gln—Trp—Met—Asn—Arg—Leu—Ile—Ala—Phe—Ala—Ser—
Arg—Gly—Asn—His—Val—Ser—Pro—X (VII)

Ser—Thr—Ile—Pro—Lys—Pro—Gln—Arg—Lys—Thr—Lys—Arg— (ix)
Asn—Thr—Asn—Arg—Arg—Pro—Gln—Asp—Val—Lys—Phe—Pro—
Gly—Gly—Gly—Gln—Ile—Val—Gly—Gly—Val—Tyr—Leu—Leu—
Pro—Arg—Arg—Gly—Pro—Arg—Leu—Gly—Val—Arg—Ala—Thr—
Arg—Lys—Thr—Ser—Glu—Arg—Ser—Gln—Pro—Arg—Gly—Arg—
Arg—X, and (VIII)

Gly—Arg—Arg—Gln—Pro—Ile—Pro—Lys—Val—Arg—Arg—Pro— (x)
Glu—Gly—Arg—Thr—Trp—Ala—Gln—Pro—Gly—Tyr—Pro—Trp—
Pro—Leu—Tyr—Gly—Asn—Glu—Gly—Cys—Gly—Trp—Ala—Gly—
Trp—Leu—Leu—Ser—Pro—Arg—Gly—Ser—Arg—Pro—Ser—Trp—
Gly—Pro—Thr—Asp—Pro—Arg—Arg—Arg—Ser—Arg—Asn—Leu—
Gly—X (IX)

wherein X is —OH or —NH$_2$.

These peptides may comprise combinations or segments, i.e. longer or shorter peptide chains by having more amino acids added to the terminal amino acids, or by amino acids removed from either terminal end.

These peptides may also comprise analogues to accommodate strain-to-strain variations among different isolates of HCV. HCV is indicated to have frequent mutations. Therefore, it is expected that variant strains, such as J-1 and J-4 (see reference #27), exist. Adjustments for conservative substitutions and selection among the alternatives where non-conservative substitutions are involved, may be made in the prescribed sequences. It is expected that as long as the peptide's immunoreactivity recognizable by the antibodies to HCV is preserved, analogues of the synthetic peptide may also comprise substitutions, insertions and/or deletions of the recited amino acids of the above sequence.

These peptides may also comprise conjugates, i.e., they may be coupled to carrier proteins such as bovine serum albumin (BSA) or human serum albumin (HSA). Furthermore, these peptides may comprise polymers, i.e., they may be synthesized on a polymeric resin, such as a branching octameric lysine resin.

The amino acid sequences of the polypeptides useful as test reagents for the detection of antibodies to HCV in body fluids and diagnosis of NANBH are selected to correspond to a partial segment of the amino acid sequence of the HCV proteins: a non-structural protein designated as HCV C-100(18), and a structural protein such as the core (nucleocapsid) protein (27).

In selecting regions of the HCV protein for epitope analysis, peptides in the 40mer size range with amino acid sequences covering the complete HCV C-100 protein and the postulated core protein were synthesized. These were tested for their immunoreactivity with serum from a patient positively diagnosed with HCV infection. Six overlapping peptides from the HCV C-100 protein region designated as I, II, III, IV, V and VI and two adjacent peptides form the postulated core protein region designated as VIII and IX were identified to have specific immunoreactivity with the positive HCV serum. Another peptide VII and its fragments, C-terminal to this immunodominant region, was also found to have moderate immunoreactivity with a sub population of HCV positive sera. See Example 12. Peptide IIH, another analogue of Peptide II, with five additional amino acids to the N-terminus has been found to be highly immunogenic and contains an additional epitope recognizable by antibodies in sera from patients with acute phase NANBHV infection (with elevated ALT levels). The amino acid sequences of the peptides are as follows:

Glu—Glu—Cys—Ser—Gln—His—Leu—Pro—Tyr—Ile—Glu—Gln— (i)
Gly—Met—Met—Leu—Ala—Glu—Gln—Phe—Lys—Gln—Lys—Ala—
Leu—Gly—Leu—Leu—Gln—Thr—Ala—Ser—Arg—Gln—Ala—Glu—
Val—Ile—Ala—Pro—X (I)

Ile—Ile—Pro—Asp—Arg—Glu—Val—Leu—Tyr—Arg—Glu—Phe— (ii)
Asp—Glu—Met—Glu—Glu—Cys—Ser—Gln—His—Leu—Pro—Tyr—
Ile—Glu—Gln—Gly—Met—Met—Leu—Ala—Glu—Gln—Phe—Lys—
Gln—Lys—Ala—Leu—Gly—Leu—X (II)

Ser—Gly—Lys—Pro—Ala—Ile—Ile—Pro—Asp—Arg—Glu—Val— (iii)
Leu—Tyr—Arg—Glu—Phe—Asp—Glu—Met—Glu—Glu—Cys—Ser—
Gln—His—Leu—Pro—Tyr—Ile—Glu—Gln—Gly—Met—Met—Leu—
Ala—Glu—Gln—Phe—Lys—Gln—Lys—Ala—Leu—Gly—Leu—X (IIH)

Cys—Val—Val—Ile—Val—Gly—Arg—Val—Val—Leu—Ser—Gly— (iv)
Lys—Pro—Ala—Ile—Ile—Pro—Asp—Arg—Glu—Val—Leu—Tyr—
Arg—Glu—Phe—Asp—Glu—Met—Glu—Glu—Cys—Ser—Gln—His—
Leu—Pro—Tyr—Ile—X (III)

-continued

Ser—Gly—Lys—Pro—Ala—Ile—Ile—Pro—Asp—Arg—Glu—Val— (v)
Leu—Tyr—Arg—Glu—Phe—Asp—Glu—Met—Glu—Glu—Cys—Ser—
Gln—His—Leu—Pro—Tyr—Ile—Glu—Gln—Gly—Met—Met—Leu—
Ala—Glu—Gln—Phe—X    (IV)

Lys—Gln—Lys—Ala—Leu—Gly—Leu—Leu—Gln—Thr—Ala—Ser— (vi)
Arg—Gln—Ala—Glu—Val—Ile—Ala—Pro—Ala—Val—Gln—Thr—
Asn—Trp—Gln—Lys—Leu—Glu—Thr—Phe—Trp—Ala—Lys—His—
Met—Trp—Asn—Phe—X    (V)

Glu—Gln—Gly—Met—Met—Leu—Ala—Glu—Gln—Phe—Lys—Gln— (vii)
Lys—Ala—Leu—Gly—Leu—Leu—Gln—Thr—Ala—Ser—Arg—Gln—
Ala—Glu—Val—Ile—Ala—Pro—Ala—Val—Gln—Thr—Asn—Trp—
Gln—Lys—Leu—Glu—Thr—X    (VI)

Pro—Gly—Ala—Leu—Val—Val—Gly—Val—Val—Cys—Ala—Ala— (viii)
Ile—Leu—Arg—Arg—His—Val—Gly—Pro—Gly—Glu—Gly—Ala—
Val—Gln—Trp—Met—Asn—Arg—Leu—Ile—Ala—Phe—Ala—Ser—
Arg—Gly—Asn—His—Val—Ser—Pro—X    (VII)

Ser—Thr—Ile—Pro—Lys—Pro—Gln—Arg—Lys—Thr—Lys—Arg— (ix)
Asn—Thr—Asn—Arg—Arg—Pro—Gln—Asp—Val—Lys—Phe—Pro—
Gly—Gly—Gly—Gln—Ile—Val—Gly—Gly—Val—Tyr—Leu—Leu—
Pro—Arg—Arg—Gly—Pro—Arg—Leu—Gly—Val—Arg—Ala—Thr—
Arg—Lys—Thr—Ser—Glu—Arg—Ser—Gln—Pro—Arg—Gly—Arg—
Arg—X, and    (VIII)

Gly—Arg—Arg—Gln—Pro—Ile—Pro—Lys—Val—Arg—Arg—Pro— (x)
Glu—Gly—Arg—Thr—Trp—Ala—Gln—Pro—Gly—Tyr—Pro—Trp—
Pro—Leu—Tyr—Gly—Asn—Glu—Gly—Cys—Gly—Trp—Ala—Gly—
Trp—Leu—Leu—Ser—Pro—Arg—Gly—Ser—Arg—Pro—Ser—Trp—
Gly—Pro—Thr—Asp—Pro—Arg—Arg—Arg—Ser—Arg—Asn—Leu—
Gly—X    (IX)

The six peptides I, II, III, IV, V and VI span a region of 90 amino acids:

Cys—Val—Val—Ile—Val—Gly—Arg—Val—Val—Leu—Ser—Gly—Lys—Pro—Ala—Ile—
Ile—Pro—Asp—Arg—Glu—Val—Leu—Tyr—Arg—Glu—Phe—Asp—Glu—Met—Glu—Glu—
Cys—Ser—Gln—His—Leu—Pro—Tyr—Ile—Glu—Gln—Gly—Met—Met—Leu—Ala—Glu—
Gln—Phe—Lys—Gln—Lys—Ala—Leu—Gly—Leu—Leu—Gln—Thr—Ala—Ser—Arg—Gln—
Ala—Glu—Val—Ile—Ala—Pro—Ala—Val—Gln—Thr—Asn—Trp—Gln—Lys—Leu—Glu—
Thr—Phe—Trp—Ala—Lys—His—Met—Trp—Asn—Phe and were found to have specific immunoreactivity with the positive control serum. Table 1 shows the amino acid sequence of this immunodominant region of the HCV protein, and presents the amino acrid sequence of the six chemically synthesized peptides, designated as I to VI and segments (A to H) thereof.

Another two peptides (VIII and IX) spanning a region of 119 amino acids located inside the 5' terminal of the postulated HCV core protein:

Ser—Thr—Ile—Pro—Lys—Pro—Gln—Arg—Lys—Thr—Lys—Arg—Asn—Thr—Asn—Arg—
Arg—Pro—Gln—Asp—Val—Lys—Phe—Pro—Gly—Gly—Gly—Gln—Ile—Val—Gly—Gly—
Val—Tyr—Leu—Leu—Pro—Arg—Arg—Gly—Pro—Arg—Leu—Gly—Val—Arg—Ala—Thr—
Arg—Lys—Thr—Ser—Glu—Arg—Ser—Gln—Pro—Arg—Gly—Arg—Arg—Gln—Pro—Ile—
Pro—Lys—Val—Arg—Arg—Pro—Glu—Gly—Arg—Thr—Trp—Ala—Gln—Pro—Gly—Tyr—
Pro—Trp—Pro—Leu—Tyr—Gly—Asn—Glu—Gly—Cys—Gly—Trp—Ala—Gly—Trp—Leu—
Leu—Ser—Pro—Arg—Gly—Ser—Arg—Pro—Ser—Trp—Gly—Pro—Thr—Asp—Pro—Arg—
Arg—Arg—Ser—Arg—Asn—Leu—Gly—X were found to have specific immunoreactivity with a representative panel of well-characterized HCV antibody positive sera.

Table 7 shows the amino acid sequence of this immunodominant region of the postulated HCV core protein, and presents the amino acid sequence of the ten chemically synthesized[peptides. They were designated, as Peptides VIII and IX with segments (A to D) thereof. Each of these peptides was coated at 5 ug/mL in a 10 mM sodium bicarbonate buffer (pH 9.5) onto polystyrene microwell plates and tested in a three step 45 minute enzyme immunoassay CHARACTERIZATION OF THE IMMUNODOMINANT REGION OF THE HCV SOD-C100 FUSION POLYPEPTIDE:

| | CV,VIVGR,VVLSG,KPAII,PDPEV,LYREF,DEMEE,CSQHL,PYIEQ,GMMLA,EQFKQ.KALGL,LQTAS,RQAEV,IAPAV,QTNWQ,KLETF.WAKHM,WNF | RELATIVE (%) IMMUNOREACTIVITY |
|---|---|---|
| IA | GL.LQTAS,RQAEV,IAP | 3.0 |
| IB | KQ,KALGL,LQTAS.RQAEV,IAP | 10.3 |
| IC | MLA,EQFKQ,KALGL,LQTAS,RQAEV,IAP | 23.9 |
| ID | EQ,GMMLA.EQFKQ,KALGL.LQTAS,RQAEV,IAP | 24.6 |
| IE | HL,PYIEQ,GMMLA,EQFKQ,KALGL,LQTAS,RQAEV,IAP | 38.2 |
| IF | EE,CSQHL,PYIEQ.GMMLA,EQFKQ,KALGL,LQTAS,RQAEV,IAP | 45.6 |
| IIA | GMMLA,EQFKQ,KALGL | 3.1 |
| IIB | PYIEQ,GMMLA,EQFKQ,KALGL | 24.3 |
| IIC | CSQHL,PYIEQ,GMMLA,EQFKQ,KALGL | 41.7 |
| IID | DEMEE,CSQHL,PYIEQ,GMMLA,EQFKQ,KALGL | 44.9 |
| IIE | LYREF,DEMEE,CSQHL,PYIEQ,GMMLA,EQFKQ,KALGL | 57 |
| IIF | PDREV,LYREF,DEMEE,CSQHL,PYIEQ,GMMLA,EQFKQ,KALGL | 99 |
| IIG | II,PDREV,LYREF,DEMEE,CSQHL,PYIEQ,GMMLA,EQFKQ,KALGL | 93.2 |
| IIH | SG,KPAII,PDREV,LYREF,DEMEE,CSQHL,PYIEQ,GMMLA,EQFKQ,KALGL | 101 |
| IIIA | EF,DEMEE,CSQHL.PYI | 4.9 |
| IIIB | EV,LYREF,DEMEE,CSQHL,PYI | 26.3 |
| IIIC | II,PDREV,LYREF,DEMEE,CSQHL,PYI | 85 |
| IIID | SG,KPAII,PDREV,LYREF,DEMEE,CSQHL,PYI | 100 |
| IIIE | GR,VVLSG,KPAII,PDREV,LYREF,DEMEE,CSQHL,PYI | 99 |
| IIIF | CV,VIVGR,VVLSG,KPAII,PDREV,LYREF,DEMEE,CSQHL,PYI | 95 |
| IV | SG,KPAII,PDREV,LYREF,DEMEE,CSQHL,PYIEQ,GMMLA,EQF | 93.8 |
| VIA | AS,RQAEV,IAPAV,QTNWQ,KLET | 3.9 |
| VIB | GL,LQTAS,RQAEV,IAPAV,QTNWQ,KLET | 43.6 |
| VIC | KQ,KALGL,LQTAS,RQAEV,IAPAV,QTNWQ,KLET | 44.0 |
| VID | LA,EQFKQ,KALGL,LQTAS,RQAEV,IAPAV,QTNWQ,KLET | 46.0 |
| VIE | EQ,GMMLA,EQFKQ,KALGL,LQTAS,RQAEV,IAPAV,QTNWQ,KLET | 54.8 |
| VA | AV,QTNWQ,KLETF,WAKHM,WNF | 1.3 |
| VB | EV,IAPAV,QTNWQ,KLETF,WAKHM,WNF | 17.8 |
| VC | AS,RQAEV,IAPAV,QTNWQ,KLETF,WAKHM,WNF | 23.4 |
| VD | GL,LQTAS,RQAEV,IAPAV,QTNWQ,KLETF,WAKHM,WNF | 32.3 |
| V | KQ,KALGL,LQTAS,RQAEV,IAPAV,QTNWQ,KLETF,WAKHM,WNF | 93.9 |

The underlined amino acid residues exert ( ) marginal, ( ) moderate, or ( ) strong immunoreactivity

TABLE 7

Identification and characterization of An Immunodominant Region in HCV's Structural Proteins, based on the predicted amino acid sequence derived from the structural genes of to HCV genomes (27), by serological validation with a combination of synthetic peptides (VIIIA-E and IXA-E):

| | | |
|---|---|---|
| J-1 | STIP,KPQRK,TKRNT,NRRPQ,DVKFP,GGGQI,VGGVY,LLPRR,GPRLG,VRATR,KTSER,SQPRG, | |
| J-4 | - - N-,- - - - ,- - - - ,- - - - ,- - - - ,- - - -,- - - - ,- - - - ,- - - - ,- - - - ,- - - - ,- - - - , | |

| Peptide Code | | % Relat Immuno -react |
|---|---|---|
| VIIIE | STIP,KPQRK,TKRNT,NRRPQ,DVKFP,GGGQI,VGGVY,LLPRR,GPRLG,VRATR,KTSER,SQPRG, | 98.6 |
| VIIID | TKRNT,NRRPQ,DVKFP,GGGQI,VGGVY,LLPRR,GPRLG,VRATR,KTSER,SQPRG, | 84.1 |
| VIIIC | DVKFP,GGGQI,VGGVY,LLPRR,GPRLG,VRATR,KTSER,SQPRG, | 70.2 |
| VIIIB | VGGVY,LLPRR,GPRLG,VRATR,KTSER,SQPRG, | 54.8 |
| VIIIA | GPRLG,VRATR,KTSER,SQPRG, | 27.5 |
| J-1 | RRQPI,PKVRR,PEGRT,WAQPG,YPWPL,YGNEG,CGWAG,WLLSP,RGSRP,SWGPT,DPRRR,SRNLG | |
| J-4 | W- - - -,- - A- - ,- - - - A,- - - - ,- - - - -,- - - - ,L - - - ,- - - - ,- - - - ,- - - - ,- - - - ,- - - - | |

| Peptide Code | | % Relat Immuno -react |
|---|---|---|
| VIIIE | RR | |
| VIIID | RR | |
| VIIIC | RR | |
| VIIIB | RR | |
| VIIIA | RR | |
| IXE | G,RRQPI,PKVRR,PEGRT,WAQPG,YPWPL,YGNEG,CGWAG,WLLSP,RGSRP,SWGPT,DPRRR,SRNLG | 49.5 |
| IXD | I,PKVRR,PEGRT,WAQPG,YPWPL,YGNEG,CGWAG,WLLSP,RGSRP,SWGPT,DPRRR,SRNLG | 58.1 |
| IXC | T,WAQPG,YPWPL,YGNEG,CGWAG,WLLSP,RGSRP,SWGPT,DPRRR,SRNLG | 57.1 |
| IXB | L,YGNEG,CGWAG,WLLSP,RGSRP,SWGPT,DPRRR,SRNLG | 48.4 |
| IXA | WAG,WLLSP,RGSRP,SWGPT,DPRRR,SRNLG | 23.8 | procedure, described hereinbelow, with a panel of HCV antibody positive sera, each selected as representative of a particular clinical population, at various serum dilutions. Calculations based on the overall EIA absorbance of all positive sera yielded an array of immunoreactivity indices represented as % relative immunoreactivity for each of the synthetic HCV peptides.

amino acid residues (as underlined), each in a prescribed sequence, that are involved in or relevant to the antigenic configuration of the HCV peptides. Two peptides, designated as VIIIE and IXD being 61 mer and 56 mer in size are respectively located within the HCV structural core protein region with the following amino acid sequences:

Ser—Thr—Ile—Pro—Lys—Pro—Gln—Arg—Lys—Thr—Lys—Arg—
Thr—Asn—Arg—Arg—Pro—Gln—Asp—Val—Lys—Phe—Pro—Gly—Gly—
Gly—Gln—Ile—Val—Gly—Gly—Val—Tyr—Leu—Leu—Pro—Arg—Arg—
Gly—Pro—Arg—Leu—Gly—Val—Arg—Ala—Thr—Arg—Lys—Thr—Ser—
Glu—Arg—Ser—Gln—Pro—Arg—Gly—Arg—Arg—X    (VIIIE)

—Ile—Pro—Lys—Val—Arg—Arg—Pro—Glu—
Gly—Arg—Thr—Trp—Ala—Gln—Pro—Gly—Tyr—Pro—Trp—Pro—Leu—
Tyr—Gly—Asn—Glu—Gly—Cys—Gly—Trp—Ala—Gly—Trp—Leu—Leu—
Ser—Pro—Arg—Gly—Ser—Arg—Pro—Ser—Trp—Gly—Pro—Thr—Asp—
Pro—Arg—Arg—Arg—Ser—Arg—Asn—Leu—Gly—X    (IXD)

Three peptides, designated as IIF, IIH and IIID, being 40 mer, 47 mer and 30 mer in size, with the following amino acid sequence respectively:

Peptides XIIIE and IXD were also found to have the highest reactivity in this region.

Assays for antibodies to HCV based upon chemically

Pro—Asp—Arg—Glu—Val—Leu—Tyr—Arg—Glu—Phe—Asp—Glu—
Met—Glu—Glu—Cys—Ser—Gln—His—Leu—Pro—Tyr—Ile—Glu—
Gln—Gly—Met—Met—Leu—Ala—Glu—Gln—Phe—Lys—Gln—Lys—
Ala—Leu—Gly—Leu    (IIF)

Ser—Gly—Lys—Pro—Ala—Ile—Ile—Pro—Asp—Arg—Glu—Val—
Leu—Tyr—Arg—Glu—Phe—Asp—Glu—Met—Glu—Glu—Cys—Ser—
Gln—His—Leu—Pro—Tyr—Ile—Glu—Gln—Gly—Met—Met—Leu—
Ala—Glu—Gln—Phe—Lys—Gln—Lys—Ala—Leu—Gly—Leu    (IIH)

and

Ser—Gly—Lys—Pro—Ala—Ile—Ile—Pro—Asp—Arg—Glu—Val—
Leu—Tyr—Arg—Glu—Phe—Asp—Glu—Met—Glu—Glu—Cys—Ser—
Gln—His—Leu—Pro—Tyr—Ile    (IIID)

were found to have the highest immunoreactivity with the sera panel. The relative (%) immunoreactivity for each of the 40 HCV peptides listed in Tables 1 and 7, as a result of this extensive epitope mapping study, provides a basis for the delineation of several clusters of synthesized peptides show several advantages over assays utilizing biologic based immunoadsorbents. The peptides can easily be synthesized in gram quantities by using automated solid-phase methods, thus providing a reproducible antigen of high integrity with consistent yields. The presence of other antigens from biological systems precludes such reproducibility. More importantly, non-specific reactivities seen in uninfected individuals are likely to be due to the heterogeneity of the preparations used for assay. This is particularly true for assays using biologically based immunoadsorbents. In these processes, the host antigens are frequently co-purified with the desired vital protein(s). Antibodies to these contaminating antigens are frequently found in normal individuals, thus resulting in false-positive results.

The assay of the present invention clearly minimizes such false-positive reactions as encountered in the other assay systems and, at the same time, shows a high sensitivity to truly positive sera by the substantially increased signal-to-noise ratio. This increased signal-to-noise ratio probably resulted from the purity of the immunoadsorbent. The assay of the present invention is also highly specific, in that the mean S/C: ratios for HCV carriers are about 80–200 times the mean S/C of those of the non-infected individuals. For a representative example, see FIGS. 3-1 and 3-2.

The peptides useful as solid phase immunoadsorbents for the detection of antibodies to HCV were synthesized by the "classical" Merrifield method of solid phase peptide synthesis using side chain protected t-Boc-amino acids to correspond to the following amino acid sequences:

Glu—Glu—Cys—Ser—Gln—His—Leu—Pro—Tyr—Ile—Glu—Gln— (i)
Gly—Met—Met—Leu—Ala—Glu—Gln—Phe—Lys—Gln—Lys—Ala—
Leu—Gly—Leu—Leu—Gln—Thr—Ala—Ser—Arg—Gln—Ala—Glu—
Val—Ile—Ala—Pro—X     (I)

Ile—Ile—Pro—Asp—Arg—Glu—Val—Leu—Tyr—Arg—Glu—Phe— (ii)
Asp—Glu—Met—Glu—Glu—Cys—Ser—Gln—His—Leu—Pro—Tyr—
Ile—Glu—Gln—Gly—Met—Met—Leu—Ala—Glu—Gln—Phe—Lys—
Gln—Lys—Ala—Leu—Gly—Leu—X     (II)

Ser—Gly—Lys—Pro—Ala—Ile—Ile—Pro—Asp—Arg—Glu—Val— (iii)
Leu—Tyr—Arg—Glu—Phe—Asp—Glu—Met—Glu—Glu—Cys—Ser—
Gln—His—Leu—Pro—Tyr—Ile—Glu—Gln—Gly—Met—Met—Leu—
Ala—Glu—Gln—Phe—Lys—Gln—Lys—Ala—Leu—Gly—Leu—X     (IIH)

Cys—Val—Val—Ile—Val—Gly—Arg—Val—Val—Leu—Ser—Gly— (iv)
Lys—Pro—Ala—Ile—Ile—Pro—Asp—Arg—Glu—Val—Leu—Tyr—
Arg—Glu—Phe—Asp—Glu—Met—Glu—Glu—Cys—Ser—Gln—His—
Leu—Pro—Tyr—Ile—X     (III)

Ser—Gly—Lys—Pro—Ala—Ile—Ile—Pro—Asp—Arg—Glu—Val— (v)
Leu—Tyr—Arg—Glu—Phe—Asp—Glu—Met—Glu—Glu—Cys—Ser—
Gln—His—Leu—Pro—Tyr—Ile—Glu—Gln—Gly—Met—Met—Leu—
Ala—Glu—Gln—Phe—X     (IV)

Lys—Gln—Lys—Ala—Leu—Gly—Leu—Leu—Gln—Thr—Ala—Ser— (vi)
Arg—Gln—Ala—Glu—Val—Ile—Ala—Pro—Ala—Val—Gln—Thr—
Asn—Trp—Gln—Lys—Leu—Glu—Thr—Phe—Trp—Ala—Lys—His—
Met—Trp—Asn—Phe—X     (V)

Glu—Gln—Gly—Met—Met—Leu—Ala—Glu—Gln—Phe—Lys—Gln— (vii)
Lys—Ala—Leu—Gly—Leu—Leu—Gln—Thr—Ala—Ser—Arg—Gln—
Ala—Glu—Val—Ile—Ala—Pro—Ala—Val—Gln—Thr—Asn—Trp—
Gln—Lys—Leu—Glu—Thr—X     (VI)

Pro—Gly—Ala—Leu—Val—Val—Gly—Val—Val—Cys—Ala—Ala— (viii)
Ile—Leu—Arg—Arg—His—Val—Gly—Pro—Gly—Glu—Gly—Ala—
Val—Gln—Trp—Met—Asn—Arg—Leu—Ile—Ala—Phe—Ala—Ser—
Arg—Gly—Asn—His—Val—Ser—Pro—X     (VII)

Ser—Thr—Ile—Pro—Lys—Pro—Gln—Arg—Lys—Thr—Lys—Arg— (ix)
Asn—Thr—Asn—Arg—Arg—Pro—Gln—Asp—Val—Lys—Phe—Pro—
Gly—Gly—Gly—Gln—Ile—Val—Gly—Gly—Val—Tyr—Leu—Leu—
Pro—Arg—Arg—Gly—Pro—Arg—Leu—Gly—Val—Arg—Ala—Thr—
Arg—Lys—Thr—Ser—Glu—Arg—Ser—Gln—Pro—Arg—Gly—Arg—
Arg—X, and     (VIII)

Gly—Arg—Arg—Gln—Pro—Ile—Pro—Lys—Val—Arg—Arg—Pro— (x)
Glu—Gly—Arg—Tyr—Trp—Ala—Gln—Pro—Gly—Tyr—Pro—Trp—
Pro—Leu—Thr—Gly—Asn—Glu—Gly—Cys—Gly—Trp—Ala—Gly—
Trp—Leu—Leu—Ser—Pro—Arg—Gly—Ser—Ara—Pro—Ser—Trp—
Gly—Pro—Thr—Asp—Pro—Arg—Arg—Arg—Ser—Arg—Asn—Leu—
Gly—X     (IX)

wherein X is —NH$_2$.

Other analogues, segments and combinations of these peptides may be prepared by varying the amino acid sequences either by adding, subtracting, substituting, or deleting desired t-Boc-amino acid(s).

Following completion of assembly of the desired blocked peptide on the resin, the peptide-resin is treated with anhydrous hydrofluoric acid to cleave the peptide from the resin. Functional groups of amino acids which are blocked during synthesis by benzyl-derived blocking groups are also cleaved from the peptide simultaneously. The free peptide is then analyzed and purified by high performance liquid chromatography (HPLC) and characterized biochemically by amino acid analysis.

Longer peptides with more than about 50 amino acids may also be prepared conveniently using well known recombinant methods. The known nucleic acids codons for each of the amino acids in the peptide may be utilized and synthetic genes encoding such peptides constructed. The synthetic gene may be inserted into vector constructs by known techniques, cloned and transfected into host cells, such as E. coli, or yeast. The secreted polypeptide may then be processed and purified according to known procedures. The peptides synthesized according to the above described procedures are highly reactive with antibodies to HCV and can be used as a highly sensitive and specific immunoadsorbent for the detection of antibodies to HCV.

FIGS. 1-1, 1-2, 1-3 and 1-4 and FIGS. 11-1 and 11-2 show the amino acid sequences of the immunodominant regions of HCV proteins, both structural and non-structural, and precisely delineates, in the case of the non-structural protein HCV C-100 region, the underlined amino acid residues that contribute (—marginally, moderately, or—strongly) to the immunoreactivities, measured at A492 nm by a peptide based EIA procedure of these HCV peptides with four representative HCV antibody positive sera.

The peptide based EIA procedure used to measure the immunoreactivity of each peptide is as follows. 100 uL per well of each of the peptides was coated at 5 ug/mL in a pH 9.5 sodium bicarbonate buffer (10 mM) onto a polystyrene microwell plate and the microwell plate was incubated at 37° C. for about an hour, washed and dried. The test serum samples were diluted with PBS containing normal goat serum, gelatin and TWEEN 20. 200 uL of the test serum sample solution was added to each well and allowed to react for 15 mins. at 37° C. The wells were washed, enzyme labelled antibodies were used to bind the HCV-antibody-peptide complex, and the plate was incubated for another 15 min. A color developer, e.g. orthophenylenediamine (OPD), was then added. The reaction was stopped after 15 min by the addition of 50 uL 1.0M $H_2SO_4$, and the absorbance of the reaction mixture was read at 492 nm with an ELISA reader.

As demonstrated in FIG. 1-1, serum sample 1 has little reactivity with Peptide IA and IB. However, its reactivity with Peptide IC increases significantly, followed by a marginal increase with Peptide ID, and additional increases with Peptides IE and IF. This indicates that in the HCV Peptide I series, two clusters of amino acid residues, namely Leu-Ala-Glu-Gln-Phe (LAEQF) and His-Leu-Pro-Tyr-Ile (HLPYI), are contributing to the antigenic determinant(s) of the HCV Peptide I. Similarly, a cluster of residues namely Glu-Glu-Cys-Ser-Gln-His-Leu-Pro-Tyr-Ile (EECSQH-LPYI) is contributing to the immunoreactivity of the HCV Peptide II series; another cluster of residues namely Ser-Gly-Lys-Pro-Ala-Ile-Ile-Pro-Asp-Arg (SGKPAIIPDR) is contributing to the immunoreactivity of HCV Peptide III series and two clusters of residues, namely Gly-Leu-Leu-Gln- (GLLQT) and Glu-Val-Ile-Ala-Pro (EVIAP) are contributing to the immunoreactivity by HCV peptides IV and V series. As shown on the bottom of FIG. 1-1, a total of six spaced clusters of amino acid residues representing discontinuous epitopes in this immunodominant region of the HCV protein are identified as contributing to the specific HCV immunoreactivity with serum sample 1.

Figures 1, 2:
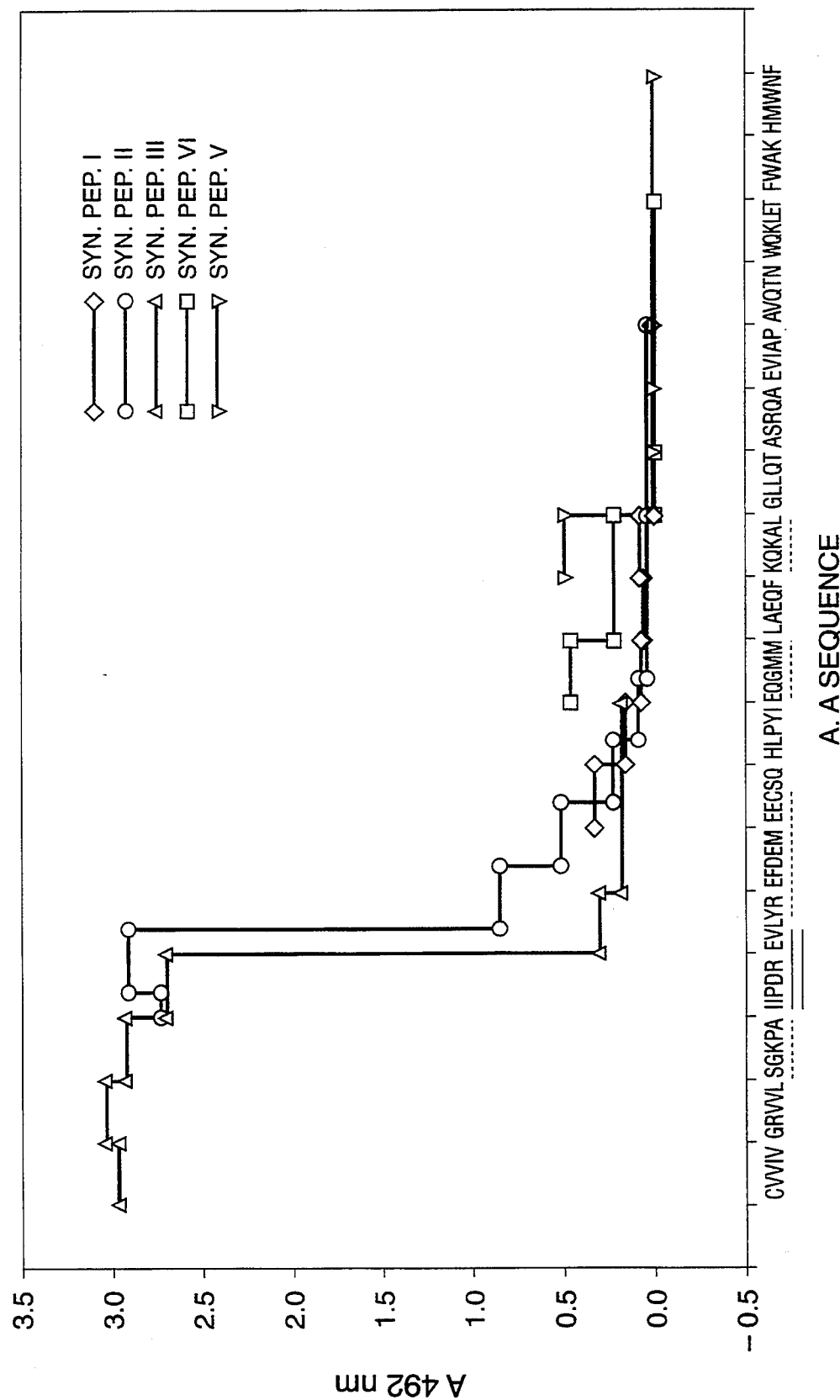

FIG. 1-2 illustrates an immunoreactivity profile for serum sample 2 when tested on a total of 31 overlapping peptides in the HCV Peptide I, II, III, IV, V and VI series. There is a clear difference between the immunoreactivity profiles of serum samples 1 and 2. The immunodominant epitope, as marked by residues Ser-Gly-Lys-Pro-Ala (SGKPA) and Ile-Pro-Pro-Asp-Arg-Glu-Val (IIPDREV,) is located towards the N-terminus of the region.

Figures 1, 2, 3:
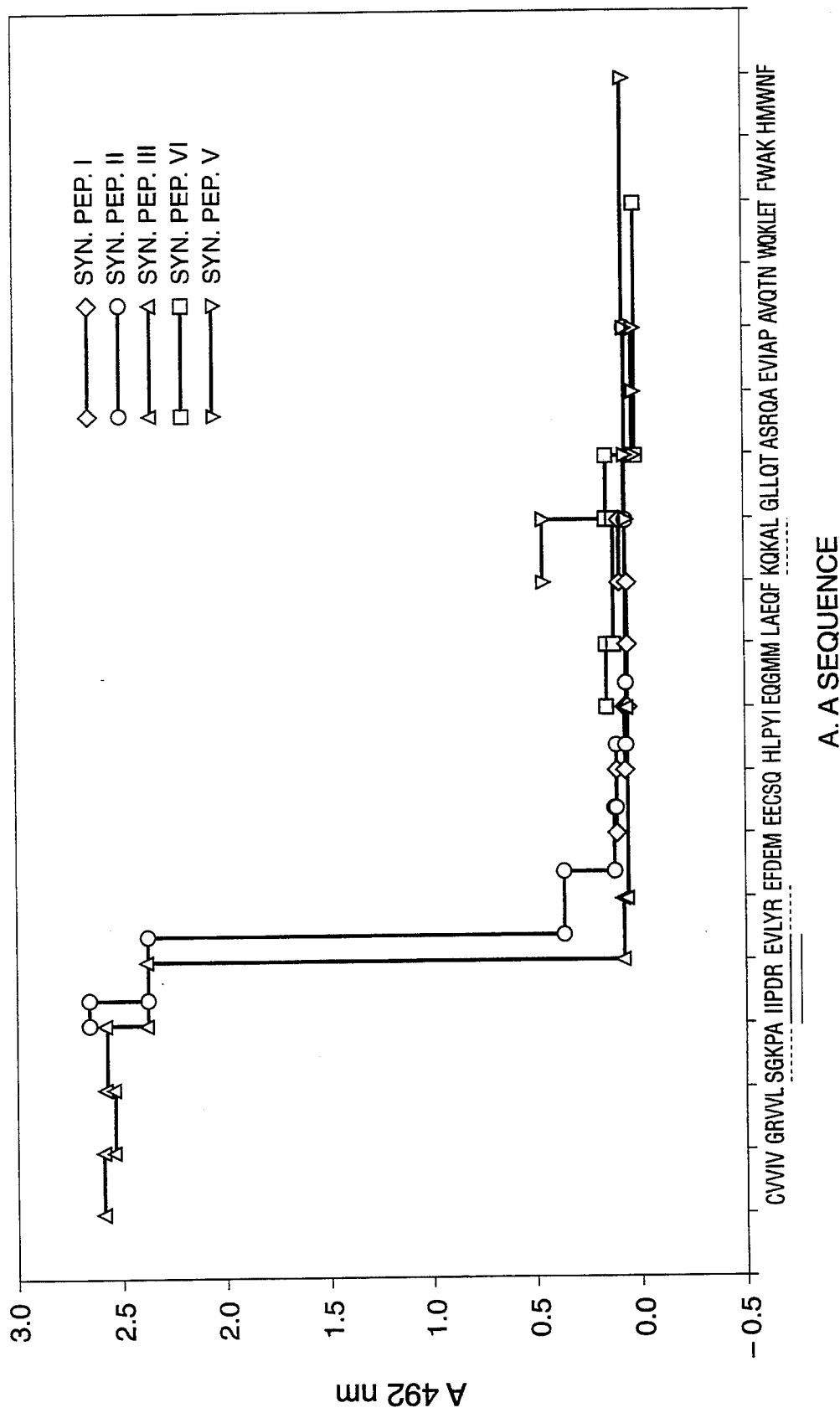

FIG. 1-3 illustrates an immunoreactivity profile for serum 3 when tested on the same 31 HCV peptide panel. Through this extensive epitope mapping analysis, serum sample 3 was found to have a similar immunoreactivity profile to that of serum sample 2.

FIG. 1-4 illustrates an immunoreactivity profile for serum sample 4 which differs significantly from that of sample 2 and 3, while maintaining some similarity to that of sample 1.

In summary, epitope mapping analysis conducted with a series of 31 overlapping peptides covering an immunodominant region of the HCV non-structural protein, which spans a total of 90 amino acid residues as illustrated in Table 1, and an immunodominant region of the HCV structural core protein, which spans a total of 119 amino acid residues as illustrated in Table 7, reveals a varying degree of immunoreactivity among different HCV antibody positive samples and these HCV peptides. Based on overall EIA absorbance readings obtained with a panel of eight HCV positive sera with each of these 31 HCV peptides (Table 2), a relative (%) immunoreactivity index is established for each of the peptides and several clusters of amino acid residues are identified as contributing strongly, as in the cases of Ile-Ile-Pro-Asp-Arg-Glu-Val-Leu-Tyr-Arg and Glu-Val-Ile-Ala-Pro; moderately, as in the cases of Ser-Gly-Lys-Pro-Ala, Glu-Val-Leu-Tyr-Arg-Glu-Phe, Cys-Ser-Gln-His-Leu-Pro-Tyr-Ile-Glu-Gln-Gly; and Leu-Ala-Glu-Gln-Phe-Lys-Gln; or marginally, as in the case of Lys-Gln-Lys-Ala-Leu, to the HCV immunoreactivity.

Similarly, the relative immunoreactivity of Peptide VIII and IX and their analogue-segments are presented in Table 7.

TABLE 2

| | HCV Peptide Segments | | | | | | | | | | | | | | | | | | |
|---|---|---|---|---|---|---|---|---|---|---|---|---|---|---|---|---|---|---|---|
| | I | | | | | | II | | | | | | | III | | | | | |
| Specimens | A | B | C | D | E | F | A | B | C | D | E | F | G | A | B | C | D | E | F |
| Blank | 0.041 | 0.041 | 0.041 | 0.041 | 0.041 | 0.041 | 0.041 | 0.040 | 0.040 | 0.041 | 0.041 | 0.041 | 0.044 | 0.040 | 0.046 | 0.040 | 0.045 | 0.040 | 0.043 |
| NRC | 0.047 | 0.050 | 0.049 | 0.049 | 0.052 | 0.055 | 0.045 | 0.044 | 0.048 | 0.046 | 0.048 | 0.088 | 0.074 | 0.044 | 0.048 | 0.061 | 0.073 | 0.071 | 0.070 |
| WRC | 0.040 | 0.048 | 0,077 | 0.084 | 0.155 | 0.221 | 0.040 | 0.042 | 0.220 | 0.153 | 0.241 | 0.399 | 0.365 | 0.046 | 0,043 | 0.192 | 0.243 | 0.269 | 0.222 |
| SRC | 0.049 | 0.055 | 0.330 | 0.383 | 0.828 | 1.175 | 0.043 | 0.093 | 1.188 | 0.963 | 1.279 | 1.832 | 1.672 | 0.046 | 0.074 | 1.081 | 1.260 | 1.379 | 1.127 |
| 1 | 0.066 | 0.218 | 1.925 | 2.151 | 2.994 | 3.247 | 0.075 | 0.838 | 3.219 | 3.282 | 3.494 | 3.316 | 3.395 | 0.289 | 0.527 | 3.245 | 4.057 | 3.545 | 3.613 |
| 2 | 0.054 | 0.095 | 0.080 | 0.093 | 0.171 | 0.337 | 0.066 | 0.103 | 0.243 | 0.536 | 0.872 | 2.929 | 2.746 | 0.191 | 0.316 | 2.715 | 2.941 | 3.053 | 2.984 |
| 3 | 0.062 | 0.089 | 0.062 | 0.064 | 0.068 | 0.108 | 0.065 | 0.058 | 0.121 | 0.129 | 0.371 | 2.406 | 2.696 | 0.066 | 0.085 | 2.407 | 2.612 | 2.566 | 2.624 |
| 4 | 0.082 | 1.068 | 1.391 | 1.912 | 1.994 | 2.726 | 0.074 | 2.769 | 2.387 | 2.437 | 2.822 | 3.289 | 3.169 | 0.064 | 2.864 | 3.096 | 3.221 | 3.319 | 3.220 |
| 5 | 0.063 | 0.083 | 0.136 | 0.156 | 0.246 | 0.216 | 0.057 | 0.065 | 0.104 | 0.085 | 0.197 | 0.732 | 0.261 | 0.056 | 0.126 | 0.588 | 0.657 | 0.700 | 0.522 |
| 6 | 0.059 | 0.073 | 0.058 | 0.066 | 0.071 | 0.071 | 0.061 | 0.068 | 0.066 | 0.061 | 0.086 | 0.623 | 0.488 | 0.054 | 0.075 | 0.458 | 0.623 | 0.641 | 0.489 |
| 7 | 0.050 | 0.052 | 0.058 | 0.062 | 0.091 | 0.091 | 0.046 | 0.049 | 0.066 | 0.048 | 0.152 | 1.146 | 1.100 | 0.045 | 0.273 | 0.863 | 1.577 | 1.669 | 1.505 |
| 8 | 0.070 | 0.087 | 0.254 | 0.293 | 0.710 | 0.698 | 0.070 | 0.076 | 0.718 | 0.812 | 1.463 | 1.998 | 1.624 | 0.058 | 0.101 | 0.655 | 0.894 | 0.937 | 0.820 |
| 8 A492 nm | 0.056 | 1.765 | 3.964 | 4.077 | 6.345 | 7.494 | 0.514 | 4.026 | 6.924 | 7.390 | 9.457 | 16.44 | 15.48 | 0.823 | 4.367 | 14.03 | 16.58 | 16.43 | 15.78 |

TABLE 2-continued

| | HCV Peptide Segments | | | | | | | | | | | | | | | | | |
|---|---|---|---|---|---|---|---|---|---|---|---|---|---|---|---|---|---|---|
| | I | | | | | | II | | | | | | | III | | | | | |
| Specimens | A | B | C | D | E | F | A | B | C | D | E | F | G | A | B | C | D | E | F |
| i = 1 | | | | | | | | | | | | | | | | | | | |
| % Relative Immunoreactivity | 3.0 | 10.3 | 23.9 | 24.6 | 38.2 | 45.6 | 3.1 | 24.3 | 41.7 | 44.9 | 57 | 99 | 93.2 | 4.9 | 26.3 | 85 | 100 | 99 | 95 |

Based on the above-mentioned epitope mapping study, four representative EIAs were configurated using Peptide IIG alone, a mixture of two Peptides IIF and IIID, a mixture of IIF, iIID and V, or a mixture of IIH and V as the solid phase antigen.

FIGS. 2-1 and 2-2 depict the comparison, by signal to cutoff ratio, between the peptide based HCV-EIA employing Peptide IIG, at 5 ug/mL coating concentration, and that of recombinant SOD/HCV C100-3 protein based HCV-EIA. In FIG. 2-1, a well-characterized HCV antibody positive control at various serum dilutions was used as the sample. In FIG. 2-2, a panel of serum specimens derived from serial bleedings of a single individual spanning a period of sero-conversion to anti-HCV reactivity was used. Similar dilution titers and equal ability to identify date of sero-conversion, the two parameters indicative of the sensitivity of each assay, are obtained with the synthetic peptide based EIA according to the present invention and rDNA HCV C-100 based EIA, except that the peptide based assay according to the present invention is more sensitive, conferring a higher signal to cutoff ratio to its positive specimens.

FIG. 3-1 and 3-2 depict the frequency distribution of the synthetic peptide based HCV-EIA signal to cutoff ratios, using Peptide IIG at 5 ug/mL as the coating concentration, obtained with 264 normal serum and 264 normal plasma specimens from commercial sources. The mean s/c ratios for the negative (n=250) and screened out positive (i.e. n=14) serum specimens are 0.034 and 7.202 respectively; for the negative (n=255) and positive (n=9) normal plasma specimens the mean ratios are 0.084 and 7.089 respectively. A sharp contrast between the screened out positives and all the negatives is obtained with the peptide based HCV-EIA of the present invention.

Based on the high degree of sensitivity and specificity of the peptide compositions according to the present invention in their immunoreactivities to antibodies to HCV, it is believed that the peptide compositions according to the present invention may also be useful as vaccines to prevent NANBH, and as immunogens for the development of both monoclonal and polyclonal antibodies to HCV in mammals, including humans. The peptide compositions when coupled to a protein, or synthesized on a polymeric carrier resin (e.g., an octameric branching lysine resin) or when polymerized to homo or hetero dimers or higher oligomers by cysteine oxidation, induced disulfide cross linking, or by use of homo or hetero functional multivalent cross linking reagents, can be introduced to normal subjects to stimulate production of antibodies to HCV in healthy mammals.

The advantages of using the peptides according to the present invention are many.

Since the peptide compositions according to the present invention are not derived biologically from the virus, there is no danger of exposing the normal subjects who are to be vaccinated to the disease.

The peptides can be chemically synthesized easily. This means that there is no involvement with the HCV at any time during the process of making the test reagent or the vaccine. Another problem which can be minimized by the process of the present invention is the false positive results caused by the presence of antigenic materials from host cells co-purified with the HCV fusion protein. Certain normal individuals have antibodies to E. Coli or yeast proteins which are cross reactive with the antigenic materials from host cells. Sera from these normal individuals may show a positive response in the immunoassays.

Further, with appropriate amino acid modifications or substitutions, it is expected that various peptide analogues based on the prescribed amino acid sequence can be synthesized with properties giving rise to lower background readings or better binding capacity to solid phases useful for HCV antibody screening assays.

Moreover, because the peptide compositions of the present invention are synthetically prepared, the quality can be controlled and as a result, reproducibility of the test results can be assured. Also, since very small amounts of peptides are required for each test procedure, and because the expense of preparing the peptides is relatively low, the cost of screening body fluids for antibodies to HCV, diagnosis of NANBH infection, or the preparation of a vaccine is relatively low.

The peptides prepared in accordance with the present invention can be used to detect HCV infection and diagnose NANBH by using them as the test reagent in an enzyme-linked immunoadsorbent assay (ELISA), an enzyme immunodot assay, an agglutination based assay, or other well-known immunoassay devices. The preferred method is ELISA. The ELISA technique is exemplified in Examples 1, 2, 8–10, 12 and 14–18 and the agglutination based assay in Examples 3 and 4. The Examples are used to illustrate the present invention and are not to be used to limit the scope of the invention.

It is to be noted that in the following methods, 0.25% by weight of glutaraldehyde may be added to the coating buffer to facilitate better peptide binding onto the plates or beads. Further, horseradish peroxidase (HRPO) conjugated mouse monoclonal anti-human IgG antibody or the HRPO conjugated second antibodies from any other animal species may be used in place of the HRPO-conjugated goat anti-human IgG as the second antibody tracer.

The gelatin used in these processes can include calf skin gelatin, pig skin gelatin, fish gelatin or any known available gelatin proteins, or be replaced with albumin proteins.

EXAMPLE 1

Measurement of Relative (%) Immunoreactivity for synthetic peptide covering an immunodominant region of the HCV protein C-100 by an Enzyme-Linked Immunosorbent Assay Wells or 96-well plates were coated at 4° C. overnight (or 1 hour at 37° C.), with each of the thirty one peptides: IA to IF, IIA to IIH, IIIA to IIIF, IV, V, VIA to VIE (see Table 1) prepared as described at 5 ug/mL at 100 uL per well in 10 mM NaHCO$_3$ buffer, pH 9.5. The peptide coated wells were then incubated with 250 uL of 3% by weight of gelatin in PBS at 37° C. for 1 hour to block non-specific protein binding sites, followed by three washes with PBS containing 0.05% by volume of TWEEN 20 and then dried. The test specimens were diluted with PBS containing 20% by volume normal goat serum, 1% by weight gelatin and 0.05% by volume TWEEN 20 at dilutions of 1:20 volume to volume, respectively. 200 uL of the diluted specimens were added to each of the wells and allowed to react for 15 minutes at 37°.

The wells were then washed six times with 0.05% by volume TWEEN 20 in PBS in order to remove unbound antibodies. Horseradish peroxidase conjugated goat anti-human IgG was used as a second antibody tracer to bind with the HCV antibody-peptide antigen complex formed in positive wells. 100 uL of peroxidase labeled goat anti-human IgG at a dilution of 1:1800 in 1% by volume normal goat serum, 0.05% by volume TWEEN 20 in PBS was added to each well and incubated at 37° C. for another 15 minutes.

The wells were washed six times with 0.05% by volume TWEEN 20 in PBS to remove unbound antibody and reacted with 100 uL of the substrate mixture containing 0.04% by weight orthophenylenediamine (OPD) and 0.12% by volume hydrogen peroxide in sodium citrate buffer, pH 5.0.

This substrate mixture was used to detect the peroxidase label by forming a colored product. Reactions were stopped by the addition of 100 uL of 1.0M H$_2$SO$_4$ and the absorbance measured using an ELISA reader at 492 nm (i.e. A$_{492}$). Assays were performed in singlet at one specimen dilution (1:20) with a panel of eight representative HCV antibody positive sera, along with the specimen diluent blank, non-reactive, weakly reactive and strongly reactive controls (NRC, WRC, SRC) all in duplicates.

Results obtained from this study are shown in Table 2. According to the EIA absorbance readings at 492 nm (y axis) and the amino acid sequences for each of the corresponding HCV peptides (x axis), representative immunoreactivity profiles are plotted for four of the eight sera as shown in FIGS. 1-1 to 1-4. Relative (%) immunoreactivity index for each of the 31 peptides is calculated using Peptide IIID as a reference based on the total absorbance of eight sera at 492 nm (See Tables 1 and 2). FIG. 1 shows the amino acid sequences of the immunodominant region according to data presented in Tables 1 and 2, and precisely delineates the amino acid residues (underlined) that contribute (—marginally, moderately, and—strongly) to the immunoreactivities.

In summary, epitope mapping analysis conducted with a series of 31 overlapping peptides covering an immunodominant region of HCV, spanning a total of 90 amino acid residues as illustrated in Table 1, reveals a varying degree of immunoreactivities between different HCV antibody positive samples and these HCV peptides. Based on this study, several discontinuous epitopes are located within this immunodominant region. Contrary to what is speculated by the conventional wisdom, it is found preferably to have peptides with longer amino acid chains, ideally longer than 20, synthesized in order to optimally present these antigenic determinants to HCV antibodies.

Based on the above-mentioned epitope mapping study, four representative EIAs using peptide IIG alone, or a mixture of Peptides IIF and IID, or a mixture of IIF, IIID and V, or a mixture of IIH and V as the solid phase antigen were configured for the following efficacy studies as demonstrated in Examples 2, 8, 9, 10 and 12.

EXAMPLE 2

Detection of Antibodies to HCV by an Enzyme-Linked Immunosorbent Assay

Wells of 96-well plates were coated at 4° C. overnight (or for 1 hour at 37° C.) with either Peptide IIG alone at a coating concentration of 0.5 ug per well (designated as IIG EIA) or with a mixture of two Peptides IIF and IIID (designated as IIF/IIID EIA) in a ratio by weight of IIF:IIID=1:1 at 1 ug per well of the mixture in 100 uL 10 mM NaHCO$_3$ buffer pH 9.5. The peptide coated wells were then incubated with 250 uL of 3% by weight of gelatin in PBS at 37° C. for 1 hour to block non-specific protein binding sites, followed by three more washes with PBS containing 0.05% by volume of TWEEN 20 and dried.

The test specimens were diluted with PBS containing 20% by volume normal goat serum, 1% by weight gelatin and 0.05% by volume TWEEN 20 at dilutions of 1:20 volume to volume, respectively. 200 uL of the diluted specimens were added to each of the wells and allowed to react for 15 minutes at 37°.

The wells were then washed six times with 0.05% by volume TWEEN 20 in PBS in order to remove unbound antibodies. Horseradish peroxidase conjugated goat anti-human IgG was used as a second antibody tracer to bind with the HCV antibody-peptide antigen complex formed in positive wells. 100 uL of peroxidase labeled goat anti-human IgG at a dilution of 1:1800 in 1% by volume normal goat serum, 0.05% by volume TWEEN 20 in PBS was added to each well and incubated at 37° C. for another 15 minutes.

The wells were washed six times with 0.05% by volume TWEEN 20 in PBS to remove unbound antibody and reacted with 100 uL of the substrate mixture containing 0.04% by weight orthophenylenediamine (OPD) and 0.12% by volume hydrogen peroxide in sodium citrate buffer, pH 5.0. This substrate mixture was used to detect the peroxidase label by forming a colored product. Reactions were stopped by the addition of 100 uL of 1.0M H$_2$SO$_4$ and the absorbance measured using an ELISA reader at 492 nm (i.e. A$_{492}$). Assays were performed in singlet at one specimen dilution (1:20) with all test specimens. Each plate run is accompanied by a panel of eight controls including the specimen diluent blank, negative, weak HCV reactive and strong HCV reactive controls, all in duplicate. The strongly reactive control was adjusted by diluting a HCV positive serum in the specimen dilution buffer at 1:300, which gave an absorbance value at 492 nm of about 1.5 when performed in this standard 45 minute assay procedure. A cutoff value is calculated based on the following formula: Cutoff=(0.1×SRC)+NRC. Both the raw absorbance (designated as signal) and the ratio of signal to cutoff are recorded for all specimens analyzed.

The following groups of specimens were analyzed on the HCV peptide based EIA according to the present invention, with the plates coated either with 5 ug/mL of peptide IIG or a mixture containing 5 ug/mL IIF and 5 ug/mL IIID:

(a) A well-characterized HCV antibody positive control based on serum dilutions; (on both IIG and IIF/IIID EIAs)

(b), a panel of serum specimens derived from serial bleedings of a single individual spanning a period of sero-conversion to anti-HCV reactivity; (on both IIG and IIF/IIID plates)

(c) 264 normal serum and 264 normal plasma specimens from commercial sources; (on IIG plates only)

(d) individuals positive for HBsAg, (n=30); (on both IIG and IIF/IIID plates)

(e) individuals positive for antibodies to HBc protein, (n=39); (on both IIG and IIF/IIID plates)

(f) individuals with elevated (>100 I.U./L) alanine aminotransferase (ALT) enzyme activity, (n=174); (on both IIG and IIF/IIID plates)

(g) individuals positive for antibodies to retroviruses HIV-1(n=100), HIV-2(n=10), HTLV-I/II(n=14); all asymptomatic, (total n=124); (on both IIG and IIF/IIID plates)

(h) individuals with AIDS, ARC(n=200) or ATL (n=170) disease, (total n=370); (on both IIG and IIF/IIID plates) and (i) individuals with autoimmune disease (n=20). (on IIG plates only)

(j) recombinant SOD/HCV C100-3 HCV-EIA repeatably reactive specimens obtained from a random donor population, (n=23). (on both IIG and IIF/IIID plates).

Figures 1, 2, 3, 4:
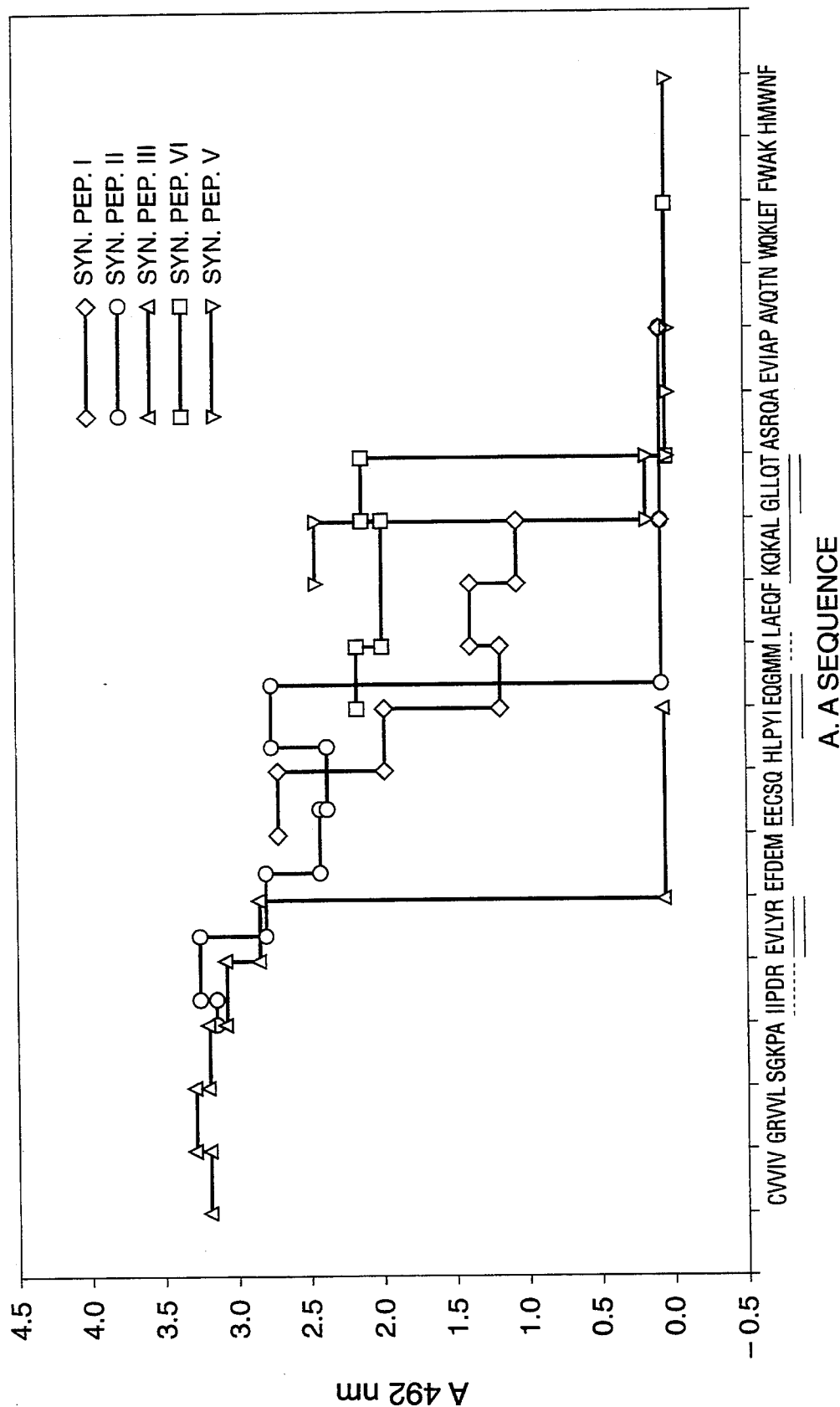
Figures 1, 3:
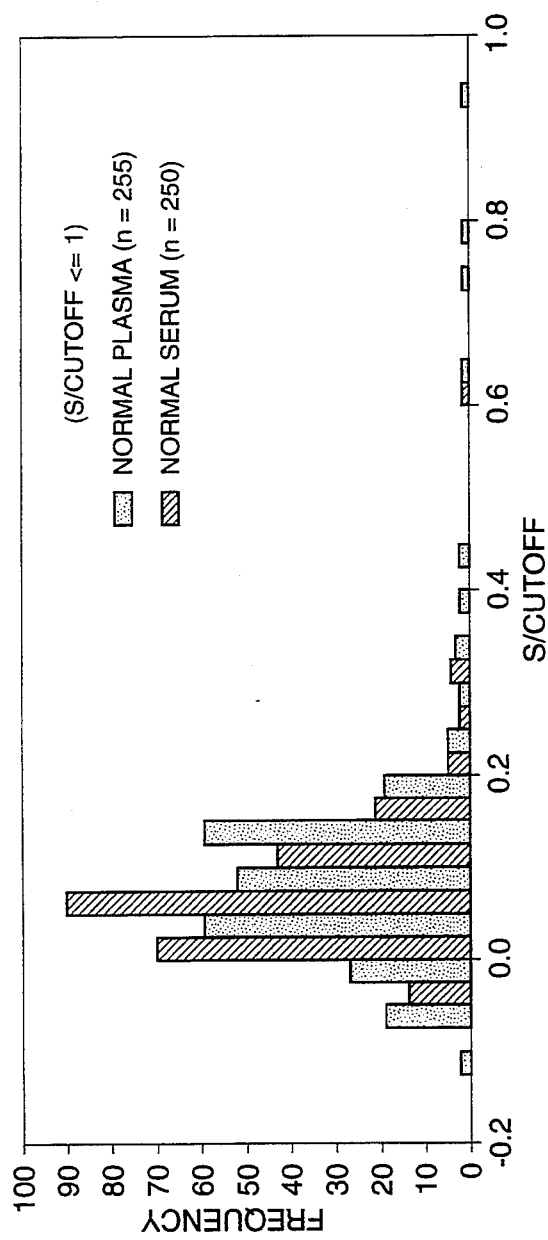
Figures 2, 3:
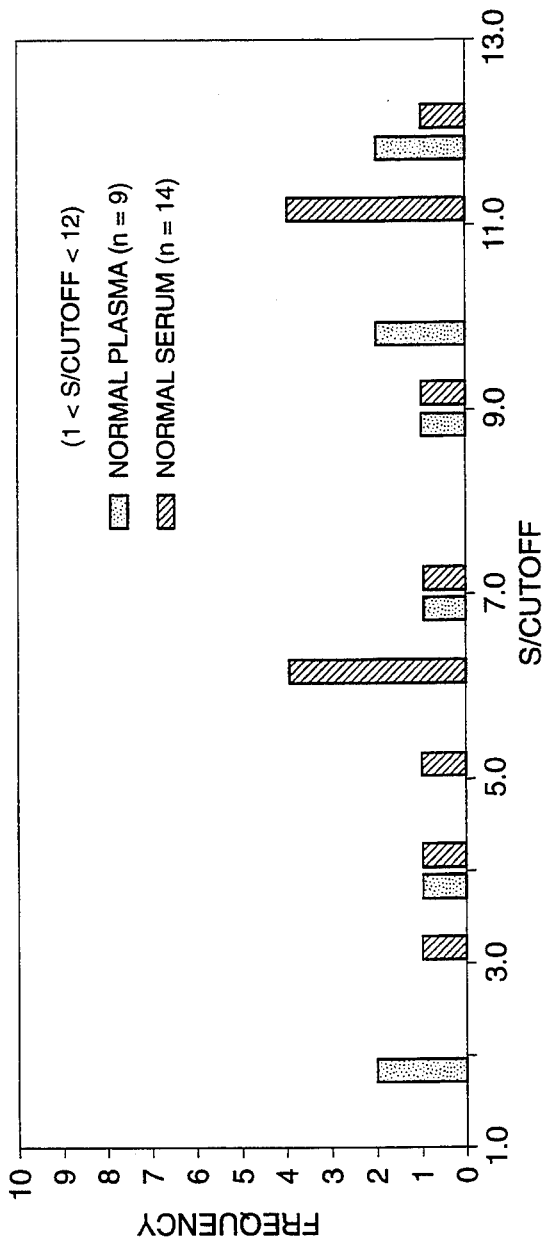
Figure 4:
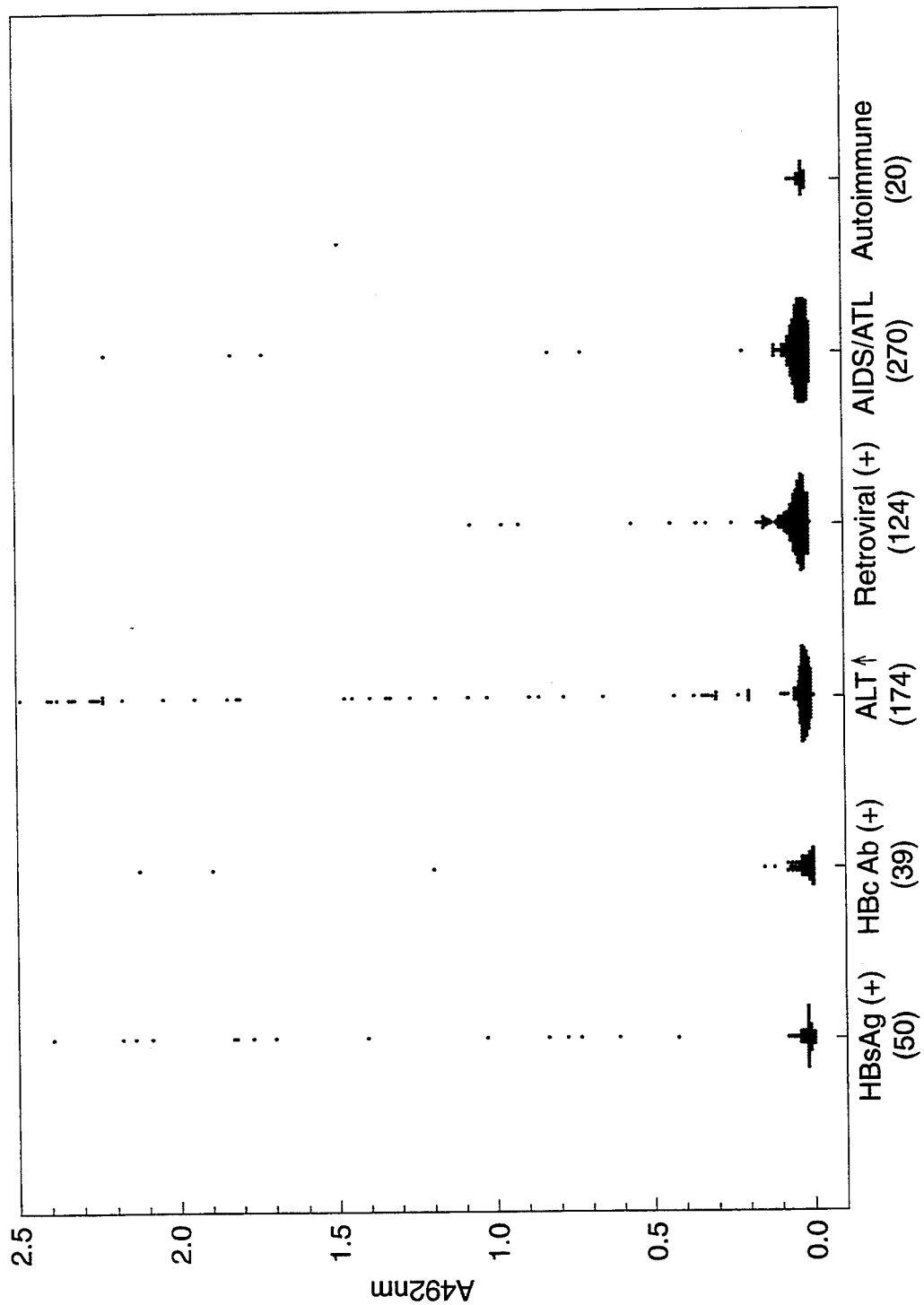
Figure 5:
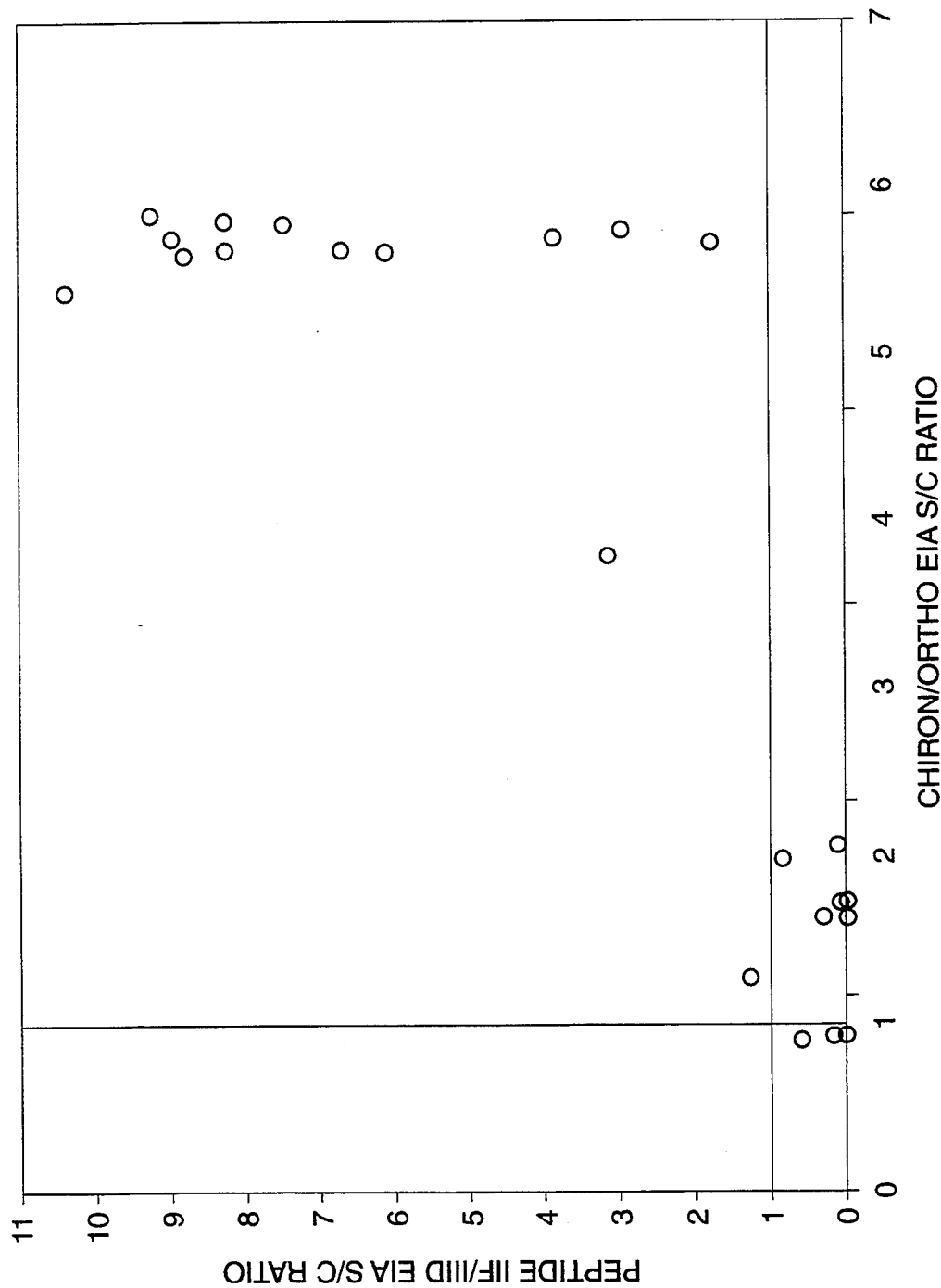
FIG. 5 provides a comparison between EIA results using the Peptides IIF and IIID of the present invention and recombinant SOD/HCV C100-3 as represented by their respective s/c ratios on a panel of repeatably reactive specimens (n=23) obtained from a random donor population.
Figure 6:
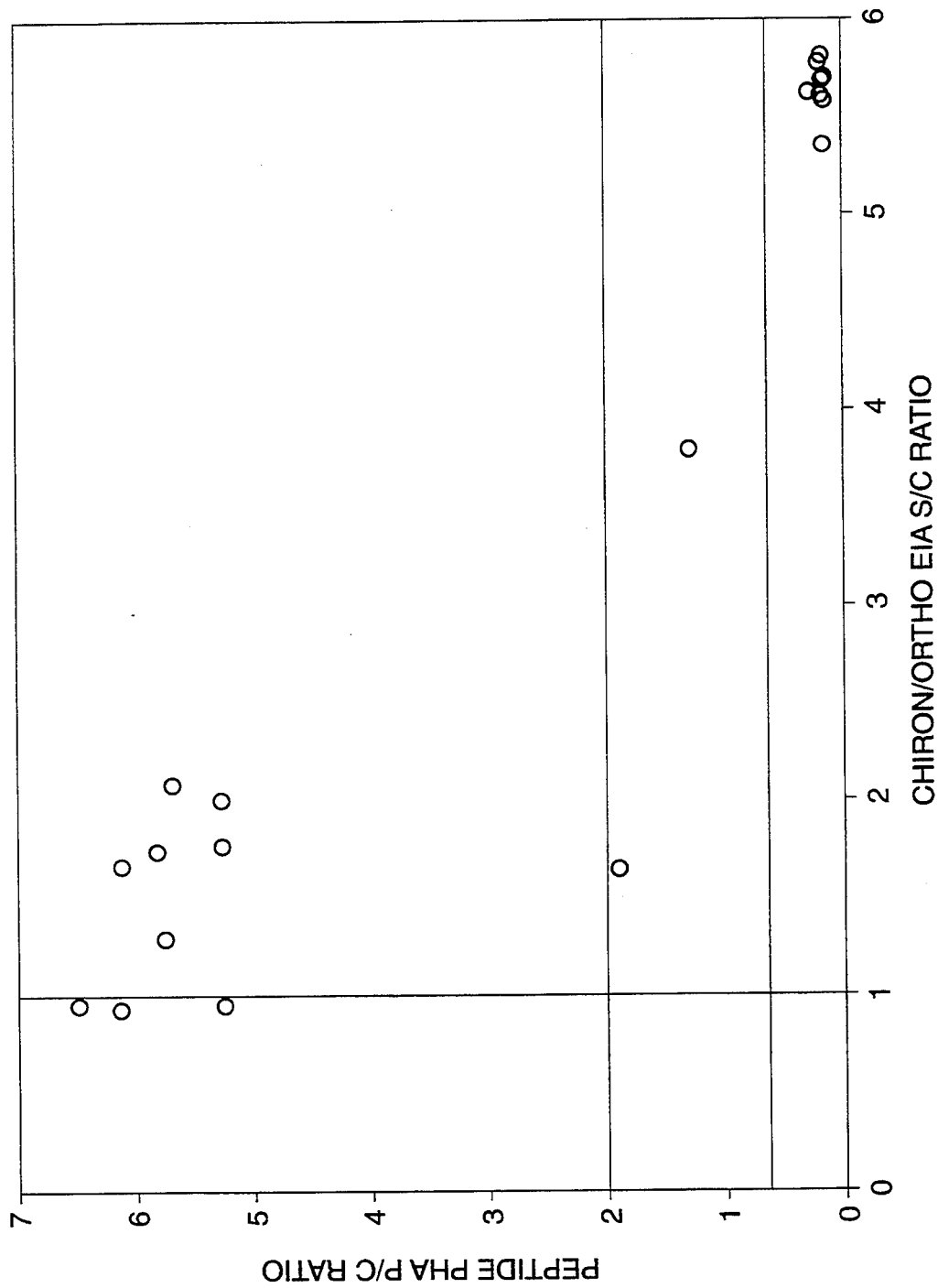
FIG. 6 provides a comparison between a passive hemagglutination assay (PHA), using Peptide IIG, and the recombinant SOD/HCV C100-3 EIA as represented by their respective P/C and s/c ratios for a panel of SOD/HCV C100-3 HCV EIA repeatably reactive specimens (n=20) obtained from a random donor population. For results obtained by the PHA, the agglutination pattern is quantitated by a specially designed optical reading instrument (manufactured by Olympus Corporation) where a P/C ratio of larger than 20 is considered negative whereas a P/C ratio of less than 20 is considered positive.

Results obtained from groups (a) and (b) are presented 18 in FIGS. 2-1 and 2-1 and 2-2 respectively (data obtained on IIG plates only), from group (c) in FIGS. 3-1 and 3-2; from groups (d) to (i) in FIG. 4, from group (j) in Table 3 and FIGS. 5 and 6.

In brief, as shown in FIGS. 2-1 and 2-2, a comparison, by signal to cutoff ratio, between the peptide based HCV-EIA of the present invention employing peptide IIG and that of recombinant SOD/HCV C100-3 protein based HCV-EIA produced by Chiron/Ortho. Similar dilution titers and equal ability to identify date of sero-conversion, the two parameters indicative of each assay's sensitivity, are obtained for both assays. However, the assay according to the present invention is more sensitive and confers a higher signal to cutoff ratio to its positive specimens.

TABLE 3

| SAMPLE ID No. | rDNA HCV S/C | RPT S/C | RPT S/C | ALT (IU/L) | Anti-HBc (S/C) | OTHER POSITIVES | Peptide HCV-EIA S/C |
|---|---|---|---|---|---|---|---|
| 1 161 | 5.33 | 5.56 | 5.56 | 36/56 | 2.10 | | 11 |
| 2 280 | 5.76 | 5.56 | 5.56 | 78/56 | 0.07+ | HBc, ALT | 10 |
| 3 374 | 1.98 | 2.45 | 2.45 | 20/56 | 1.97 | | 0.573 |
| 4 517 | 5.79 | 5.68 | 5.68 | 34/56 | 2.04 | | 11 |
| 5 561 | 1.74 | 2.75 | 2.47 | 21/56 | 2.46 | | 0.172 |
| 6 675 | 0.93 | 1.33 | 1.54 | 29/56 | 1.98 | | 0.135 |
| 7 720 | 5.68 | 5.68 | 5.68 | 57/56 | 0.08+ | HBc, ALT | 13 |
| 8 773 | 5.56 | 5.88 | 5.88 | 86/56 | 2.07 | HIV, ALT | 8.625 |
| 9 797 | 3.79 | 4.35 | 4.29 | 74/56 | 0.38+ | HBc, ALT | 1.802 |
| 10 869 | 5.66 | 5.59 | 5.59 | 35/56 | 2.45 | | 9.755 |
| 11 873 | 5.66 | 5.59 | 5.59 | 26/56 | 2.34 | | 1.189 |
| 12 1003 | 1.63 | 1.24 | 1.01 | 31/56 | 2.02 | | 0.078 |
| 13 1073 | 5.73 | 5.59 | 5.59 | 17/56 | 0.12+ | HBc | 2.594 |
| 14 1099 | 1.72 | 1.76 | 1.94 | 10/56 | 1.84 | | 0.083 |
| 15 1118 | 5.59 | 5.79 | 5.79 | 10/56 | 0.31+ | HBc | 10.5 |
| 16 1336 | 0.93 | 1.38 | 1.38 | 18/56 | 2.15 | | 0.010 |
| 17 1501 | 5.75 | 5.67 | 5.67 | 36/56 | 1.99 | | 5.349 |
| 18 1530 | 1.27 | 1.48 | 1.50 | 23/56 | 2.30 | | 0.943 |
| 19 1557 | 0.91 | 1.29 | 1.28 | 20/56 | 2.20 | | 0.385 |
| 20 1652 | 2.06 | 2.64 | 2.72 | 42/56 | 1.72 | | 0.135 |
| 21 1877 | 5.59 | 5.63 | 5.63 | 65/56 | 2.16 | ALT | 4.943 |
| 22 1940 | 1.64 | 1.47 | 1.17 | 29/56 | 2.35 | | 0.052 |
| 23 2017 | 5.60 | 5.84 | 5.84 | 11/56 | 0.19+ | HBc | 6.786 |

Col. 1,2,3, = Ortho's HCV results in s/c.; Col 5 = ALT values over cutoff in IU/L; Col. 6 = Abbott's Anti-HBc results in s/c where results UNDER 1.00 are POSITIVE due to the competitive binding principle of this assay.

As shown in FIGS. 3-1 and 3-2, the frequency distribution of the HCV-EIA signal to cutoff ratios, using peptide IIG at 5 ug/mL as the coating concentration, that was obtained with 264 normal serum and 264 normal plasma specimens for commercial sources suggested a repeatably reactive rate of 5.3% and 3.4% respectively. These percentages are relatively high compared with those reported in field clinical trials (usually 0.5–1.0%) using the rDNA HCV C-100 based EIA kit (Chiron/Ortho). However, in the assay according to the present invention, the mean s/c ratios for the negative (n=250) and screened out positive (i.e. n=14) serum specimens are 0.034 and 7.202 respectively; for the negative (n=255) and positive (n=9) normal plasma specimens the mean ratios are 0.084 and 7.089 respectively. Such a sharp contrast between the screened out positives and all the negatives probably precludes the likelihood of a high false positive rate. Since these normal specimens are derived from commercial plasma centers where the paid donors usually represent a population with higher incidence of viral markers than the rigorously monitored blood banks, a higher repeatably reactive rate is also considered reasonable. Previous clinical studies indicated that between 7 to 10 percent of patients receiving transfusions developed NANBH, where 90% of these post-transfusion hepatitis cases are caused by the NANBHV(5). These reports also provide some support to the interpretation of the data obtained herein that a high reactivity represents a true positive result.

Results obtained from the screening of a total of 677 well-characterized clinical specimens previously categorized into six groups, from (d) to (i) using a representative lot of plates coated with Peptide IIG, were plotted on a histogram as shown in FIG. 4.

Fifteen out of fifty (i.e. 30%) HBsAg carriers, 3 out of 39 (i.e. 8%) HBc antibody positive individuals, 43 out of 174 (i.e. 24.7%) individuals with elevated ALT enzyme activity, 8 out of 124 (6.5%) asymptomatic individuals with retroviral antibodies, 6 out of 270 (i.e. 2.2%) individuals with retroviral related disease, and 0 out of 20 (i.e. 0%) individuals with autoimmune disease were found to be repeatably reactive with the peptide HCV EIA of the present invention using peptide IIG. All these positive specimens were also found to be positive when tested on peptides IIF/IIID HCV EIA, although with much higher s/c ratios.

A much higher percentage of positive cases was found with those who have abnormal liver functions (24.7%) or previous infection(s) with Hepatitis B (30% and 8%) when compared to those with other infections or diseases (e.g. 6.5%, 2.2% and 0%).

Note: Sera from HBsAg carriers were kindly provided by the Infectious Diseases Laboratory of the American Red Cross; sera from HBc antibody positive donors were obtained from Boston Biomedica Inc.; sera from individuals with elevated ALT levels (>100 I.U./L) were obtained from both Boston Biomedica Inc. and NABI laboratory; sera from asymptomatic individuals with retroviral antibodies (HIV-1 and HTLV-1) were obtained from New York Blood Center, and those with HIV-2 antibodies were from Guinea Bissau of West Africa, kindly provided by Dr. O. Varnier of Italy,; sera from patients with ATL were kindly provided by the Japanese Red Cross; sera from patients with AIDS and ARC, were kindly provided by Dr. D. Knowles at Columbia University College of Physicians and Surgeons, and Dr. F. Siegal at the Long Island Jewish Hospital; sera from patients with various complications of autoimmune diseases were kindly provided by Dr. N. Chiorazzi of the Cornell University Medical School. All sera have been characterized by additional licensed serologic markers before inclusion in the current study.

Table 3 illustrates results obtained with the peptide based HCV EIA described in this invention on a panel of 23 recombinant HCV EIA repeatably reactive specimens obtained from a random donor population. Data on each specimen's level and HBc antibody reactivity are provided as supplemental information for indirect confirmation of NANBH status of the positive donors. As can be seen from the Table, all eight specimens with indirect confirmation of their NANBH status scored positive in the peptide based EIA according to the present invention (on both IIG and IIF/IIID plates). In addition, four specimens that scored high on the peptide based assay also scored as strong positives by the recombinant HCV EIA, thus further confirming the HCV positivity of these specimens. ,Only one specimen scored marginally positive on the peptide based HCV EIA, which lacks the other markers. However, this specimen scored positively with the recombinant HCV EIA. The remaining ten specimens that scored negative by the peptide based EIA according to the present invention all had a marginal s/cutoff ratio of between 0.9 to 2.6. FIG. 5 provides a direct correlation between the peptide based HCV EIA of the present invention and the recombinant based HCV EIA by their respective s/cutoff ratios for this panel. Thus, the peptide based HCV EIA of the present invention can clearly differentiate the repeatably reactive specimens previously screened out by the rDNA based HCV EIA into two distinct groups, a positive group which correlated highly to those with other known NANBH markers and a negative group which probably represents specimens with extraneous reactivities unrelated to HCV. In addition to its use as a screening assay, the peptide based HCV EIA may also function as a positive confirmatory test for the rDNA based HCV EIA.

Note: This well-characterized serum panel was kindly provided by Dr. C. Fang of the American Red Cross QC laboratory.

EXAMPLE 3

Detection of Antibodies to HCV By an Agglutination Based Assay

The presently claimed HCV peptides, synthesized according to the Merrifield solid phase method, can be conjugated to bovine serum albumin (BSA) by a simple crosslinking method in the presence of a low percentage of glutaraldehyde solution (0.025%), or with other crosslinking reagents such as m-maleimidobenzoyl-N-hydroxysuccinimide ester (MBS) according to a previously published procedure (Biochemistry, 18:690–697, 1979). For example: to 0.32 mL. of a BSA solution (10 mg/mL in 0.01 M phosphate buffer, pH 7.0) at room temperature is added 0.013 mL of an MBS solution (0.025 mg/mL in dimethylformamide). The amount of MBS added to the BSA solution can be varied dependent on the optimal molar ratio of BSA to MBS determined for a specific conjugate studied. The mixture is stirred at room temperature for 1 hour, after which it is centrifuged to remove any precipitated albumin. The clarified mixture is then subjected to gel filtration on Sephadex G-25 and the protein-containing fractions, as detected by their absorbance at 280 nm, are pooled and stored frozen at −70° C. until needed.

The peptides are dissolved in $H_2O$ at 10 mg/mL. A predetermined amount of each peptide solution is added dropwise to the previously activated BSA-MBS solution and stirred at room temperature for 3 hours. The final peptide-BSA conjugates are separated from other free peptides by gel filtration or extensive dialysis. The ratio of peptide to BSA is determined by SDS-PAGE according to conventional methods.

Using the above mentioned peptide-BSA conjugation process, conjugated peptide IIG-BSA was absorbed to double aldehyde fixed human O erythrocytes at pH 4.0. The peptide-conjugate coated erythrocytes were then treated with $NaBH_4$ to prevent non-specific protein binding. The peptide-conjugate coated erythrocytes were then washed with PBS and incubated with 5% normal human serum-PBS solution. These processed cells were then used in an agglutination assay for the detection of HCV antibodies in both serum and plasma specimens. The specimens were diluted 1:10 in a sample diluent buffer and an equal volume of the indicator cells (50 uL) was mixed with the diluted specimens. The agglutination pattern was settled within one hour; and the assay results were read by the naked eye and further quantitated by an optical device (manufactured by Olympus Corporation) which gave a P/C ratio, as determined by the absorbance readings of the periphery and center of the wells. In this experiment, a P/C ratio of 20 was set as the assay cutoff value, i.e. a positive agglutination pattern had a ratio of <20 and a negative pattern, >20.

A total of 20 rDNA HCV EIA repeatably reactive specimens were tested for antibodies to HCV in the above-described HCV passive hemagglutination assay (PHA) employing Peptide IIG-BSA conjugate as the solid phase. FIG. 6 provides a correlation study between the peptide based HCV PHA and the recombinant based HCV EIA by their respective P/C and s/c ratios. All samples with s/c EIA ratios higher than 3 were found to be positive with the HCV PHA test. With the exception of one, all specimens having borderline s/c ratios (between 0.9 to 2) scored as negative in this PHA test.

EXAMPLE 4

Detection of Antibodies to HCV By An Agglutination Assay Utilizing As the Solid Phase Immunosorbent Gelatin Particles, Erythrocytes Of Different Animal Species, Or Latex Particles Coated with a Mixture of HCV Peptides One mL thoroughly washed erythrocytes, gelatin particles, or polystyrene latex particles are coated with the HCV peptide mixture, or conjugates thereof at an effective concentration. The peptide mixture, or conjugates thereof, coated cells or particles are then incubated with serially diluted serum samples in the wells of a 96-well U-shaped microplate or on a slide. After being left at room temperature for about an hour, or a few minutes in the case of latex-particle based microagglutination, the settled agglutination pattern on the bottom of each well or on the slide is read; and the highest dilution showing a positive reaction is recorded.

This is a one-step assay which can be used for both qualitative and quantitative detection of antibodies to HCV in specimens including sera or biofluids.

EXAMPLE 5

A test kit for detecting HCV antibodies using an agglutination assay comprises a compartmented enclosure containing multiple microwell plates and other accessory materials for an agglutination assay including (1) a bottle of HCV peptide coated erythrocytes, gelatin particles or latex polystyrene particles; (2) a negative control; and, (3) an inactivated HCV positive control, and (4) specimen diluent. The procedure described in Examples 3 and 4 is to be followed.

EXAMPLE 6

An enzyme immunoassay based diagnostic test kit for the detection of HCV antibodies can be constructed. The test kit comprises a compartmented enclosure containing multiple 96-well plates coated prior to use with the HCV peptide or peptide mixtures of the present invention in 100 uL pH 9.5 10 mM NaHCO$_3$ buffer. The kit further comprises materials for enzyme detection in separate sealed containers consisting of: 1) a negative control; 2) an inactivated HCV positive control; 3) specimen diluent; 4) peroxidase labeled-second antibody to human IgG; and 5) a color change indicator consisting of, for example, orthophenylenediamine (OPD) and hydrogen peroxide in a phosphate citrate buffer. The procedure described in Examples 1 and 2 is to be followed.

In this test kit, 96-well plates, precoated with a peptide or peptide mixture of the present invention, can be replaced by polystyrene beads,or multiple minicolumns filled with controlled pore size glass beads, or nitrocellulose paper strip, precoated with the peptides of the present invention for use as the solid phase immunosorbent.

EXAMPLE 7

Immunization with Octameric HCV Peptides for the Elicitation of Sustaining High Titers of HCV Antibodies In addition to the use of synthetic HCV peptides as immunogens for the generation of sequence-related anti-HCV antibodies for the ultimate development of an epitope-based subunit NANBH vaccine, another approach using a limited sequential propagation of a trifunctional amino acid lysine to form a core that serves as a low-molecular weight matrix carrier for peptide immunogens can also be applied. The trifunctional amino acid, Boc-Lys(Boc), is particularly suitable since both N-α and N-ξ amino groups are available as reactive ends. Thus, sequential propagation of Boc-Lys(-Boc) will generate $2^n$ reactive ends. The first level coupling of Boc-Lys(Boc) will produce two reactive amino ends as a bivalent carrier. The sequential generations of a second and third step with Boc-Lys(Boc) will produce carriers containing four(tetra-valent), and eight (octa-valent) reactive amino ends to which peptide antigens are attached.

The HCV peptides as described in this invention can be incorporated onto this carrier system as illustrated below for the development of sustaining high titer HCV antibodies in mammals, including humans.

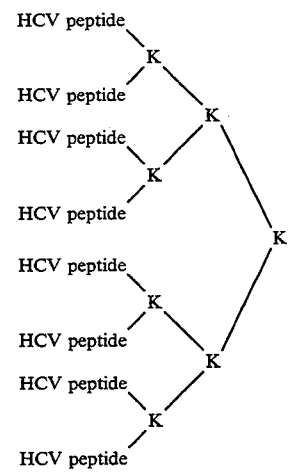

Octameric HCV peptides of the present invention (Table 1) using the solid phase method of Merrifield are synthesized by an automated peptide synthesizer, either Applied Biosystems (ABI) Model 430A, or Biosearch Model 9500.

Both acid-labile tert-butyloxycarbonyl (t-Boc) and acid-stable groups are used for the protection of N-α(amino acid and the functional side chains of the amino acids during the synthesis, respectively. The octameric peptides are synthesized by coupling onto a synthetic octamer resin.

An octamer resin is prepared by coupling di-t-Boc Lys onto 0.14 mmol/g MBHA (4-Methyl benzhydrylamine) resin. (Biosearch 9500 is used for this preparation due to its flexibility in scale). Di-Boc Lys single coupling is followed by two capping reactions (e.g. 0.3M Acetylimidazole in DMF dimethylformamide). The substitution level of synthetic octamer resin is determined by Ninhydrin Test.

Duncan Hartly random bred female guinea pigs (two per immunogen), weighing 400–500 gms, are used as the hosts. For initial immunizations, an aliquot of 100 ug octameric HCV peptide in 0.5 mL PBS is mixed with an equal volume of complete Freund's adjuvant and injected into each animal both subcutaneously and intradermally over multiple sites. After two to three weeks of rest, an identical dosage of the same immunogen is given as a boost into each animal except that incomplete Freund's adjuvant is used. The animals are bled by heart puncture periodically to monitor each serum's anti-HCV titers. Subsequent booster shots are given periodically.

EXAMPLE 8

Relative (%) Immunoreactivity for Synthetic Peptides By An Enzyme-Linked Immunoadsorbent Assay Wells of 96-well plates were coated at 4° C. overnight (or 1 hour at 37° C.), with each of the additional nine peptides, VA, VB, VC, VD, VE (=V), VIA, VIB, VIC, VID, VIE (see Table 1 for the above mentioned peptides), at 5 ug/mL at 100 uL per well in 10 mM NaHCO$_3$ buffer, pH 9.5. Each peptide's immunoreactivity was measured as previously described in Example 1. Results obtained for the 10 peptides in the V and VI series are shown in Table 2. According to the EIA absorbance readings at 492 nm (y axis) and the amino acid sequences for each of the corresponding HCV peptides (x axis), representative immunoreactivity profiles are plotted for four of the eight sera on the 10 peptides in the V and VI series, together with the first twenty peptides in the I, II and III series, as shown in FIGS. 1-1 to 1-4. Relative (%) immunoreactivity index for each of the additional 10 peptides is likewise calculated using peptide IIID as a reference. Additional clusters of residues, such as ASRQA and EVIAP, that are identified with these 10 peptides, were found to contribute additionally to the overall HCV antibody reactivity.

In summary, epitope mapping analysis conducted with a series of overlapping peptides reveals a varying degree of immunoreactivities between different HCV antibody positive samples and these HCV peptides. Based on the above-mentioned epitope mapping study, a third representative EIA using peptides IIF, IIID and V as the solid phase antigen was also configurated for testing as shown in Example 9 in comparison to that using peptide IIF and IIID.

EXAMPLE 9

Detection of Antibodies to HCV in Serial Samples by Enzyme-Linked Immunosorbent Assays (a) A coded panel consisting of 24 samples derived from a case of transfusion transmitted NANBH were tested in two types of EIAs using plates coated with either a mixture of IIF and IIID at 5, 5 ug/mL or a mixture of IIF, IIID and V at 5,5,5 ug/mL. The panel was provided by Dr. H. Alter of NIH and the results were decoded by his laboratory.

Figures 1, 7:
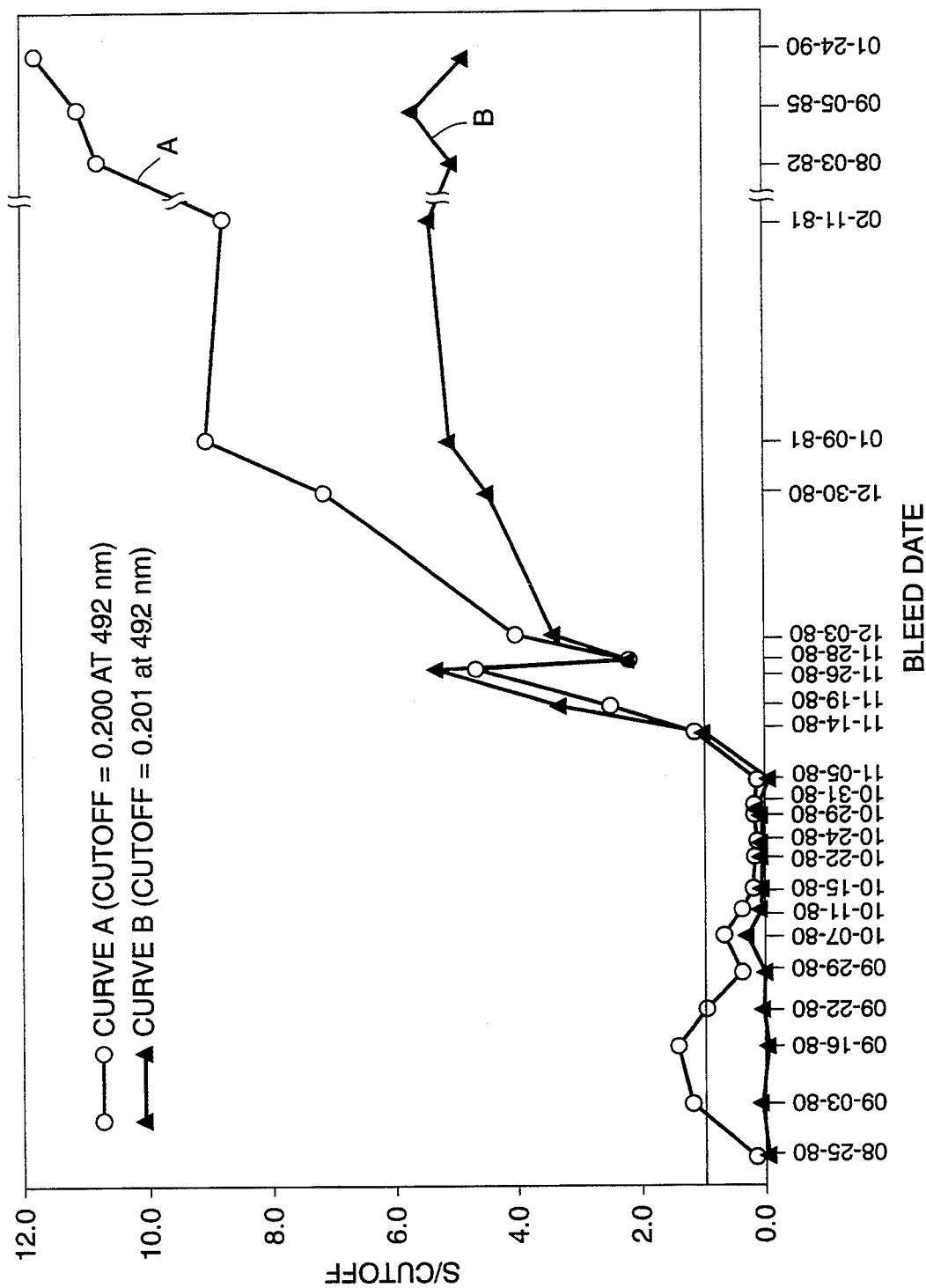
Figures 2, 7:
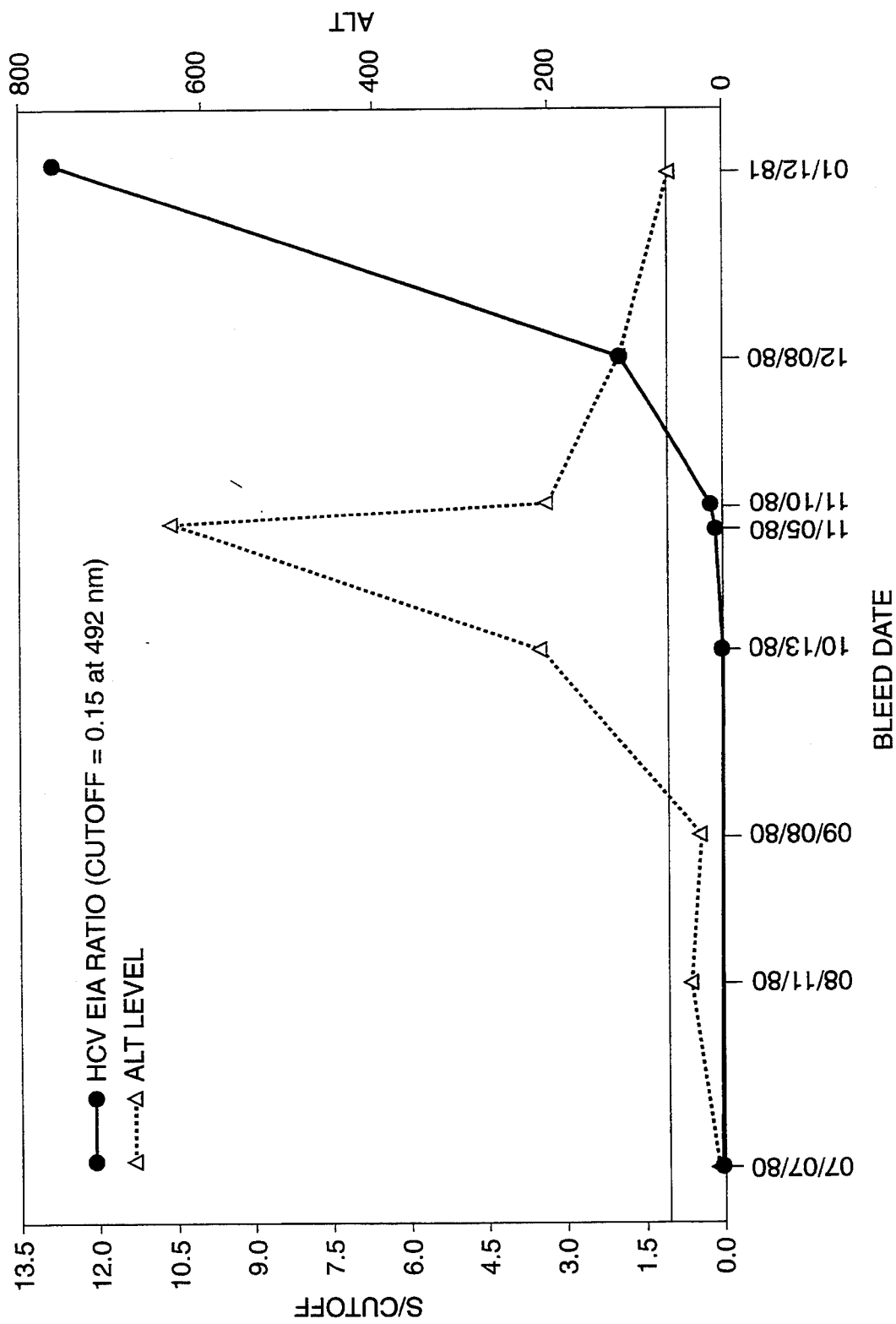
Figures 3, 7:
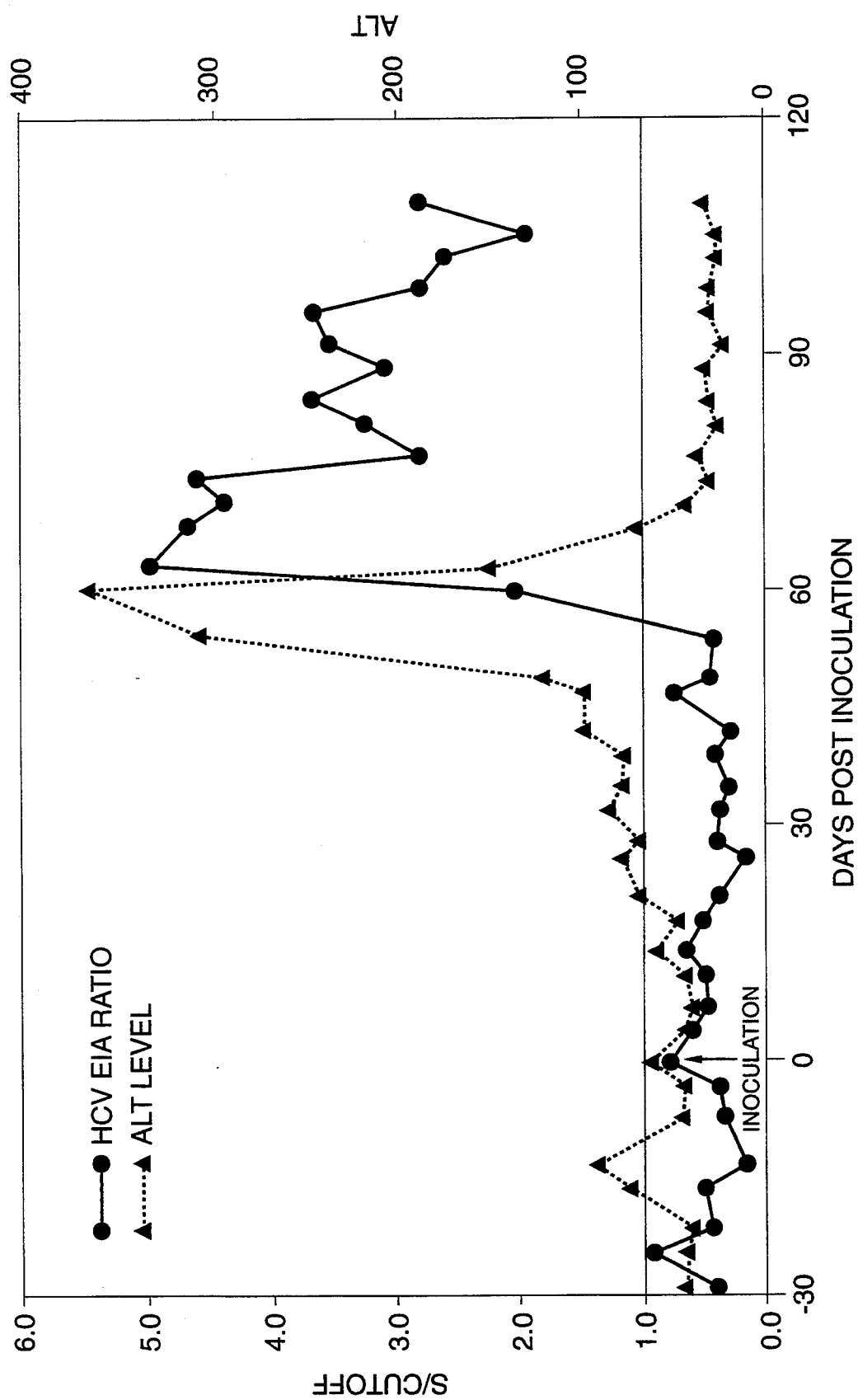

As shown in FIG. 7-1, the two anti-HCV profiles, as tested by two formats, using Peptides IIF/IIID/V coated plate (Curve A) and Peptides IIF/IIID coated plate (curve B) respectively, spanning a ten year period revealed an interesting contrast.

According to the record, the seronegative patient received HCV,contaminated blood units on Aug. 20, 1980. As a result of the transfusion, a trace amount of passive HCV antibodies was detected in the recipient's serum by format A. Active development of HCV antibodies by the recipient became detectable by both formats from November 14th on (about three months after the initial transfusion). The HCV antibodies, developed as a result of HCV infection through blood transfusion, persisted throughout the next ten years. Higher antibody signals were detected by plates coated with an extra peptide V (curve A) in sera collected four months after the transfusion. It appears that the epitope presented by peptide V, representing a neighboring immunodominant region, elicits abundant HCV antibodies at a slightly later stage than the epitopes represented by peptides IIF and IIID.

(b) Serial samples from one representative case of a hemodialysis patient with NANBH were provided by Dr. Cladd Stevens of New York Blood Center, New York, N.Y., and tested on plates coated with a mixture of three peptides, IIIF/IID/V. The sample histories are shown in FIG. 7-2. The results show that the peptide based EIA detects samples about two months after the onset of the acute phase of the disease as evidenced by the ALT elevation.

(c) Serial samples from a representative chimpanzee were tested with a peptide based HCV EIA using a mixture of IIIF/IID/V peptides. This chimpanzee was inoculated on day 0 with a well-characterized strain of NANBHV. Following the acute phase of infection as evidenced by the rise of the ALT levels, antibodies to HCV were detected about 60 days after inoculation [FIG. 7-3].

EXAMPLE 10

Screening of Low Risk Random Blood Donors With the Peptide Based HCV EIA 2035 donor specimens obtained in a blood bank setting were tested by EIA coated with a mixture of Peptides IIF, IIID and V at 5 ug/mL each following the procedure described in Example 2. The results are shown in FIGS. 8-1 and 8-2. The frequency distribution of the peptide based HCV-EIA signal to cutoff ratios, suggested an initial reactive rate of 1.18% and a repeatably reactive rate of 1.08 respectively. 88% of the initial reactive specimens are repeatably reactive indicating a high reproducibility of the assay. The repeatably reactive rate of the peptide based HCV EIA obtained with the low risk random blood donor specimens, all volunteers, is lower than that obtained from the commercial paid donor population (See Example 2).

EXAMPLE 11

Synthetic Peptide Based HCV Neutralization EIA As a Confirmatory Test wells of 96-well plates were coated at 4° C. overnight (or for 1 hour at 37° C.) with a mixture of two peptides IIF and IIID at 5 ug/mL each in 100 uL 10 mM NaHCO$_3$ buffer pH 9.5. Repeatably reactive specimens previously screened out by the direct HCV EIA were incubated with either a control specimen diluent buffer (i.e., PBS containing 20% by volume normal goat serum, 1% by weight gelatin and 0.05% by volume Tween 20) at a dilution of 1:20 volume to volume, or with the same specimen diluent buffer containing varying amounts of a HCV peptide canalogue IV (see Table 1 for its amino acid sequence) and allowed to react for an hour at 37°.

Figure 9:
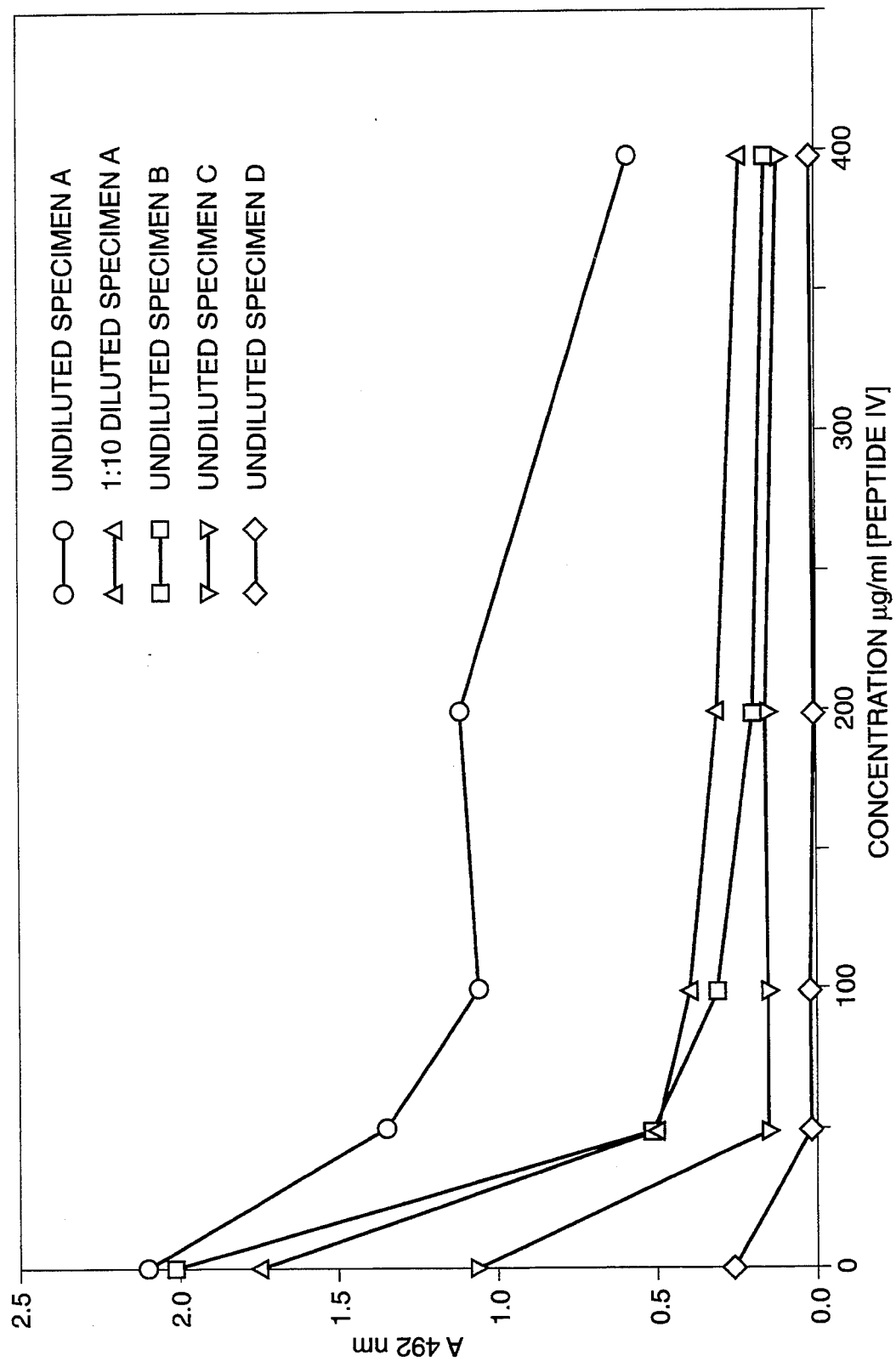
FIG. 9 illustrates the inhibition by Peptide IV (an analogue) of binding of HCV specific antibodies to plates coated with peptides IID and IIIF at 5 ug/mL each at various peptide Iv concentrations.

200 uL of the peptide IV neutralized specimens were then added to each of the wells and allowed to react for 15 minutes at 37°, followed by the EIA procedure as described in Example 2. Four representative reactive samples including two weakly reactives and two strongly reactives were tested. One of the strong reactives was further diluted at 1:10 in the specimen diluent prior to neutralization testing. As shown in FIG. 9 and Table 4, a dose dependent inhibition [or neutralization] of HCV EIA was observed with peptide IV. When compared with the controls, a significant inhibition was obtained with all four specimens even at a concentration of 50 ug/mL peptide IV.

EXAMPLE 12

Detection of Antibodies to HCV in Hemodialysis patients by EIA

A coded panel consisting of 74 samples from a group of hemodialysis patients was tested in two types of EIAs using plates coated with a mixture of HCV peptides IIH and V at 10,5 ug/mL or a recombinant HCV protein based EIA. The panel was provided by investigators at the Japanese National Institute of Health and the results were decoded and compared to the recombinant HCV protein based EIA by the sera provider.

Figure 10:
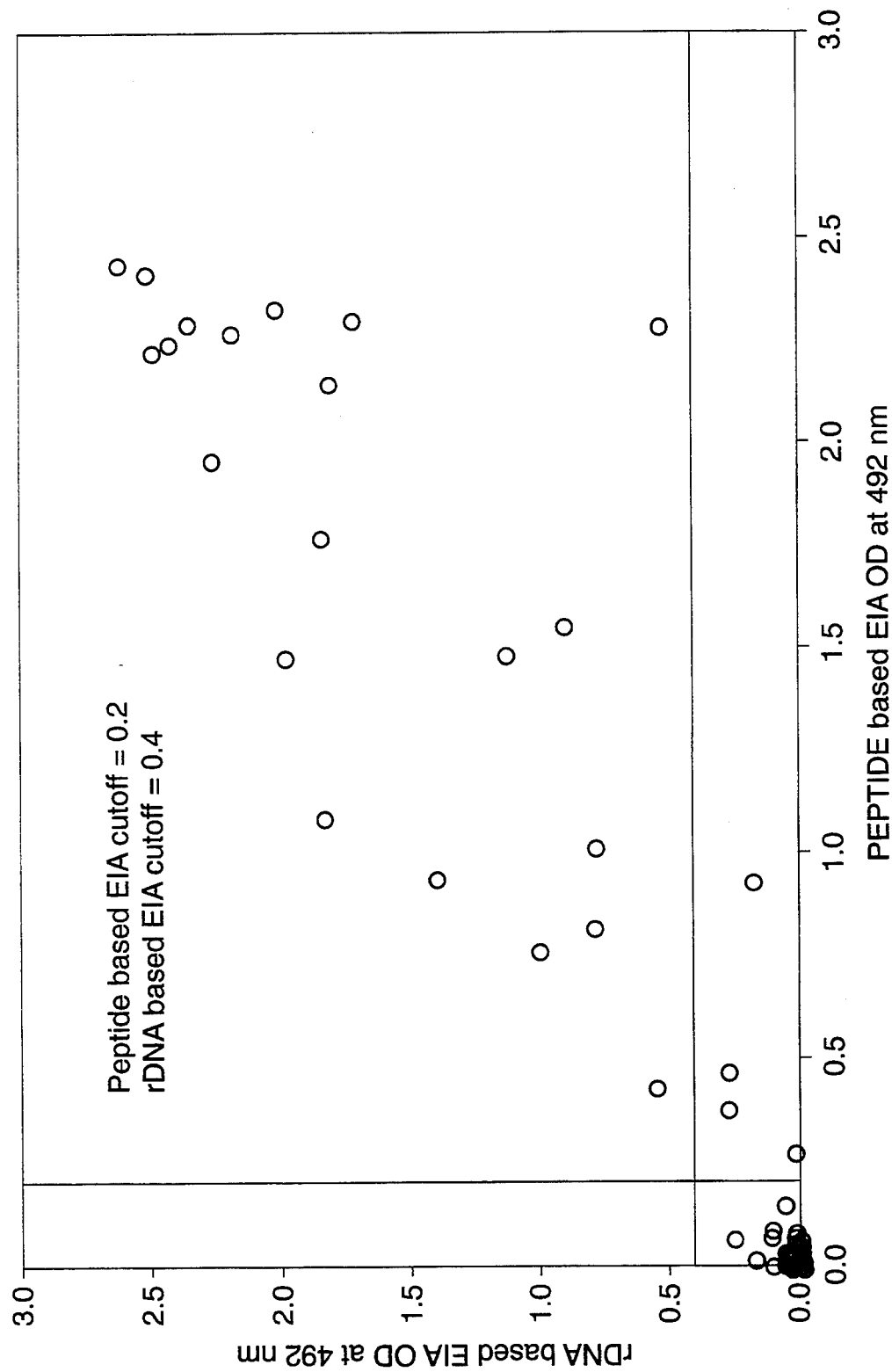
FIG. 10 provides a comparison between the peptide based HCV EIA (coated with Peptide IIH and V at 10 and 5 ug/mL respectively) and recombinant protein based HCV EIA using samples from 74 hemodialysis patients, kindly provided by investigators at the Japanese National Institute of Health.

As shown in FIG. 10, an x-y plot of the A492 nm readings for the peptide based HCV EIA and the recombinant HCV protein based HCV EIA revealed a high correlation between these two assays. (A cutoff value of 0.2 and 0.4 was obtained based on the corresponding assay design.) These 74 specimens obtained from the hemodialysis patients who are highly susceptible to HCV infection were grouped into four categories based on their respective reactivities with these two types of EIAs. The upper right block indicates samples that are scored positive by both assays, and the lower left block indicates samples that: are scored negative by both assays. None of the 74 high risk samples were found positive by the recombinant based EIA and negative by the peptide based EIA as shown in the upper left block; whereas five of these 74 high risk samples scored positive by the peptide based EIA and negative by the recombinant based EIA as shown in the lower right block indicating that the peptide based HCV EIA is more sensitive when tested with specimens derived from patients at high risks for HCV infection.

EXAMPLE 13

Detection Of Anti-HCV Activity In Rare Specimens With An Elevated ALT Level

These results are representative of the acute phase of HCV infection by synthetic peptides of Peptide VII series, covering a region near the C-terminus of the HCV protein C-100, and Peptide IIH from the immunodominant region.

Wells or 96-well plates were coated at 37° C. for 1 hour with each of the six peptides VIIA, VIIB, VIIC, VIID, IIG and IIH, at 5 ug/mL at 100 uL per well in 10 mM NaHCO$_3$ buffer, pH 9.5. Each peptide's immunoreactivity with the respective specimen was measured as previously described in Example 1. As shown in in Table 5, weak immunoreactivity was obtained with specimen 3 for peptides VIIC and VIID, but not VIIA and VIIB. Moderate immunoreactivity was obtained with specimen NAB-2-2 for peptide IIH, but not IIG. Both specimens were found to have high ALT level and are representative of specimens from patients with acute phase of HCV infection.

TABLE 4

| | | Peptide Based HCV Neutralization EIA As A Confirmatory Test | | | | | | | | |
|---|---|---|---|---|---|---|---|---|---|---|
| | | Peptide IV Concentration | | | | | | | | |
| Specimens | | 400 ug/mL | | 200 ug/mL | | 100 ug/mL | | 50 ug/mL | | Control |
| ID | Dilution | mA | % I | mA | % I | mA | % I | mA | % I | mA |
| A | 1:1 | 590 | 72.0 | 1129 | 46.5 | 1066 | 49.5 | 1363 | 35.4 | 2111 |
| | 1:10 | 244 | 86.1 | 325 | 81.5 | 409 | 76.7 | 510 | 71.0 | 1762 |
| B | 1:1 | 161 | 92.0 | 209 | 89.6 | 321 | 84.1 | 523 | 74.1 | 2021 |
| C | 1:1 | 117 | 89.0 | 162 | 84.7 | 155 | 85.4 | 153 | 85.6 | 1064 |
| D | 1:1 | 27 | 89.8 | 23 | 91.3 | 38 | 85.7 | 34 | 87.2 | 266 |

$$\% \text{ INHIBITION} = \frac{mA(\text{control}) - mA(\mu g/mL)}{mA \text{ (control)}}$$

TABLE 5

| Code | Amino Acid Sequence | A492 nm Specimen No. NAB-2-2 #3 |
|---|---|---|
| IIH | SG, KPAII, PDREV, LYREF, DEMEE, CSQHL, PYIEQ, GMMLA, EQFKQ, KALGL | 1.232(+) |
| IIG | II, PDREV, LYREF, DEMEE, CSQHL, PYIEQ, GMMLA, EQFKQ, KALGL | 0.013(−) |
| VIIA | AVQWM, NRLIA, FASRG, NHVSP | 0.109 |
| VIIB | RHV, GPGEG, AVQWM, NRLIA, FASRG, NHVSP | 0.224 |
| VIIC | V, VCAAI, LRRHV, GPGEG, AVQWM, NRLIA, FASRG, NHVSP | 0.674 |
| VIID | PGA, LVVGV, VCAAI, LRRHV, GPGEG, AVQWM, NRLIA, FASRG, NHVSP | 0.658 |

EXAMPLE 14

Measurement Of Relative (%) Immunoreactivity For Synthetic Peptide Covering An Immunodominant Region Of The Postulated HCV Core Protein By An Enzyme-Linked Immunosorbent Assay Wells of 96-well plates were coated at 4° C. overnight (or 1 hour at 37° C.), with each of the ten peptides: VIIIA, VIIIB, VIIIC, VIIID, VIIIE(=VIII), IXA, IXB, IXC, IXD, and IXE(=IX), (see Table 7) prepared as described at 5 ug/mL at 100 uL per well in 10 mL NaHCO3 buffer, pH 9.5. The rest of the plate coating and enzyme immunoassay procedures were performed exactly as described in Example 1.

Figures 1, 11:
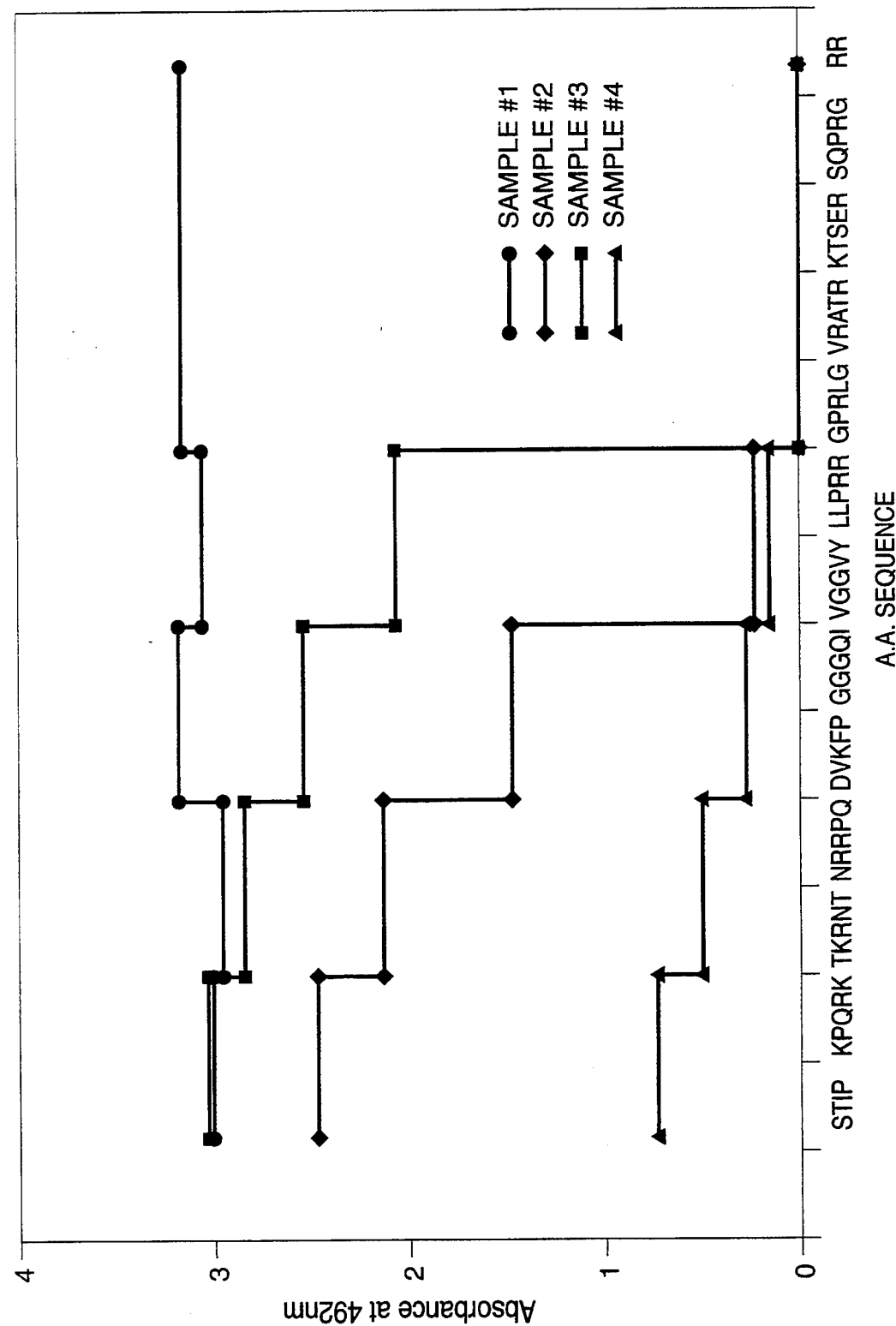
Figures 2, 11:
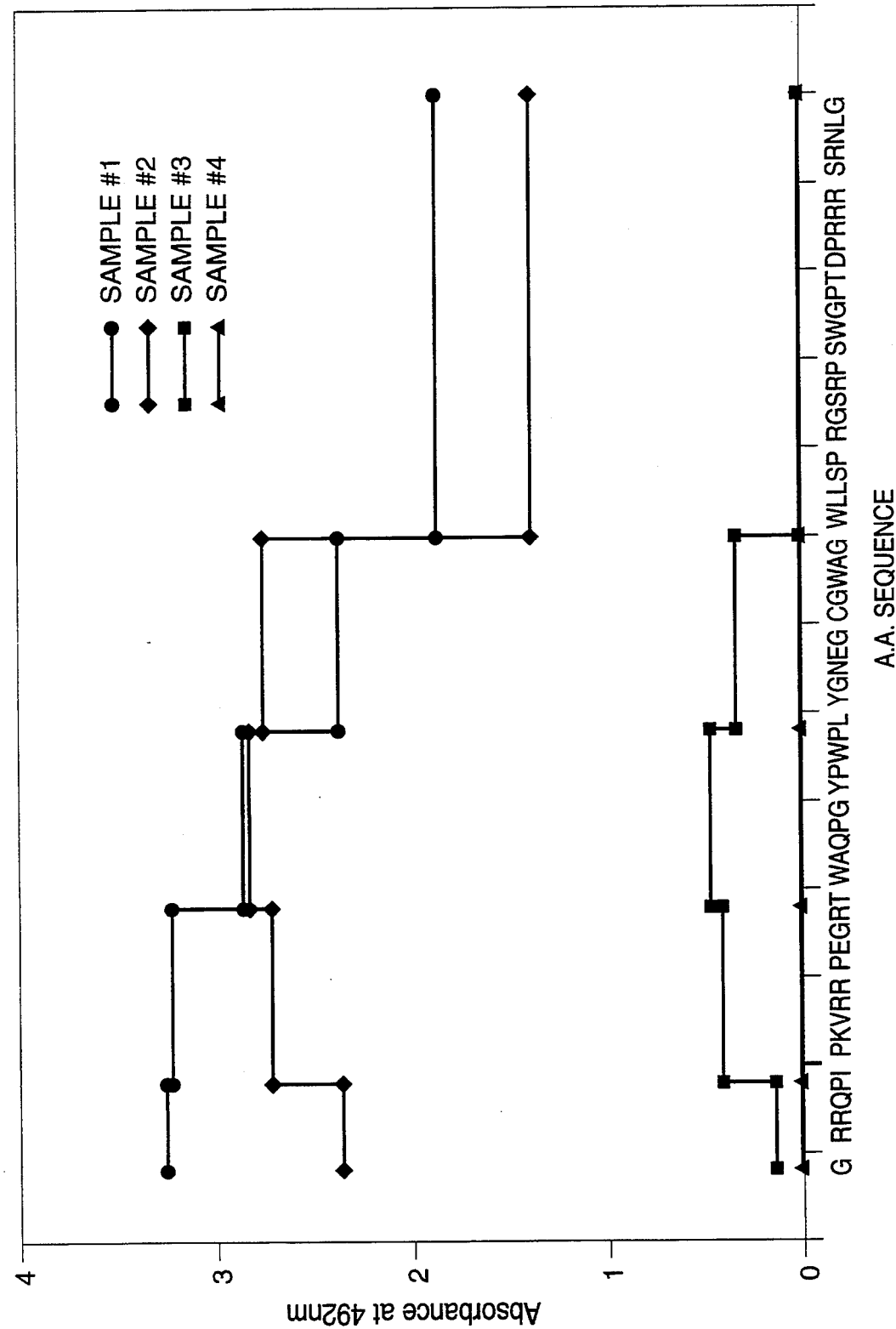
Figures 1, 12:
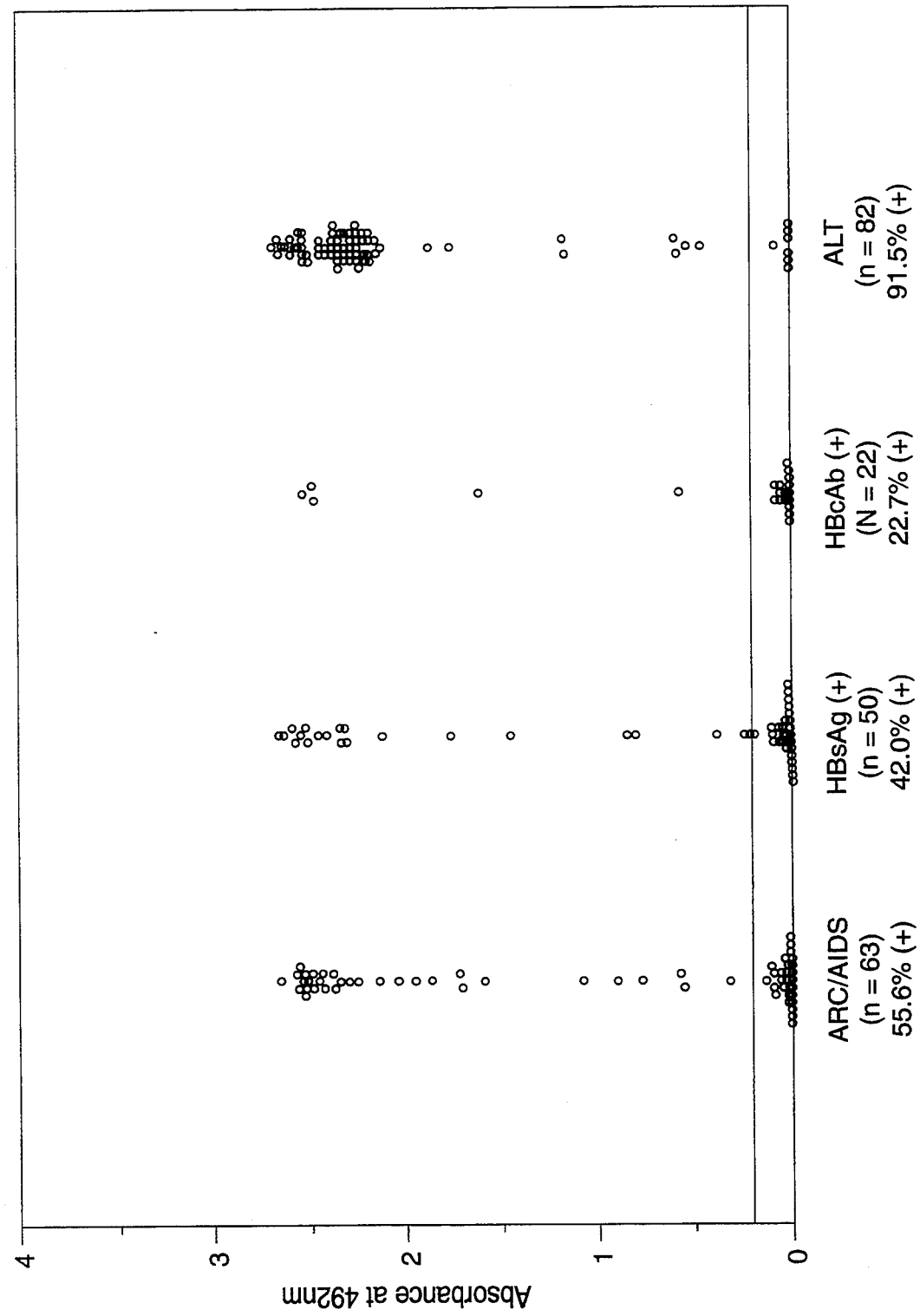
Figures 2, 12:
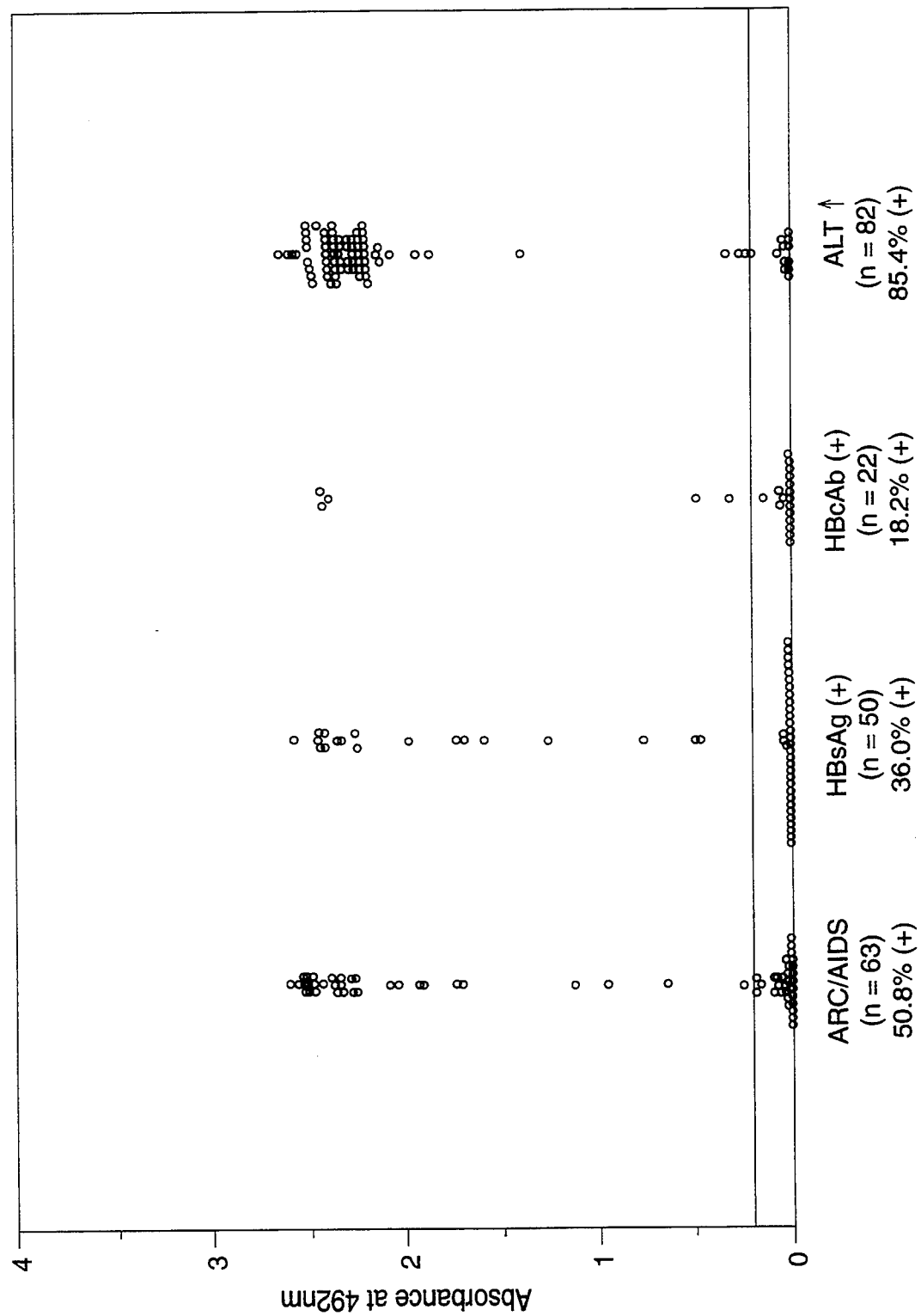
Figures 3, 12:
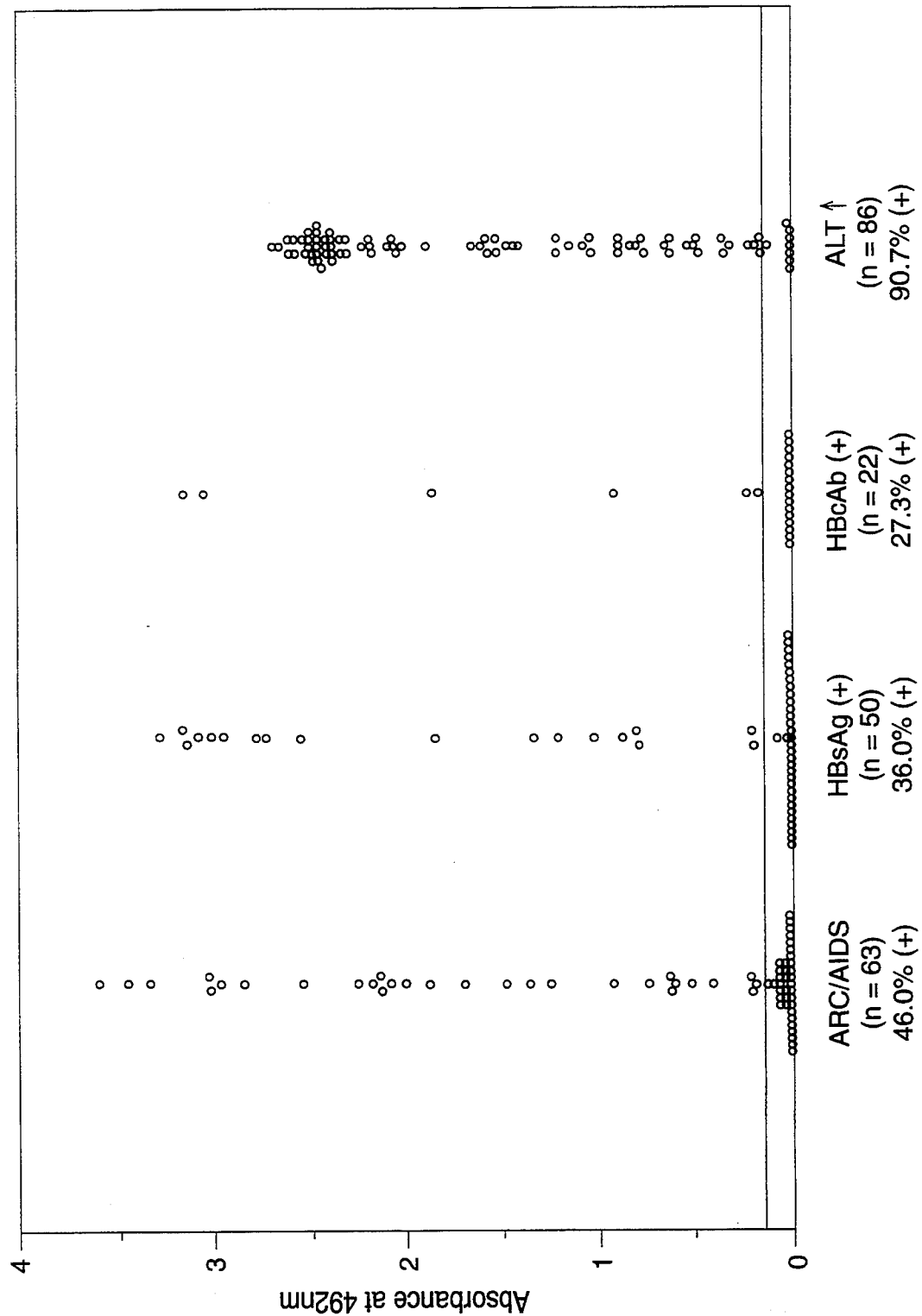

Results obtained from this study are shown in FIGS. 11-1 and 11-2. According to the EIA absorbance readings at 492 nm (y axis) and the amino acid sequences for each of the corresponding HCV peptides (x axis), representative immunoreactivity profiles are plotted for four of the eight panel sera as shown in FIGS. 11-1 and 11-2. Relative (%) immunoreactivity index for each of the 10 peptides (Table 7) is calculated against Peptide IIID (See Table 1), the one with the highest absorbance reading, based on the total absorbance of eight sera at 492 nm (See Tables 1 and 2 for examples of calculation). FIGS. 11-1 and 11-2 show the amino acid sequences of the immunodominant region according to data obtained for immunoreactivity study. For example, serum sample 1 reacted strongly (ODs between 1.5 and 3.5) with peptides VIIIA and IXA, which are the smallest size in the 20 mer range in the corresponding peptide series. Further addition of amino acids at the N-terminal end did not significantly enhance the immunoreactivity of these analogue peptide (see FIGS. 11-1 and 11-2 for sample 1).

However, other serum samples such as #3 and #4 reacted much stronger with peptides VIIIB, VIIIC respectively and with an increasing immunoreactivity with the analogue peptides in the IX series (see FIGS. 11-1 and 11-2, samples #3 and #4). Further, serum sample 2 reacted marginally with peptides in the corresponding VIII and IX series. These reactivity profiles indicate a more complicated epitope distribution along the postulated HCV core protein region and may include some discontinuous linear epitopes and conformational epitopes, requiring a longer size peptide to confer the best immunoreactivity for diagnostic purposes.

In summary, epitope mapping analysis conducted with a series of ten peptides covering an immunodominant region of the postulated HCV core protein, spanning a total of 119 amino acid residues as illustrated in Table 7 and FIGS. 11-1 and 11-2, reveals varying degrees of immunoreactivity between different HCV antibody positive serum samples and analogue HCV Peptides of the VIII and IX series. In this case it is found preferably to have synthetic peptides with longer amino acid chains, ideally longer than 20, to optimally present these antigenic determinants to HCV antibodies.

Based on the above-mentioned epitope mapping study, additional representative EIAs using Peptides VIIIE, IXD, both derived from the HCV core region alone, or as a mixture with peptides IIH and V from the HCV nonstructural region were configured for the following studies described in Examples 15, 16, 17 and 18.

EXAMPLE 1

Detection Of Antibodies To HCV By Peptide Based Enzyme-Linked Immunosorbent Assay Using Format C, Format D, Format A The following four groups of specimens:
(a) individuals with AIDS, ARC(n=63);
(b) individuals positive for HBsAg, (n=50);
(c) individuals positive for antibodies to HBc protein, (n=22); and
(d) individuals with elevated (>100 i.u./L) alanine aminotransferase (ALT) enzyme activity, (n=86).

were analyzed on representative HCV peptide based EIAs according to the present invention, with the plates coated either with (i) peptides IIH and V at 5 and 3 ug/mL each (Format A), (ii) peptides IIH, V and VIIIE at 5, 3 and 2 ug/mL each (Format C, containing both the HCV core and nonstructural peptides) or (iii) Peptides VIIIE and IXD at 2 and 2 ug/mL each (Format D, HCV core peptides only).

Results obtained from the screening of a total of 221 well-characterized clinical specimens previously categorized into four groups, from (a) to (d) using a representative lot of peptide coated plates EIAs formatted as A, C or D were plotted on histograms as shown in FIGS. 12-1, 12-2 and 12-3.

Out of a total of 63 AIDS/ARC patient samples analyzed, 46.0%, 55.6% and 50.8% of the patients were found to be HCV antibodies positive using EIA formats A, C and D respectively. Out of 50 HBsAg positive individuals, 36.0%, 42.0% and 36% of the individuals were found to also be HCV antibodies positive using EIA formats A, C and D respectively. Out of 22 HBc antibody positive individuals, 27.3%, 22.7%, and 18.2% were found to be HCV antibodies positive as detected by EIA formats A, C and D. Out of 86 patients with an elevated ALT levels, 90.7%, 91.5% and 85.4% were found to be HCV antibodies positive by EIA formats A, C and D. The overall signal to noise ratio distribution for the HCV positive samples were found to be higher with Formats C and D which included a peptide (VIIIE) from the HCV core region than Format A which only employed peptides from the HCV nonstructural region as the solid phase antigen.

Except for one HBc antibody sample where the results is borderline positive (S/cutoff ratio ~ 1.0) with the HCV EIA Format A, Format C incorporating peptides (IIH, V and VIII from both the HCV structural (core) and nonstructural regions was the most sensitive. The significant improvement in sensitivity makes Format C an ideal candidate for a HCV antibody screening assay.

EXAMPLE 16

Comparison Of Test Results Using The Three Peptide Based HCV EIA Formats (A,C And D) On Low Risk Random Blood Donors Representative 264 donor specimens obtained in a blood bank setting were tested by all three EIA formats.

Figures 1, 13:
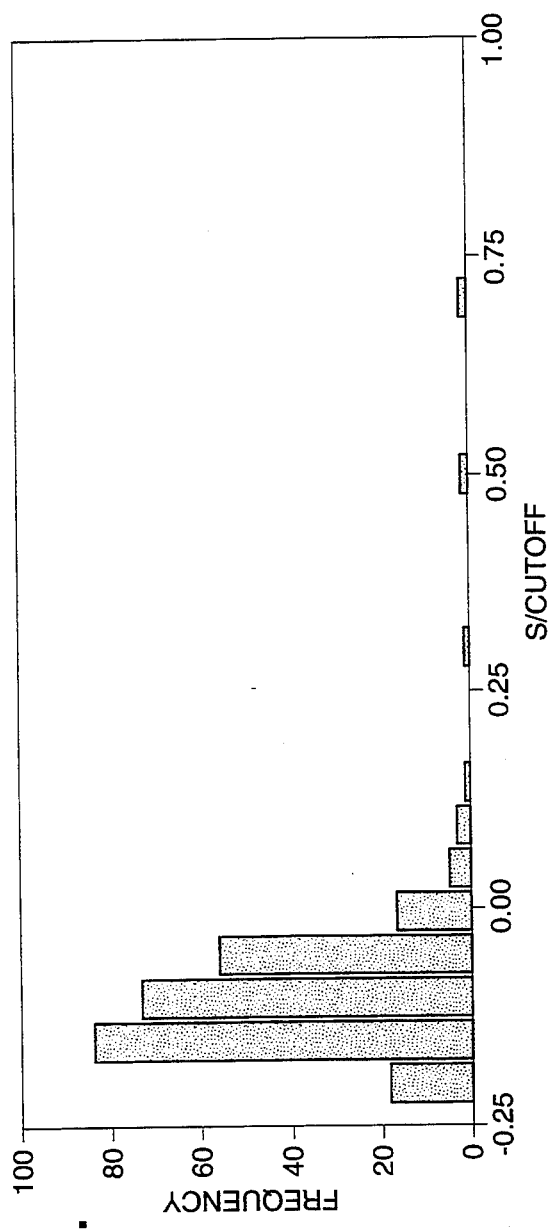
Figures 2, 13:
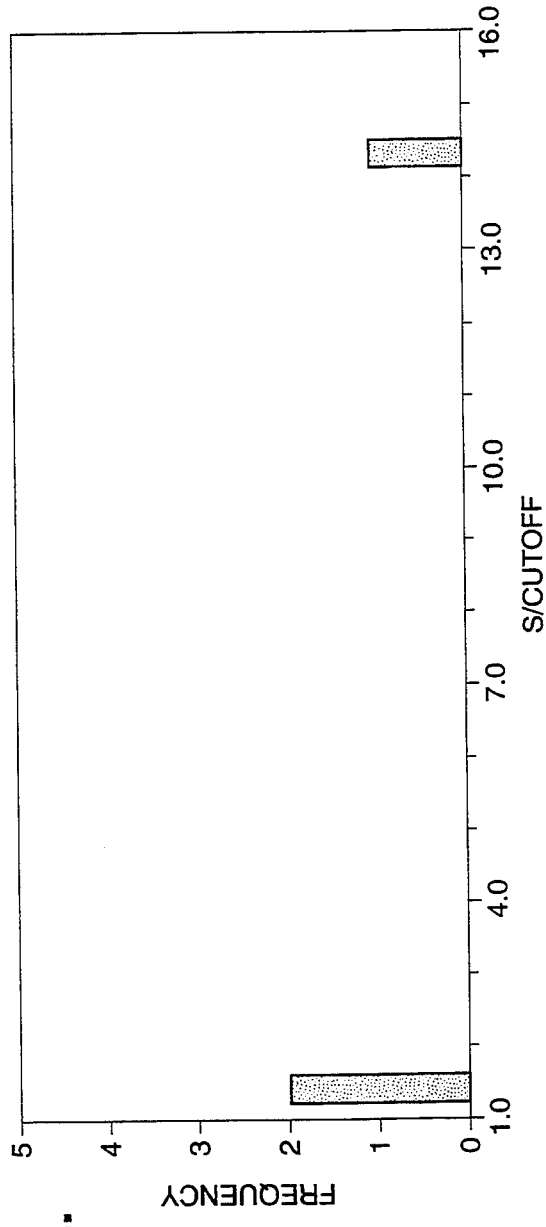
Figures 3, 13:
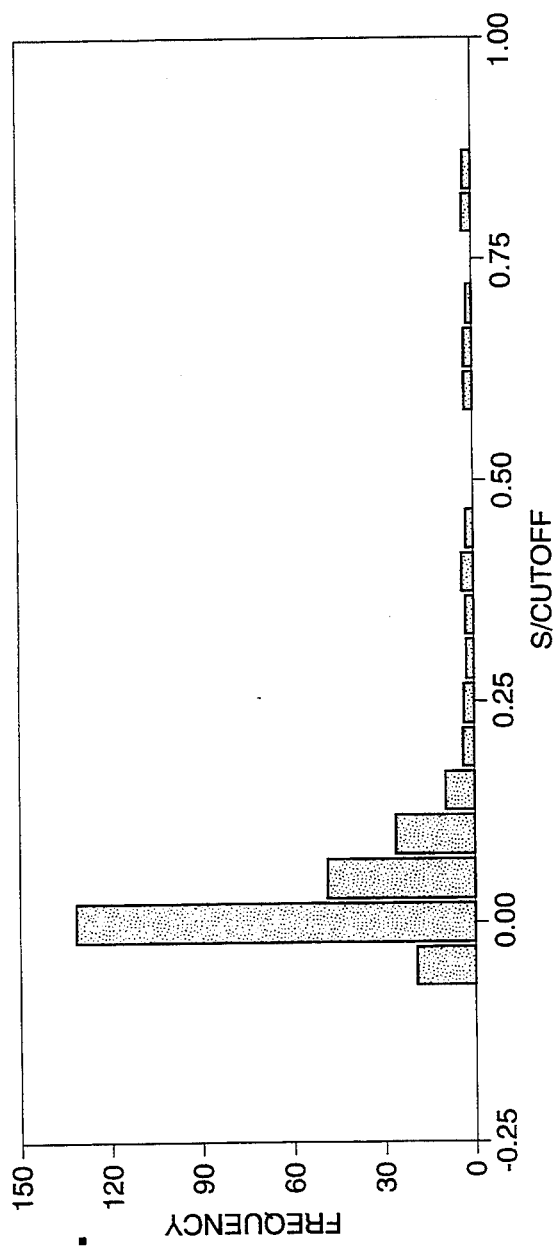
Figures 4, 13:
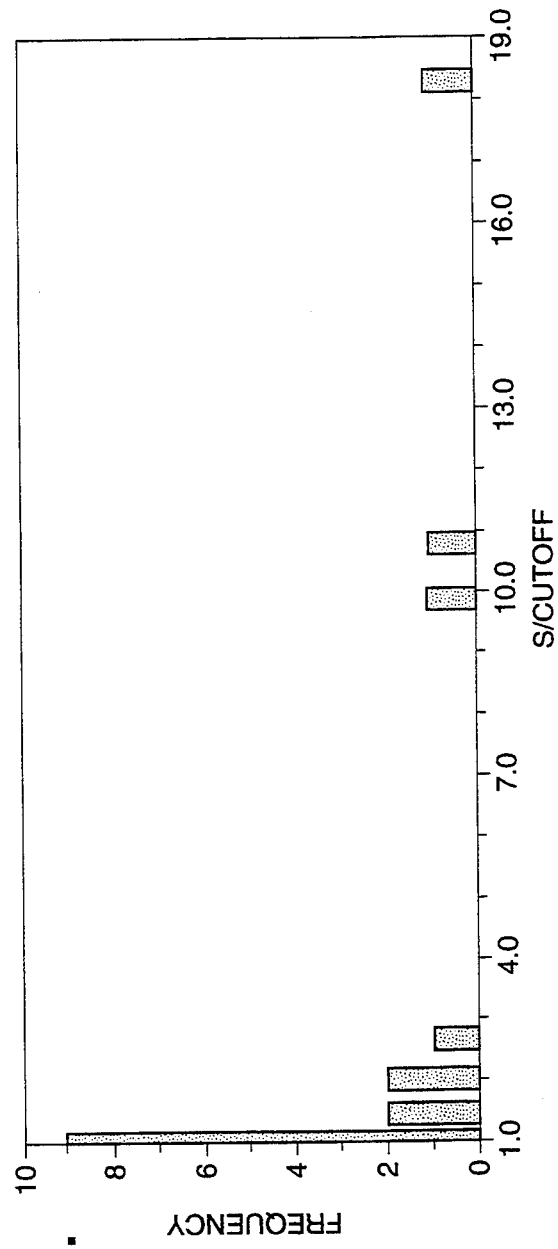
Figures 5, 13:
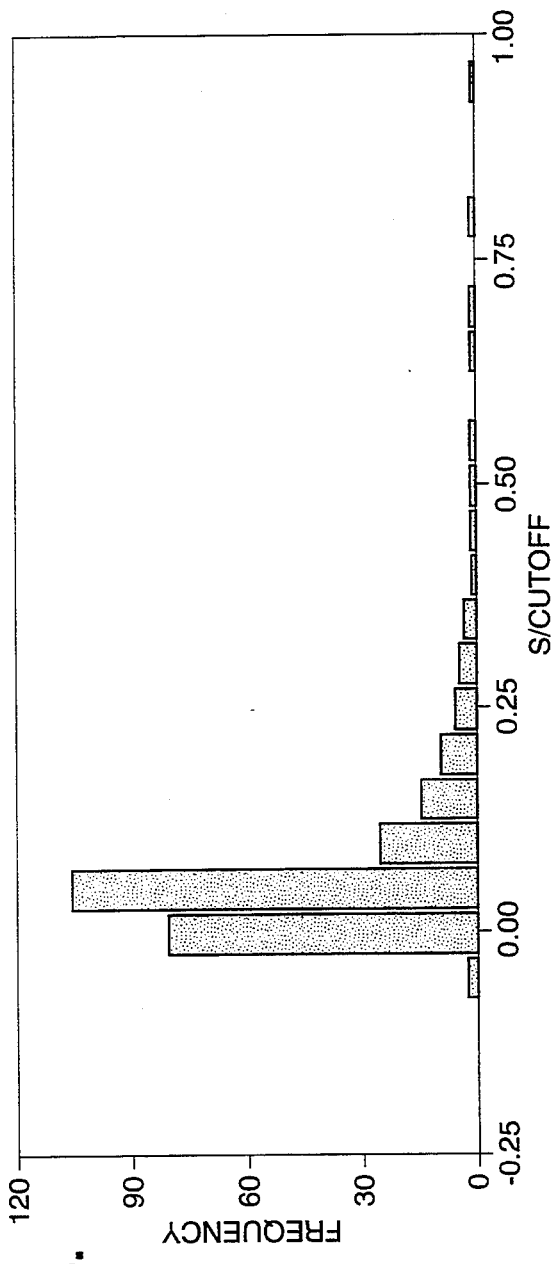
Figures 6, 13:
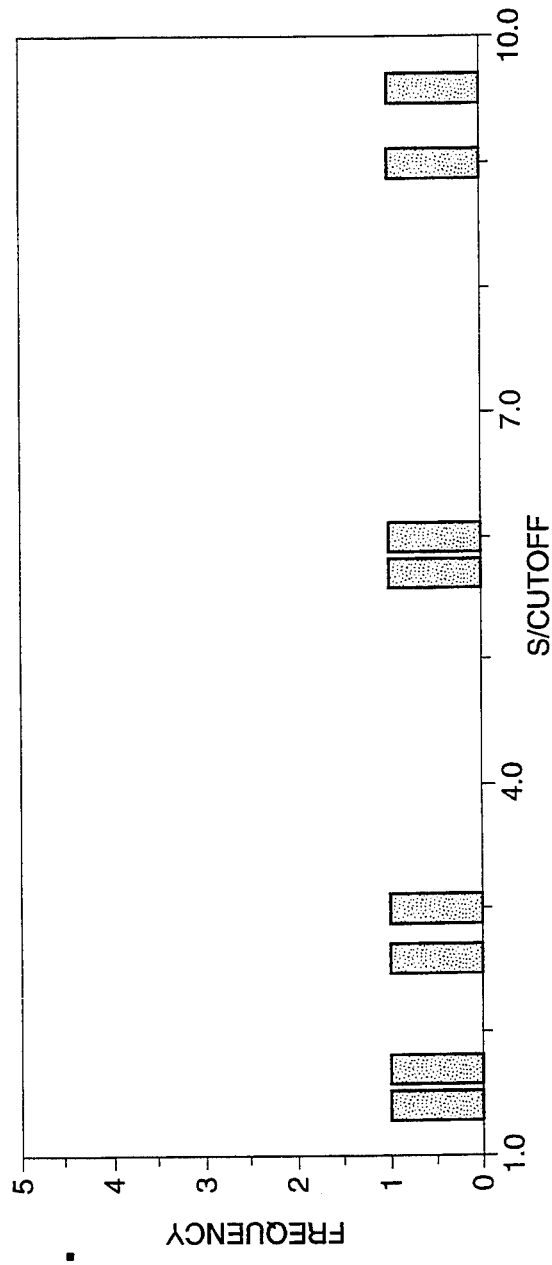

The results are shown in FIGS. 13-1 to 13-6. The frequency distributions of the peptide based HCV-EIA signal to cutoff ratios suggested an initial reactive rate of 1.13%, 3.0% and 3.0% with formats A, C and D respectively. The negative samples have a relative low signal to cutoff ratio in all three assay formats(see FIGS. 13-1, 13-3, and 13-5). Upon repeat testing, a repeatably reactive rate of 1.13%, 1.9% and 1.9% were obtained for formats A, C and D respectively. Among the sera identified as positives, there were four specimens which reacted strongly with both Formats C and D, but were identified as negatives by Format A. This indicates the possibility of false negative results when an HCV antibody detection assay does not include epitopes from the structural protein region.

EXAMPLE 17

Detection Of Antibodies To HCV In Well-Characterized Serial Samples By Various Enzyme-Linked Immunosorbent Assays (a) A coded panel consisting of 24 samples derived from a case of transfusion transmitted NANBH were tested in three HCV EIA formats (A, B and C) to determine the respective sensitivity of the formats in detecting seroconversion. The panel was provided by Dr. H. Alter of NIH and the results were decoded by his laboratory.

Figures 1, 14:
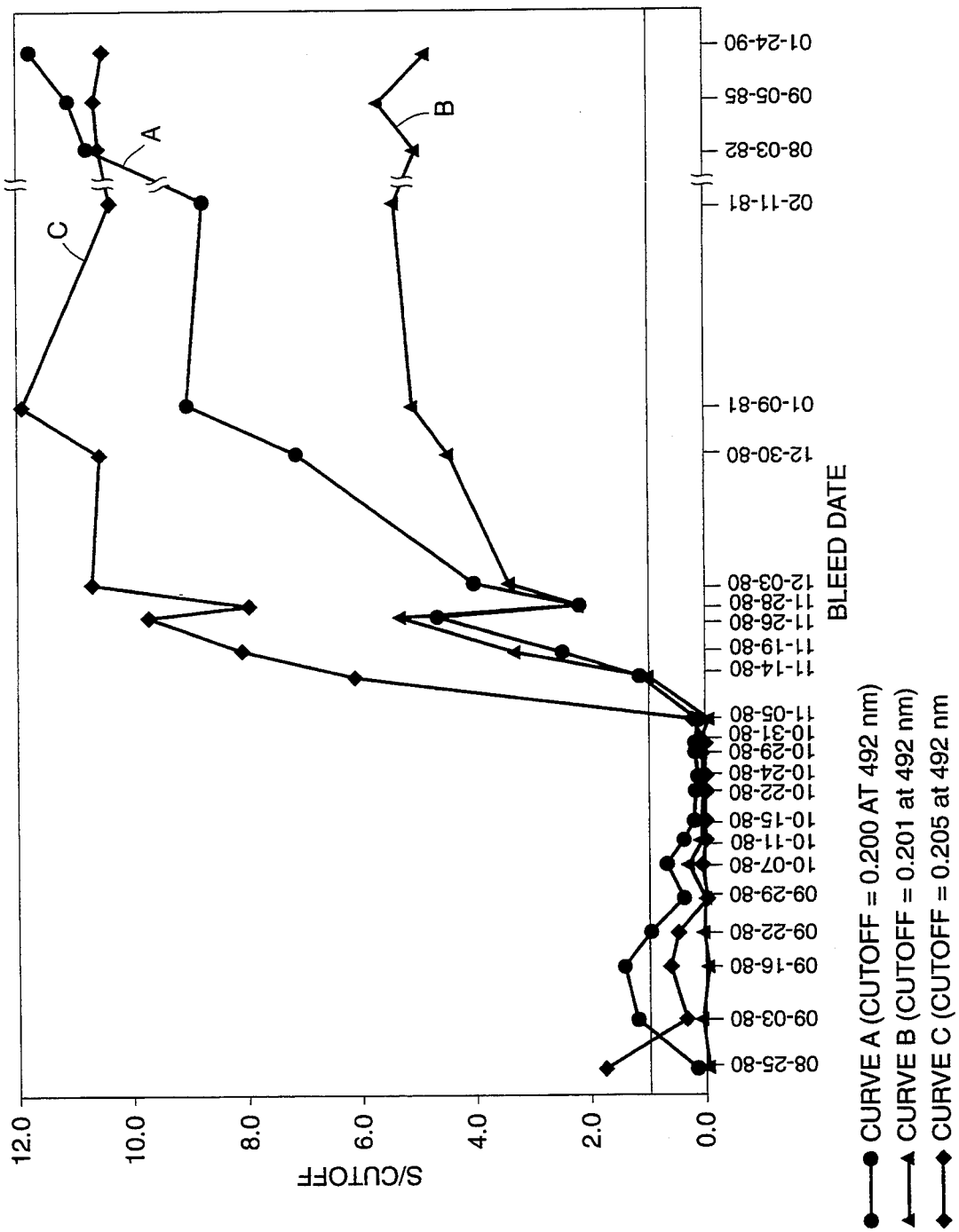
Figures 2, 14:
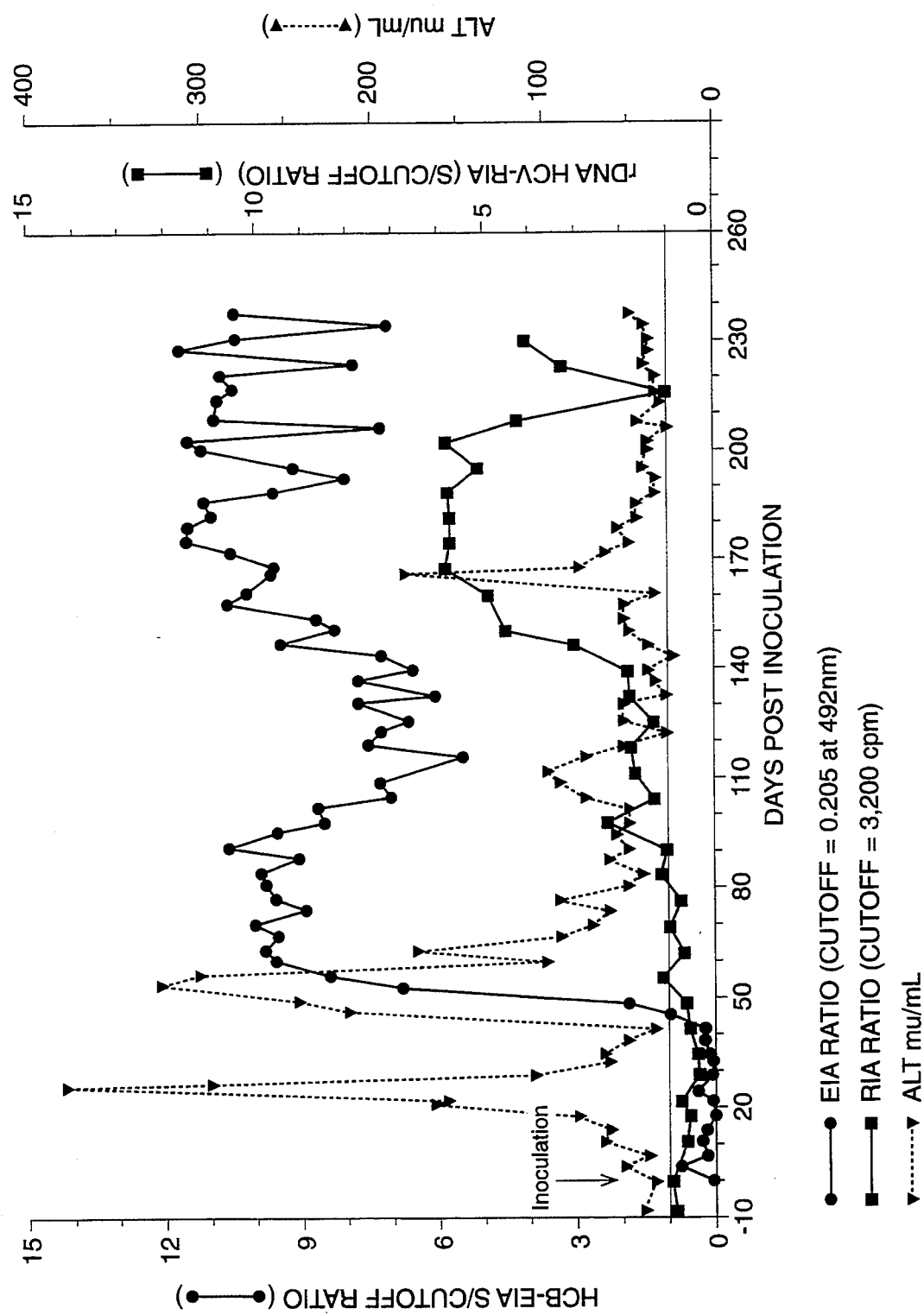

As shown in FIG. 14-1, the three anti-HCV profiles, as tested by three formats using peptides IIF/IIID/V coated plate. (Curve A); Peptides IIF/IIID coated plate (Curve B); and peptides IIH, V and VIIIE coated plate (Curve C) respectively, with sera spanning a ten year period revealed an interesting contrast.

As a result of the transfusion, a trace amount of passive HCV antibodies was detected in the recipient's serum by both format A, and C. Active development of HCV antibodies by the recipient became detectable by all three formats from November 14th on (about three months after the initial transfusion), with format C having the highest S/cutoff ratio on that bleed date. This finding further confirms the improved sensitivity ,obtained by using HCV EIA format C.

(b) Serial samples from a representative chimpanzee were tested with HCV EIA format C in comparison to a recombinant HCV C-100 based radioimmunoassay (RIA). The chimpanzee was inoculated on day 0 with a well-characterized strain of NANBHV. Following the acute phase of infection as evidenced by the rise of the ALT levels, antibodies to HCV were detected about 47 days after inoculation (FIG. 14-2). HCV EIA Format C was able to detect HCV antibodies about 40 days early than the the rDNA based RIA. A higher signal to cutoff ratio was obtained with HCV EIA Format C than the rDNA RIA.

(c), Serial samples from three well-characterized representative HCV seroconversion panels, collected by Serologic Inc., were tested by HCV EIA formats A, C and D, as defined in Example 15 in addition to that previously tested with rDNA HCV C-100 based EIA. As shown in Table 8, both HCV EIA formats C and D were able to identify HCV antibody positive specimens in two out of three panels by four to eight weeks earlier than the rDNA HCV-100 based EIA and HCV EIA Format A. This further demonstrated the sensitivity of the HCV EIAs which incorporate peptides derived from the HCV structural (core) protein region.

EXAMPLE 18

Detection Of Antibodies To HCV In Hemodialysis Patients By Various Forms Of HCV EIAs A coded panel consisting of 74 samples from a group of hemodialysis patients was tested by three types of HCV EIAs; a recombinant HCV protein based EIA, and two using plates coated with either a mixture of HCV peptides IIH and V at 10, 5 ug/mL respectively (Format A), or a mixture of HCV peptides IIH, V and VIIIE at 5, 3 and 2 ug/mL respectively (Format C). The panel was provided by investigators at the Japanese National Institute of Health. Results were decoded and compared to the recombinant HCV protein based EIA by the sera provider.

Figures 1, 15:
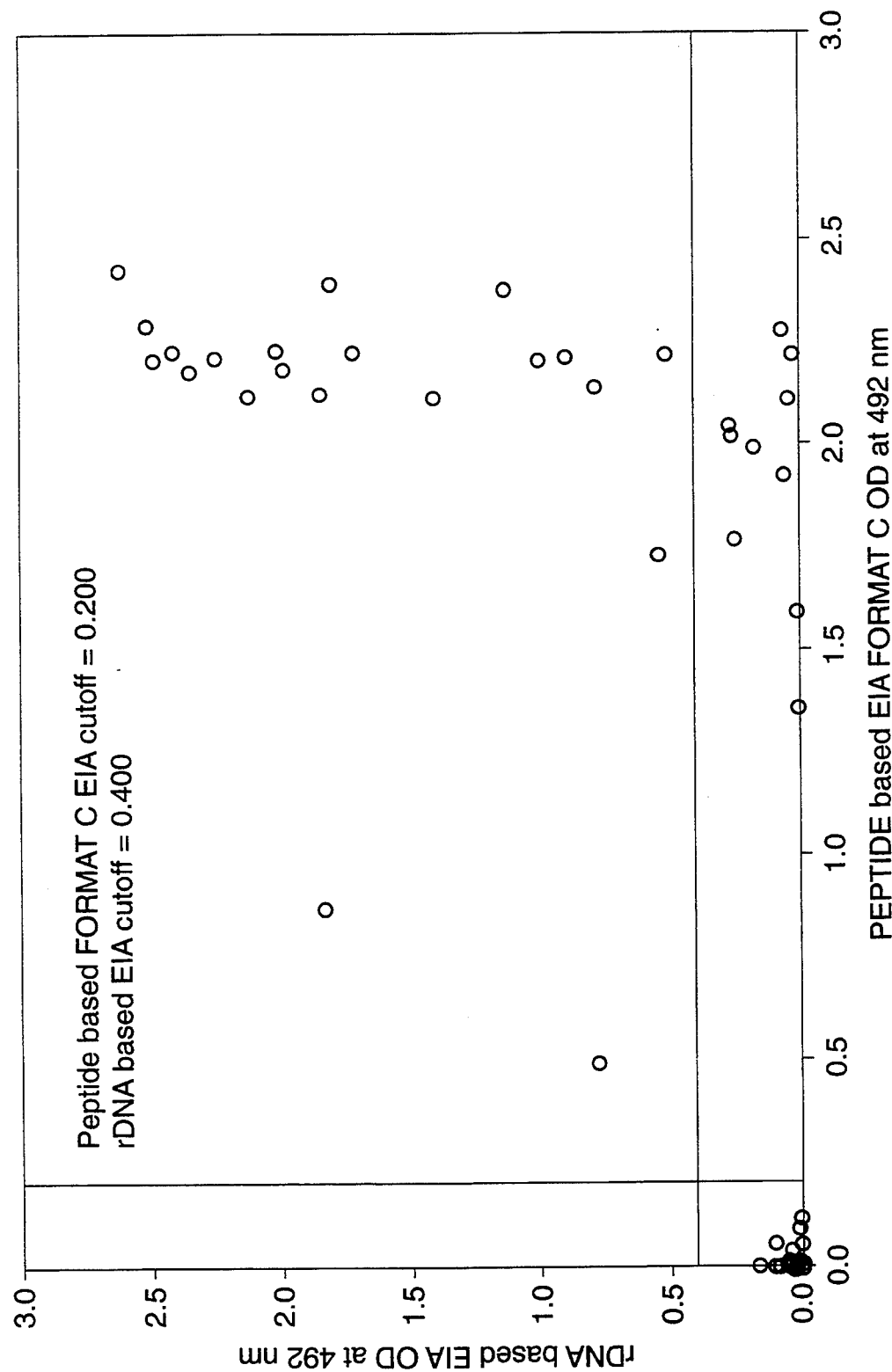
Figures 2, 15:
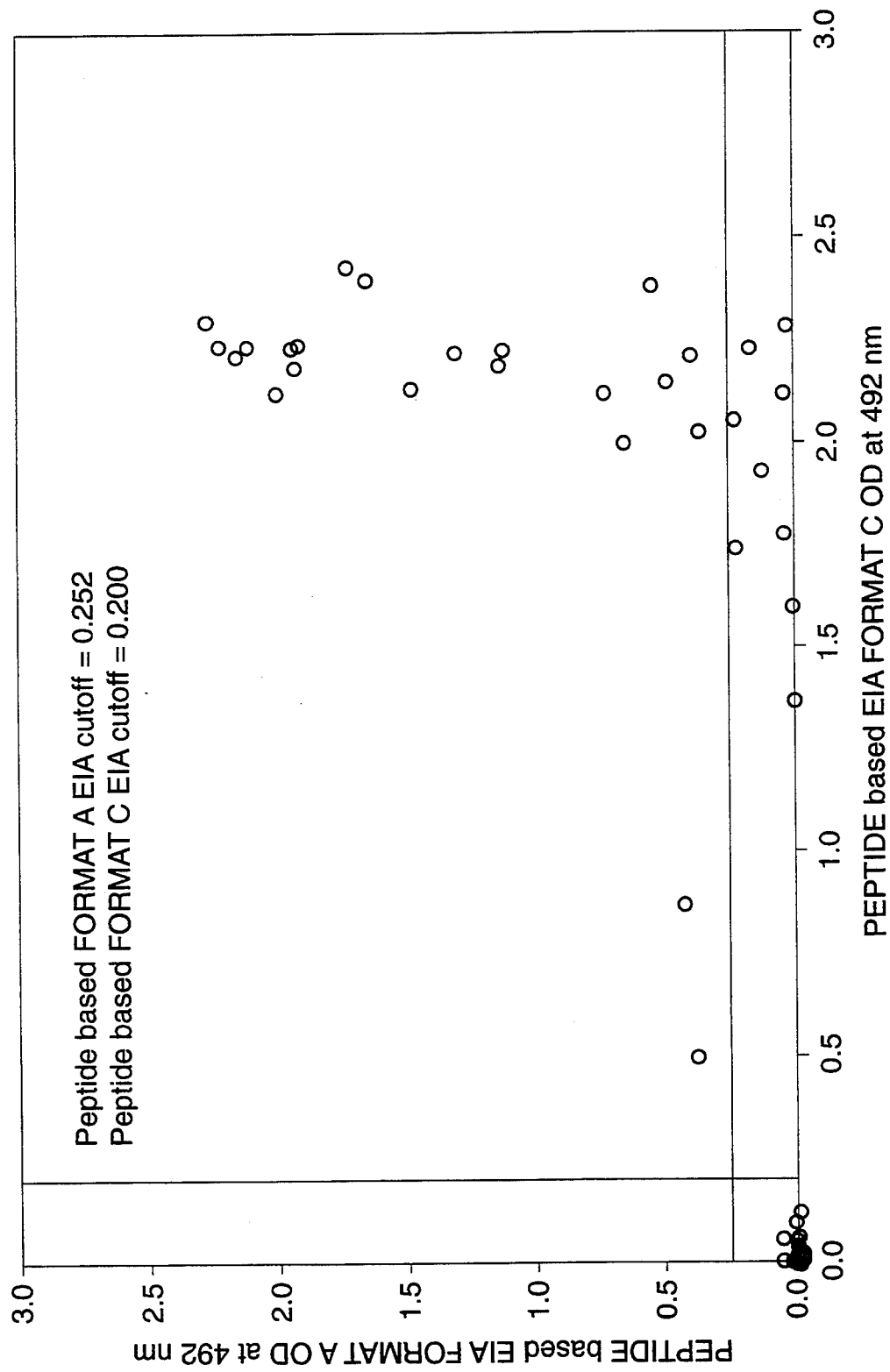

As shown in FIG. 15-1, an x-y plot of the A492 nm readings for the peptide based HCV EIA Format C and the recombinant HCV protein based HCV EIA revealed an increased sensitivity with the peptide based HCV EIA format C when compared to the rDNA HCV C-100 protein based HCV EIA. (A cutoff value of 0.2 and 0.4 was obtained based on the corresponding assay design). These 74 specimens obtained from dialysis patients who are highly susceptible to HCV infection were grouped into four categories based on their respective reactivities with these two types of EIAs. The upper right block indicates samples that were scored positive by both and the lower left block indicates samples that were scored negative by both assays. None of the 74 high risk samples were found positive by the recombinant based EIA and negative by the peptide based EIA as shown in the upper left block; whereas "eleven" of these 74 high risk samples scored positive by the peptide based EIA Format C and negative by the recombinant based EIA as shown in the lower right block.

An increase in sensitivity was obtained for the peptide based HCV EIA Format C (incorporating a HCV core peptide) when compared to HCV EIA Format A, which in turn showed an improved sensitivity compared with the recombinant HCV-C100 protein based EIA (see Example 12, FIG. 10).

To further document the validity of such a sensitivity comparison, other clinical data obtained for each of the dialysis patient specimens were tabulated along with the corresponding EIA ratios (Table 9). Among the eleven marked specimens, most showed an increased level of GOT/GPT and were associated with frequent episodes of elevated GPT previously. All eleven specimens scored negative by the rDNA HCV C-100 based EIA. However, these same samples reacted strongly (with O.D.~1.5) in the peptide based HCV EIA Format C. Since peptide VIII=VIIIE) was synthesized according to amino acid sequences selected from the conserved structural (core) protein region, its inclusion in the peptide based HCV EIA (such as format C) will be particularly suitable when testing specimens from geographically distinct regions where a higher chance of strain-to-strain variation among the HCV isolates may be encountered.

It is to be understood that the above examples are illustrative of the present invention and are not meant to limit the scope thereof.

TABLE 8

Testing of Various Formats of HCV EIAs with Three Well-Characterized Seroconversion Panels

| Panel | Donor # | Bleed Date | ALT I.U./L | AST I.U./L | rDNA HCV c-100 | HCV EIA Format A (ns) | HCV EIA Format C (core + ns) | HCV EIA Format D (core) |
|---|---|---|---|---|---|---|---|---|
| Panel 1 | 02190D | 880809 | 40.0 | NA | 0.03 | 0.093 | 0.108 | 0.205 |
| | | 880816 | 32.0 | NA | 0.04 | −0.014 | 0.045 | 0.129 |
| | | 880823 | 32.0 | NA | 0.06 | −0.050 | 0.025 | 0.072 |
| | | 880830* | 180.0 | 121.0 | 0.04 | −0.050 | 1.037* | 1.096* |
| | | 880928 | 401.0 | 352.0 | 0.19 | 0.100 | 7.193 | 7.703 |
| | | 881109* | NA | NA | 6.57* | 16.700* | 10.185 | 7.281 |
| | | 881122 | NA | NA | 6.57 | 16.671 | 9.770 | 9.321 |
| Panel 2 | 00269B | 880815 | 39.0 | NA | 0.0 | 0.014 | −0.058 | −0.008 |
| | | 880825 | 274.0 | 310.0 | 0.0 | 0.443 | 0.058 | 0.108 |

TABLE 8-continued

Testing of Various Formats of HCV EIAs with Three Well-Characterized Seroconversion Panels

| Panel | Donor # | Bleed Date | ALT I.U/L | AST I.U./L | rDNA HCV c-100 | HCV EIA Format A (ns) | HCV EIA Format C (core + ns) | HCV EIA Format D (core) |
|---|---|---|---|---|---|---|---|---|
| | | 880829 | 346.0 | 270.0 | 0.0 | 0.029 | 0.128 | 0.185 |
| | | 880914 | 1175.0 | 722.7 | 6.5* | 4.057 | 7.835* | 5.984* |
| | | 881005 | 429.7 | 172.3 | 6.5 | 5.857 | 7.811 | 5.851 |
| Panel 3 | 20830D | 880829 | 63.0 | 65.0 | 0.04 | −0.043 | 0.115 | 0.181 |
| | | 880901* | 81.0 | NA | 0.04 | 0.043 | 1.607* | 1.108* |
| | | 880908 | 183.0 | 174.0 | 0.02 | −0.043 | 2.506 | 3.116 |
| | | 880928* | 563.0 | 555.0 | 6.57* | 3.800 | 9.827 | 9.659 |
| | | 881026 | 436.0 | 151.0 | 6.57 | 13.786 | 10.630 | 10.566 |

TABLE 9

HCV Positivity in Serum Specimens Obtained from Japanese Dialysis Patients

| Code No. | rDNA based HCA EIA OD Cutoff = 0.40 | Peptide based HCV EIA Format A Cutoff = 0.205 | Peptide based HCV EIA Format C Cutoff = 0.204 | HBsAb | GOT/GPT Oct, 89 | n: times during 1986–1988 when GPT >25 I.U./L |
|---|---|---|---|---|---|---|
| 24 | 0.058 | −0.001 | 0.005 | | 2/3 | 0 |
| 25 | 0.042 | 0.005 | 0.007 | | 9/9 | 0 |
| 26 | 0.105 | −0.001 | −0.003 | | 4/4 | 0 |
| 27 | 1.837 | 1.469 | 2.312 | − | 3/6 | 2 |
| 28 | 1.797 | 1.637 | 2.398 | − | 20/21 | 2 |
| 29* | 0.011 | 0.001 | 1.603 | | 7/4 | 0 |
| 30 | 0.994 | 0.374 | 2.213 | | 11/9 | 0 |
| 31 | 1.823 | 0.425 | 0.874 | − | 27/16 | 4 |
| 32 | 0.770 | 0.372 | 0.500 | + | 17/7 | 9 |
| 33 | 1.712 | 2.101 | 2.234 | − | 28/32 | 29 |
| 34 | 0.002 | −0.003 | 0.007 | | 11/14 | 0 |
| 35* | 0.026 | 0.161 | 2.229 | + | 14/23 | 23 |
| 36* | 0.065 | 0.018 | 2.286 | | 20/18 | |
| 37 | 0.021 | 0.000 | 0.011 | + | 16/11 | 1 |
| 38 | 2.347 | 1.917 | 2.182 | + | 26/23 | 6 |
| 39 | 0.008 | −0.007 | 0.004 | | 7/6 | 0 |
| 40 | 0.026 | 0.006 | −0.002 | | 10/8 | 0 |
| 41* | 0.061 | 0.118 | 1.933 | + | 9/6 | |
| 42 | 2.481 | 2.144 | 2.211 | − | 13/19 | 2 |
| 43 | 0.008 | −0.005 | −0.005 | + | 11/7 | |
| 44 | 0.009 | −0.004 | −0.005 | | 4/4 | 0 |
| 45 | 0.009 | 0.000 | −0.003 | | 7/2 | 0 |
| 46 | 2.177 | 1.990 | 2.121 | − | 16/12 | 8 |
| 47 | 0.023 | 0.003 | 0.015 | | 7/3 | 0 |
| 48 | 0.025 | −0.003 | 0.002 | + | 18/11 | |
| 49 | 0.025 | −0.001 | −0.006 | | 9/5 | 0 |
| 50 | 0.026 | 0.024 | −0.003 | | 9/3 | |
| 51 | 0.018 | −0.003 | −0.007 | + | 11/5 | |
| 52* | 0.011 | −0.003 | 1.366 | − | 33/52 | 29 |
| 53 | 2.251 | 1.296 | 2.218 | | 8/7 | 0 |
| 54 | 0.050 | 0.017 | 0.040 | | 10/7 | 0 |
| 55 | 0.020 | −0.007 | 0.017 | + | 14/8 | |
| 56 | 0.033 | −0.004 | 0.000 | | 9/3 | 0 |
| 57 | 1.396 | 0.718 | 2.121 | − | 17/11 | 1 |
| 58 | 0.045 | 0.013 | −0.003 | | 13/12 | |
| 59 | 0.014 | 0.068 | 0.056 | | 10/7 | 0 |
| 60 | 0.009 | 0.014 | 0.056 | + | 15/0 | 10 |
| 61 | 2.007 | 2.214 | 2.235 | + | 12/9 | |
| 62 | 0.171 | 0.001 | 0.003 | | 11/7 | 0 |
| 63 | 1.121 | 0.529 | 2.383 | + | 18/10 | |
| 64 | 0.113 | 0.066 | 0.002 | | 4/3 | 0 |
| 65 | 0.032 | 0.003 | −0.003 | + | 7/5 | 3 |
| 66 | 0.039 | −0.001 | −0.002 | + | 11/6 | |
| 67* | 0.049 | 0.037 | 2.119 | | 16/11 | |
| 68* | 0.177 | 0.638 | 2.000 | + | 24/25 | 33 |
| 69 | 0.027 | 0.007 | −0.007 | | 6/3 | 0 |
| 70 | 0.031 | −0.006 | −0.001 | | 16/9 | 0 |
| 71 | 0.781 | 0.473 | 2.151 | + | 13/8 | 14 |
| 72 | 0.110 | 0.002 | 0.059 | | 13/8 | 0 |
| 73 | 0.043 | −0.002 | −0.007 | − | 2/3 | 0 |
| 74 | 0.014 | 0.001 | −0.004 | | 2/3 | 0 |
| 75 | 0.053 | 0.000 | 0.019 | + | 15/8 | |
| 76 | 0.060 | 0.015 | 0.018 | | 14/7 | 0 |
| 77 | 0.011 | 0.001 | −0.004 | | 8/8 | |
| 78 | 0.042 | 0.002 | 0.023 | | 3/0 | 0 |
| 79 | 0.537 | 0.219 | 1.742 | + | 11/7 | |
| 80 | 2.615 | 1.713 | 2.428 | + | 18/16 | 12 |

TABLE 9-continued

HCV Positivity in Serum Specimens Obtained from Japanese Dialysis Patients

| Code No. | rDNA based HCA EIA OD Cutoff = 0.40 | Peptide based HCV EIA Format A Cutoff = 0.205 | Peptide based HCV EIA Format C Cutoff = 0.204 | HBsAb | GOT/GPT Oct, 89 | n: times during 1986-1988 when GPT >25 I.U./L |
|---|---|---|---|---|---|---|
| 81 | 2.509 | 2.265 | 2.294 |  | 9/4 |  |
| 82 | 0.019 | 0.000 | 0.120 |  | 11/5 | 0 |
| 83 | 0.511 | 1.928 | 2.229 | — | 19/11 | 5 |
| 84 | 0.020 | 0.016 | 0.095 |  | 12/9 |  |
| 85 | 0.013 | −0.003 | 0.116 |  | 10/7 | 0 |
| 86 | 0.003 | −0.005 | −0.006 |  | 19/5 |  |
| 87 | 0.031 | −0.009 | 0.009 |  | 10/6 | 0 |
| 88 | 0.039 | 0.019 | 0.004 |  | 6/2 | 0 |
| 89* | 0.273 | 0.223 | 2.055 | — | 10/8 | 8 |
| 90 | 0.045 | 0.026 | −0.002 | — | 7/3 | 3 |
| 91 | 0.018 | 0.003 | −0.002 |  | 5/8 | 0 |
| 92 | 1.974 | 1.127 | 2.189 | + | 11/23 | 22 |
| 93 | 0.893 | 1.113 | 2.226 | — | 24/19 | 5 |
| 94* | 0.267 | 0.353 | 2.029 | — | 18/12 | 1 |
| 95 | 0.026 | −0.010 | 0.000 | — | 34/73 | 0 |
| 96* | 0.021 | 0.002 | 1.599 | — | 13/30 | 27 |
| 97* | 0.246 | 0.037 | 1.779 |  | 15/9 | 0 |
| 98 | 2.412 | 1.904 | 2.236 | — | 3/9 |  |

We claim:

1. A method of detecting antibodies to hepatitis C virus (HCV), or diagnosis of HCV infection or NANBH in a subject comprising the steps:

(i) providing a peptide composition comprising a peptide selected from the group consisting of:

Glu—Glu—Cys—Ser—Gln—His—Leu—Pro—Tyr—Ile—
Gly—Gln—Gly—Met—Met—Leu—Ala—Glu—Gln—Phe—
Lys—Gln—Lys—Ala—Leu—Gly—Leu—Leu—Gln—Thr—
Ala—Ser—Arg—Gln—Ala—Glu—Val—Ile—Ala—Pro—
X  (Peptide I);

Cys—Val—Val—Ile—Val—Gly—Arg—Val—Val—Leu—
Ser—Gly—Lys—Pro—Ile—Ala—Ile—Pro—Asp—Arg—
Glu—Val—Leu—Tyr—Arg—Glu—Phe—Asp—Glu—Met—
Glu—Glu—Cys—Ser—Gln—His—Leu—Pro—Tyr—Ile—
X  (Peptide III);

Ser—Gly—Lys—Pro—Ala—Ile—Ile—Pro—Asp—Arg—
Glu—Val—Leu—Tyr—Arg—Glu—Phe—Asp—Glu—Met—
Glu—Glu—Cys—Ser—Gln—His—Leu—Pro—Tyr—Ile—
Glu—Gln—Gly—Met—Met—Leu—Ala—Glu—Gln—Phe—
X  (Peptide IV);

Lys—Gln—Lys—Ala—Leu—Gly—Leu—Leu—Gln—Thr—
Ala—Ser—Arg—Gln—Ala—Glu—Val—Ile—Ala—Pro—
Ala—Val—Gln—Thr—Asn—Trp—Gln—Lys—Leu—Glu—
Thr—Phe—Trp—Ala—Lys—His—Met—Trp—Asn—Phe—
X  (Peptide V);

Glu—Gln—Gly—Met—Met—Leu—Ala—Glu—Gln—Phe—
Lys—Gln—Lys—Ala—Leu—Gly—Leu—Leu—Gln—Thr—
Ala—Ser—Arg—Gln—Ala—Glu—Val—Ile—Ala—Pro—
Ala—Val—Gln—Thr—Asn—Trp—Gln—Lys—Leu—Glu—
Thr—X  (Peptide VI);

Pro—Gly—Ala—Leu—Val—Val—Gly—Val—Val—Cys—
Ala—Ala—Ile—Leu—Arg—Arg—His—Val—Gly—Pro—
Gly—Glu—Gly—Ala—Val—Gln—Trp—Met—Asn—Arg—
Leu—Ile—Ala—Phe—Ala—Ser—Arg—Gly—Asn—His—
Val—Ser—Pro—X  (Peptide VII);

Ser—Thr—Ile—Pro—Lys—Pro—Gln—Arg—Lys—Thr—
Lys—Arg—Asn—Thr—Asn—Arg—Arg—Pro—Gln—Asp—
Val—Lys—Phe—Pro—Gly—Gly—Gly—Gln—Ile—Val—
Gly—Gly—Val—Tyr—Leu—Leu—Pro—Arg—Arg—Gly—
Pro—Arg—Leu—Gly—Val—Arg—Ala—Thr—Arg—Lys—
Thr—Ser—Glu—Arg—Ser—Gln—Pro—Arg—Gly—Arg—
Arg—X  (Peptide VIII);

Gly—Arg—Arg—Gln—Pro—Ile—Pro—Lys—Val—Arg—
Arg—Pro—Glu—Gly—Arg—Thr—Trp—Ala—Gln—Pro—
Gly—Tyr—Pro—Trp—Pro—Leu—Tyr—Gly—Asn—Glu—
Gly—Cys—Gly—Trp—Ala—Gly—Trp—Leu—Leu—Ser—
Pro—Arg—Gly—Ser—Arg—Pro—Ser—Trp—Gly—Pro—
Thr—Asp—Pro—Arg—Arg—Arg—Ser—Arg—Asn—Leu—
Gly—X  (Peptide IX);

wherein X is —OH or NH$_2$;

an analogue peptide of any one of the above peptides having an amino acid sequence from a strain/isolate of HCV in a region corresponding to the peptide and having specific immunoreactivity to antibodies to HCV;

a segment of any one of the above peptides or said analogue peptides having specific immunoreactivity to antibodies to HCV;

mixture of the above peptides, said analogue peptides or said segments;

a conjugate of any one of the above peptides, said analogue peptides or said segments with carrier proteins, the conjugate having specific immunoreactivity to antibodies to HCV; and a polymer of any one of the peptides, said analogue peptides or said segments having specific immunoreactivity to antibodies to HCV comprising a branching dimer, tetramar, or octomar of the peptide on a mono, tri, or hepta lysine core, respectively;

(ii) contacting an effective amount of the peptide composition with a sera or body fluid sample from the subject; and (iii) detecting the presence of a complex of the peptide composition and antibodies to HCV or NANBHV.

2. The method according to claim 1, wherein the peptide composition is coated on a solid substrate.

3. The method according to claim 2, wherein the step of detecting the presence of the complex of peptide with antibodies to HCV or NANBHV is by means of an enzyme linked immunosorbent assay.

4. The method according to claim 2, wherein the method of detecting the presence of the complex of peptide with antibodies to HCV or NANBHV is by using an immunoradiometric assay.

5. The method according to claim 1, wherein the method of detecting the presence of the complex or peptide with antibodies to HCV or NANBHC is by an agglutination assay.

6. The method according to claim 1, wherein the peptide composition is a segment of peptide III and has an amino acid sequence selected from the group consisting of:

Ile—Ile—Pro—Asp—Arg—Glu—Val—Leu—Tyr—Arg—Glu—Phe— (i)
Asp—Glu—Met—Glu—Glu—Cys—Ser—Gln—His—Leu—Pro—Tyr—
Ile—X;    (Peptide IIIC)

Ser—Gly—Lys—Pro—Ala—Ile—Ile—Pro—Asp—Arg—Glu—Val— (ii)
Leu—Tyr—Arg—Glu—Phe—Asp—Glu—Met—Glu—Glu—Cys—Ser—
Gln—His—Leu—Pro—Tyr—Ile—X;    (Peptide IIID)

Gly—Arg—Val—Val—Leu—Ser—Gly—Lys—Pro—Ala—Ile—Ile— (iii)
Pro—Asp—Arg—Glu—Val—Leu—Tyr—Arg—Glu—Phe—Asp—Glu—
Met—Glu—Glu—Cys—Ser—Gln—His—Leu—Pro—Tyr—Ile—X;
   (Peptide IIIE)

wherein in each of Peptides IIIC, IIID, and IIIE X is —OH or —NH$_2$; and an analogue peptide of any one of the above peptides having an amino acid sequence from a strain/isolate of HCV in a region corresponding to the peptide and having specific immunoreactivity to antibodies to HCV.

7. The method according to claim 6, wherein the peptide composition comprises a peptide having an amino acid sequence:

Ser—Gly—Lys—Pro—Ala—Ile—Ile—Pro—Asp—Arg—Glu—Val— (ii)
Leu—Tyr—Arg—Glu—Phe—Asp—Glu—Met—Glu—Glu—Cys—Ser—
Gln—His—Leu—Pro—Tyr—Ile—X;    (Peptide IIID)

wherein X is —OH or —NH$_2$; or an analogue peptide of the above peptide having an amino acid sequence from a strain/isolate of HCV in a region corresponding to the peptide and having specific immunoreactivity to antibodies to HCV.

8. The method according to claim 1, wherein the peptide composition comprises a segment of Peptide VIII and has an amino acid sequence selected from the group consisting of:

Thr—Lys—Arg—Asn—Thr—Asn—Arg—Arg—Pro—Gln—Asp—Val— (i)
Lys—Phe—Pro—Gly—Gly—Gly—Gln—Ile—Val—Gly—Gly—Val—
Tyr—Leu—Leu—Pro—Arg—Arg—Gly—Pro—Arg—Leu—Gly—Val—
Arg—Ala—Thr—Arg—Lys—Thr—Ser—Glu—Arg—Ser—Gln—Pro—
Arg—Gly—Arg—Arg—X;    (Peptide VIIID)

Asp—Val—Lys—Phe—Pro—Gly—Gly—Gly—Gln—Ile—Val—Gly— (ii)
Gly—Val—Tyr—Leu—Leu—Pro—Arg—Arg—Gly—Pro—Arg—Leu—
Gly—Val—Arg—Ala—Thr—Arg—Lys—Thr—Ser—Glu—Arg—Ser—
Gln—Pro—Arg—Gly—Arg—Arg—X;    (Peptide VIIIC)

Val—Gly—Gly—Val—Tyr—Leu—Leu—Pro—Arg—Arg—Gly— (iii)
Pro—Arg—Leu—Gly—Val—Arg—Ala—Thr—Arg—Lys—Thr—
Ser—Glu—Arg—Ser—Gln—Pro—Arg—Gly—Arg—Arg—X;    (Peptide VIIIB)

Gly—Pro—Arg—Leu—Gly—Val—Arg—Ala—Thr—Arg—Lys—Thr— (iv)
Ser—Glu—Arg—Ser—Gln—Pro—Arg—Gly—Arg—Arg—X;    (Peptide VIIIA)

wherein in each of Peptide VIIID, VIIIC, VIIIB, and VIIIA X is -13 OH or —NH$_2$; and an analogue peptide of any one of the above peptides having an amino acid sequence from a strain/isolate of HCV in a region corresponding to the peptide and having specific immunoreactivity to antibodies to HCV.

9. The method according to claim 1, wherein the peptide composition comprises a segment of Peptide IX and has an amino acid sequence selected from the group consisting of:

Ile—Pro—Lys—Val—Arg—Arg—Pro—Glu—Gly—Arg—Thr—Trp— (i)
Ala—Gln—Pro—Gly—Tyr—Pro—Trp—Pro—Leu—Tyr—Gly—Asn—
Glu—Gly—Cys—Gly—Trp—Ala—Gly—Trp—Leu—Leu—Ser—Pro—
Arg—Gly—Ser—Arg—Pro—Ser—Trp—Gly—Pro—Thr—Asp—Pro—
Arg—Arg—Arg—Ser—Arg—Asn—Leu—Gly—X;    (Peptide IXD)

Thr—Trp—Ala—Gln—Pro—Gly—Tyr—Pro—Trp—Pro—Leu—Tyr— (ii)
Gly—Asn—Glu—Gly—Cys—Gly—Trp—Ala—Gly—Trp—Leu—Leu—
Ser—Pro—Arg—Gly—Ser—Arg—Pro—Ser—Trp—Gly—Pro—Thr
Asp—Pro—Arg—Arg—Arg—Ser—Arg—Asn—Leu—Gly—X    (Peptide IXC)

Leu—Tyr—Gly—Asn—Glu—Gly—Cys—Gly—Trp—Ala—Gly—Trp— (iii)
Leu—Leu—Ser—Pro—Arg—Gly—Ser—Arg—Pro—Ser—Trp—Gly—
Pro—Thr—Asp—Pro—Arg—Arg—Arg—Ser—Arg—Asn—Leu—
Gly—X;    (Peptide IXB)

Trp—Ala—Gly—Trp—Leu—Leu—Ser—Pro—Arg—Gly—Ser—Arg— (iv)
Pro—Ser—Trp—Gly—Pro—Thr—Asp—Pro—Arg—Arg—Arg—Ser—

Arg—Asn—Leu—Gly—X; (Peptide IXA)

wherein in each of Peptides IXD, IXC, IXB, and IXA X is —OH or —NH₂; and an analogue peptide of any one of the above peptides having an amino acid sequence from a strain/isolate of HCV in a region corresponding to the peptide and having specific immunoreactivity to antibodies to HCV.

10. A method of detecting antibodies to hepatitis C virus (HCV), or diagnosis of HCV infection or NANBH in a subject comprising the steps:
(i) providing a peptide composition comprising a peptide having an amino acid sequence as follows:

Ser—Thr—Ile—Pro—Lys—Pro—Gln—Arg—Lys—Thr—Lys—Arg—
Asn—Thr—Asn—Arg—Arg—Pro—Gln—Asp—Val—Lys—Phe—Pro—
Gly—Gly—Gly—Gln—Ile—Val—Gly—Gly—Val—Tyr—Leu—Leu—
Pro—Arg—Arg—Gly—Pro—Arg—Leu—Gly—Val—Arg—Ala—Thr—
Arg—Lys—Thr—Ser—Glu—Arg—Ser—Gln—Pro—Arg—Gly—Arg—
Arg—X; (Peptide VIII)

wherein X is —OH or —NH₂; an analogue peptide of the above peptide having an amino acid sequence from a strain/isolate of HCV in a region corresponding to the peptide, and having specific immunoreactivity to antibodies to HCV; or a segment of the above peptide or said analogue peptide having specific immunoreactivity to antibodies to HCV;

(ii) contacting an effective amount of the peptide composition with a sera or body fluid sample from the subject; and
(iii) detecting the presence of a complex of the peptide composition and antibodies to HCV or NANBHV.

11. The method according to claim 1, wherein the peptide composition comprises a peptide having an amino acid sequence as follows:

Gly—Arg—Arg—Gln—Pro—Ile—Pro—Lys—Val—Arg—Arg—Pro—
Glu—Gly—Arg—Thr—Trp—Ala—Gln—Pro—Gly—Tyr—Pro—Trp—
Pro—Leu—Tyr—Gly—Asn—Glu—Gly—Cys—Gly—Trp—Ala—Gly—
Trp—Leu—Leu—Ser—Pro—Arg—Gly—Ser—Arg—Pro—Ser—Trp—
Gly—Pro—Thr—Asp—Pro—Arg—Arg—Arg—Ser—Arg—Asn—Leu—
Gly—X; (Peptide IX)

wherein X is —OH or —NH₂; an analogue peptide of the above peptide having an amino acid sequence from a strain/isolate of HCV in a region corresponding to the peptide, and having specific immunoreactivity to antibodies to HCV; or a segment of the above peptide or said analogue peptide having specific immunoreactivity to antibodies to HCV.

12. A method of detecting antibodies to hepatitis C virus (HCV), or diagnosis of HCV infection or NANBH in a subject comprising the steps:
(i) preparing a peptide composition comprising Peptide II having an amino acid sequence as follows:

Ser—Gly—Lys—Pro—Ala—Ile—Ile—Pro—Asp—Arg—Glu—Val—
Leu—Tyr—Arg—Glu—Phe—Asp—Glu—Met—Glu—Glu—Cys—Ser—
Gln—His—Leu—Pro—Tyr—Ile—Glu—Gln—Gly—Met—Met—Leu—
Ala—Glu—Gln—Phe—Lys—Gln—Lys—Ala—Leu—Gly—Leu—X; (Peptide II)

wherein X is —OH or —NH₂; or an analogue peptide of the above peptide having an amino acid sequence from a strain/isolate of HCV in a region corresponding to the peptide and having specific immunoreactivity to antibodies to HCV;

(ii) Contacting an effective amount of the peptide composition with a sera or body fluid sample from the subject;
(iii) Detecting the presence of a complex of peptide composition with antibodies to HCV or NANBHV.

13. The method according to claim 12, wherein the peptide composition comprises a segment of Peptide II and has an amino acid sequence selected from the group consisting of:

Cys—Ser—Gln—His—Leu—Pro—Tyr—Ile—Glu—Gln—Gly—Met— (i)
Met—Leu—Ala—Glu—Gln—Phe—Lys—Gln—Lys—Ala—Leu—Gly—
Leu—X; (Peptide IIC)

Asp—Glu—Met—Glu—Glu—Cys—Ser—Gln—His—Leu—Pro—Tyr— (ii)
Ile—Glu—Gln—Gly—Met—Met—Leu—Ala—Glu—Gln—Phe—Lys—
Gln—Lys—Ala—Leu—Gly—Leu—X; (Peptide IID)

Leu—Tyr—Arg—Glu—Phe—Asp—Glu—Met—Glu—Glu—Cys—Ser— (iii)
Gln—His—Leu—Pro—Tyr—Ile—Glu—Gln—Gly—Met—Met—Leu—
Ala—Glu—Gln—Phe—Lys—Gln—Lys—Ala—Leu—Gly—Leu—X; (Peptide IIE)

Pro—Asp—Arg—Glu—Val—Leu—Tyr—Arg—Glu—Phe—Asp—Glu— (iv)
Met—Glu—Glu—Cys—Ser—Gln—His—Leu—Pro—Tyr—Ile—Glu—
Gln—Gly—Met—Met—Leu—Ala—Glu—Gln—Phe—Lys—Gln—Lys—
Ala—Leu—Gly—Leu—X; (Peptide IIF)

wherein X is —OH or —NH₂; or an analogue peptide of any one of the above peptides having an amino acid sequence from a strain/isolate of HCV in a region corresponding to the peptide and having specific immunoreactivity to antibodies to HCV.

14. The method according to claim 13, wherein the peptide composition comprises a peptide having an amino acid sequence:

Pro—Asp—Arg—Glu—Val—Leu—Tyr—Arg—Glu—Phe—Asp—Glu—
Met—Glu—Glu—Cys—Ser—Gln—His—Leu—Pro—Tyr—Ile—Glu—
Gln—Gly—Met—Met—Leu—Ala—Glu—Gln—Phe—Lys—Gln—Lys—
Ala—Leu—Gly—Leu—X; (Peptide IIF)

wherein X is —OH or —NH₂; or an analogue peptide of the above peptide having an amino acid sequence from a strain/isolate of HCV in a region corresponding to the peptide and having specific immunoreactivity to antibodies to HCV.

* * * * *